United States Patent
Tölli et al.

(10) Patent No.: US 11,219,665 B2
(45) Date of Patent: Jan. 11, 2022

(54) METHOD FOR PREPARING A BONE PROTEIN PREPARATION AND A BONE PROTEIN PREPARATION

(71) Applicant: BBS-Bioactive Bone Substitutes OYJ, Oulu (FI)

(72) Inventors: Hanna Tölli, Reisjärvi (FI); Juha-Matti Närhi, Lempäälä (FI); Harri Lumme, Oulu (FI); Elli Birr, Kempele (FI); Oili Hietala, Oulu (FI); Mikko Viitanen, Oulu (FI); Merja Haikola, Raisio (FI); Pekka Jalovaara, Oulu (FI); Bo Kenneth Sandström, Turku (FI)

(73) Assignee: BBS-Bioactive Bone Substitutes OYJ, Oulu (FI)

( * ) Notice: Subject to any disclaimer, the term of this patent is extended or adjusted under 35 U.S.C. 154(b) by 116 days.

(21) Appl. No.: 16/867,434

(22) Filed: May 5, 2020

(65) Prior Publication Data

US 2020/0289617 A1    Sep. 17, 2020

Related U.S. Application Data

(62) Division of application No. 13/806,944, filed as application No. PCT/EP2011/060702 on Jun. 27, 2011, now Pat. No. 10,702,584.

(30) Foreign Application Priority Data

Jun. 28, 2010 (EP) .................................... 10167448
Apr. 1, 2011 (EP) .................................... 11160828

(51) Int. Cl.

| | |
|---|---|
| A61K 35/32 | (2015.01) |
| A61K 38/18 | (2006.01) |
| A61L 27/36 | (2006.01) |
| A61K 9/16 | (2006.01) |
| A61K 38/17 | (2006.01) |
| A61K 38/39 | (2006.01) |
| A61K 38/44 | (2006.01) |
| A61K 38/48 | (2006.01) |

(52) U.S. Cl.
CPC ........ *A61K 38/1875* (2013.01); *A61K 9/1676* (2013.01); *A61K 35/32* (2013.01); *A61K 38/1709* (2013.01); *A61K 38/1738* (2013.01); *A61K 38/1841* (2013.01); *A61K 38/39* (2013.01); *A61K 38/44* (2013.01); *A61K 38/4833* (2013.01); *A61L 27/365* (2013.01); *A61L 27/3608* (2013.01); *A61L 27/3687* (2013.01); *A61L 2300/252* (2013.01); *A61L 2430/02* (2013.01)

(58) Field of Classification Search
None
See application file for complete search history.

(56) References Cited

U.S. PATENT DOCUMENTS

| | | |
|---|---|---|
| 6,511,958 B1 | 1/2003 | Atkinson et al. |
| 2004/0072322 A1 | 4/2004 | Thorne |
| 2005/0098915 A1 | 5/2005 | Long et al. |
| 2006/0093640 A1 | 5/2006 | Duneas |
| 2008/0241072 A1 | 10/2008 | Barry et al. |
| 2009/0148487 A1 | 6/2009 | Siedler et al. |
| 2010/0041611 A1 | 2/2010 | Thorne et al. |

FOREIGN PATENT DOCUMENTS

| | | |
|---|---|---|
| CA | 2840546 A1 | 1/2012 |
| EA | 024470 B1 | 9/2016 |
| EP | 2105149 B9 | 11/2011 |
| EP | 2585083 B1 | 9/2015 |
| WO | WO 02/47713 A2 | 6/2002 |
| WO | WO 2007/053850 A2 | 5/2007 |

OTHER PUBLICATIONS

Ulmanen, Mari S. et al., "Osteoinductivity of partially purified native ostrich (*Struthio camelus*) bone morphogenetic protein: Comparison with mammalian species" Life Sciences, 2005, pp. 2425-2437, vol. 77.
Communication pursuant to Article 94(3) EPC for Application No. 11729961.0—1456 dated Jul. 18, 2014.
International Preliminary Report on Patentability for PCT/EP2011/060702 dated Oct. 25, 2012.
International Search Report for PCT/EP2011/060702 dated Oct. 10, 2011.
Ramage, Samuel, "The Role of Secreted Phosphoprotein-24 in Osteoblast Differentiation and Matrix Mineralization. Theses and Dissertations, Paper 1604." Virginia Commonwealth University, 2007, pp. 1-165.

*Primary Examiner* — David J Blanchard
*Assistant Examiner* — Daniel F Coughlin
(74) *Attorney, Agent, or Firm* — Knobbe, Martens, Olson & Bear, LLP

(57) ABSTRACT

The present invention provides a method for preparing a bone protein preparation which contains for example growth factors. The present invention also provides a bone protein preparation obtained by the method and paste, putty, pellet, disc, block, granule, osteogenic device or pharmaceutical composition containing said bone protein preparation.

10 Claims, 34 Drawing Sheets

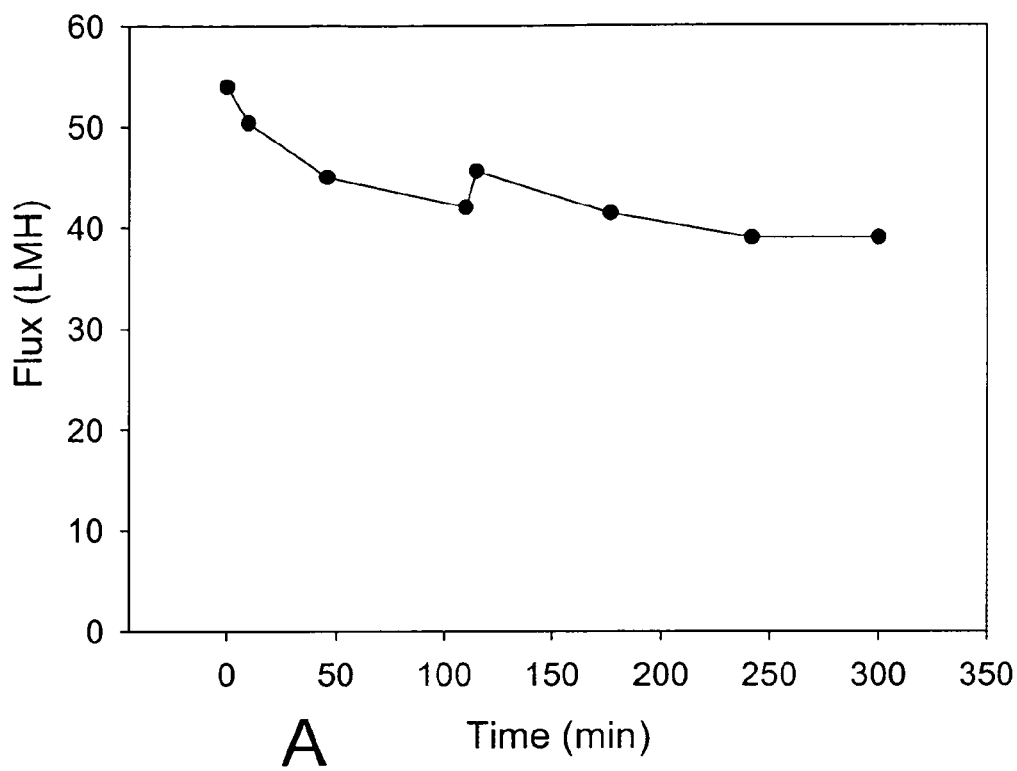
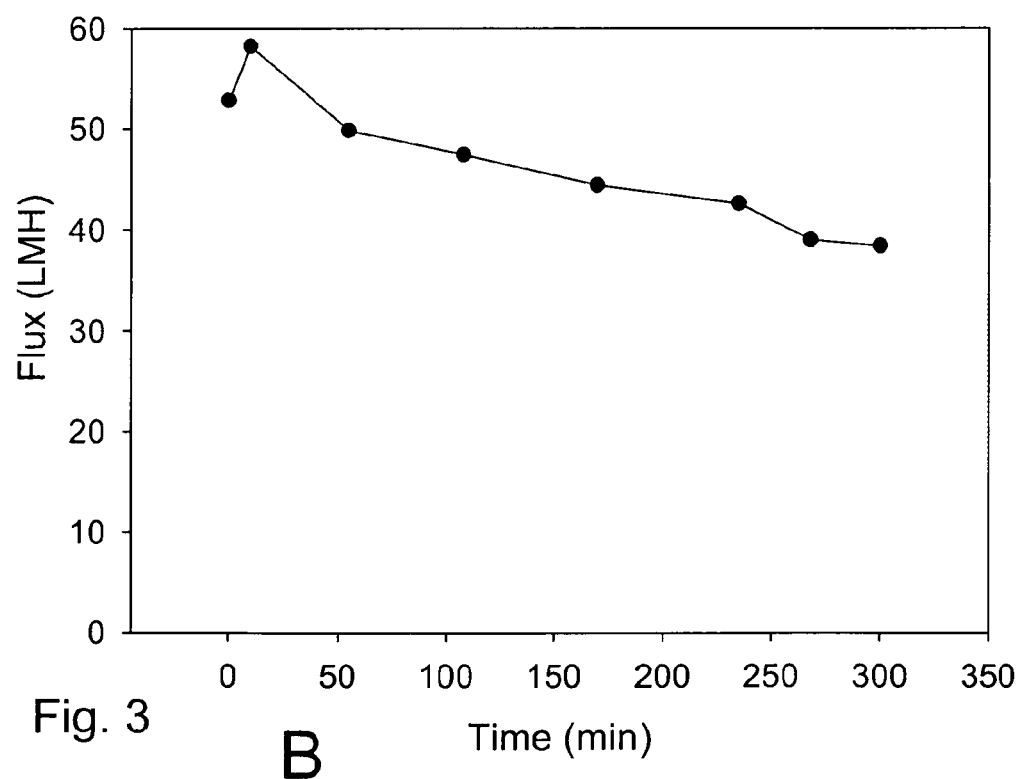
Fig. 3

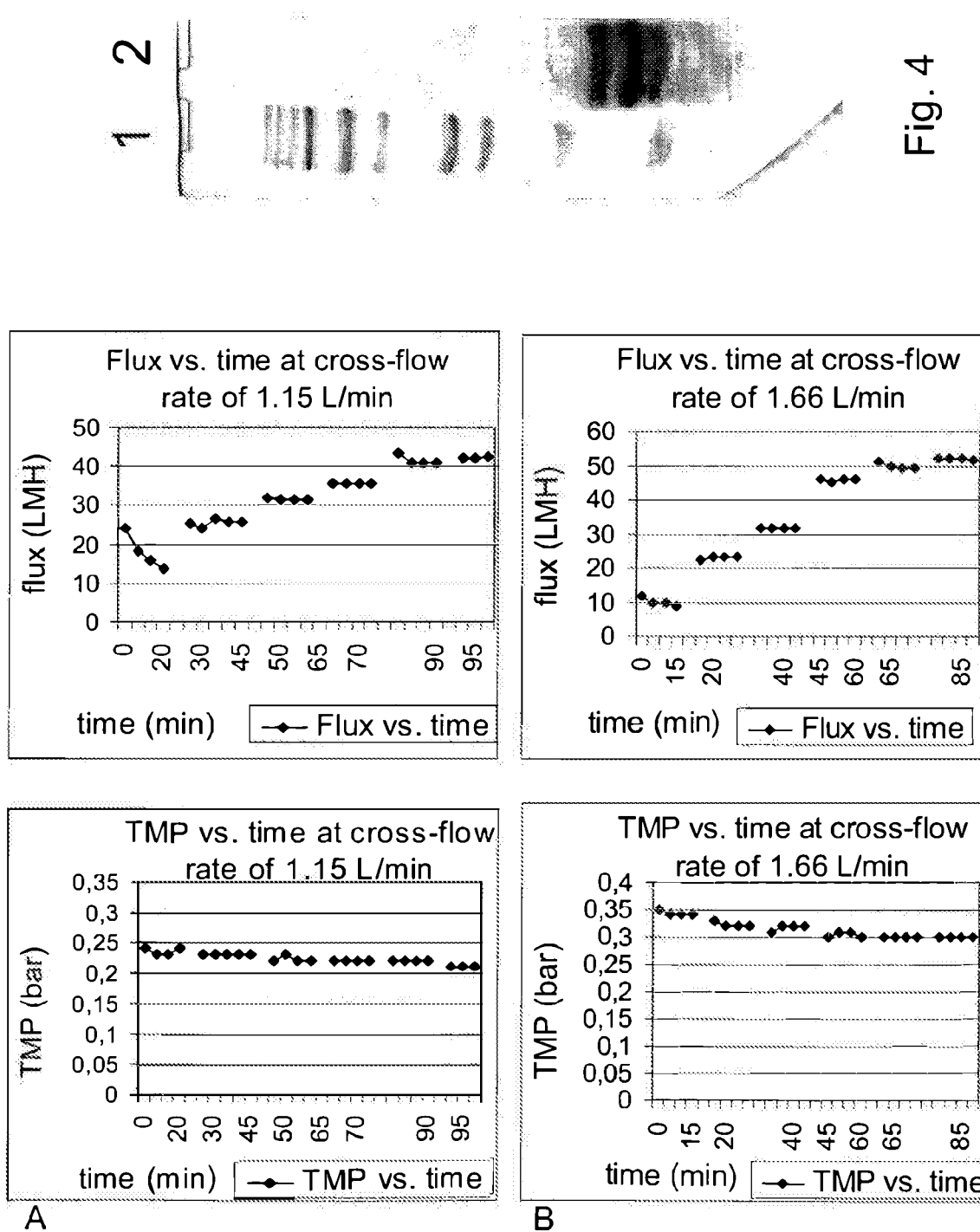

P2.1 (F001)  P2.2 (F002)

P7.1 (F001)  P3U.2 (F002)

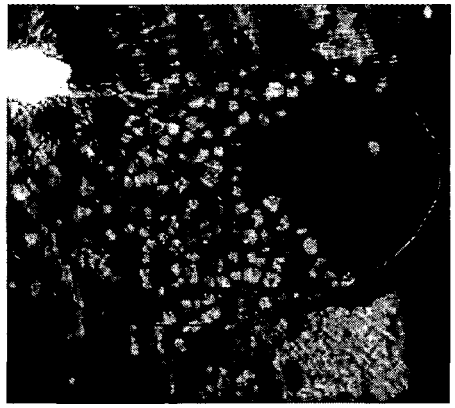
P2.3 (F003)
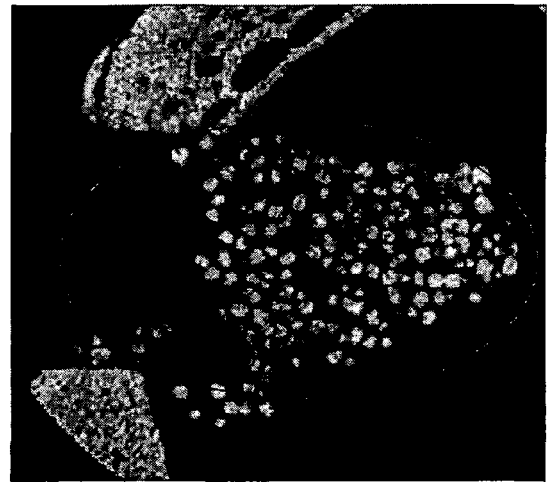
P2.4 (F004)
Fig. 27
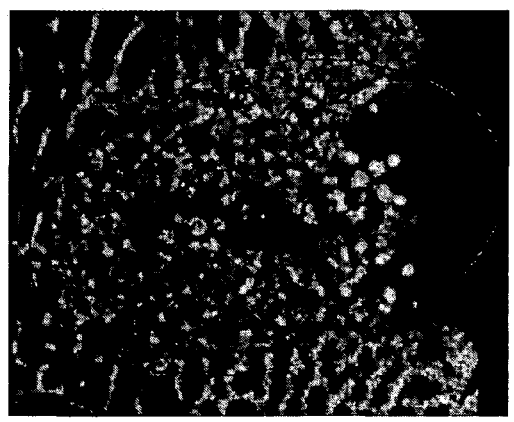
P7.3 (F003)
P7.4 (F004)
Fig. 28

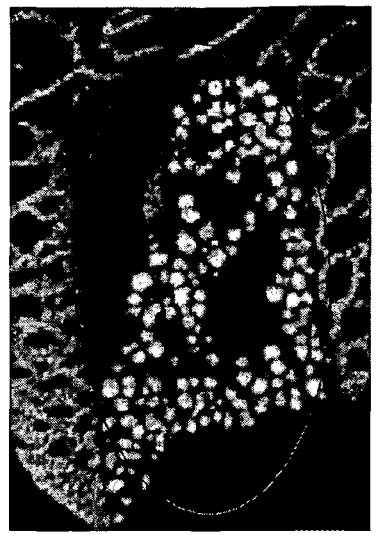
P5.1 (F005)
Fig. 29
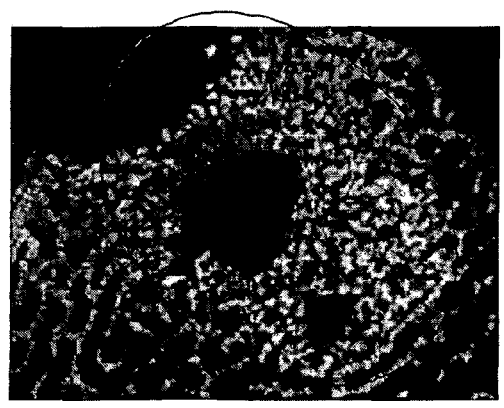
P9.1 (F005)
P10.3 (F006)
Fig. 30

P5.2 (Empty)

P10.4 (Empty)

METHOD FOR PREPARING A BONE PROTEIN PREPARATION AND A BONE PROTEIN PREPARATION

Aspects of the present invention relate to methods for preparing bone protein preparations. Several embodiments also concern bone protein preparations obtained by these methods, and compositions containing one or more of these preparations, including osteogenic devices.

BACKGROUND OF THE INVENTION

In the orthopedic and periodontal surgical fields it is highly desirable to find efficient systems for treating patients with skeletal disorders and deformations, including the repairing of large bone defects originating from trauma, excision of tumors and congenital malformations, reconstructing bone stocks worn off by an implanted endoprothesis in revision operations and healing delayed or non-united fractures.

The autologous graft ("autograft") is the traditional approach to bone repair, but the harvesting of bone grafts can lead to complications, such as bleeding, pain, and infection. Autografts have also limited availability thus, as an alternative, many inorganic materials are used. Calcium phosphates such as hydroxyapatite (HAP) and tricalcium phosphates (TCP) and their variations are commonly known bone substitute materials. These materials provide an osteoconductive scaffold to new bone forming.

The bioactivity of inorganic materials can be increased by adding osteogenic stimulus to the bone graft extender. Allografts, demineralised bone matrices (DBM) and native bone extracts have been shown to increase bone healing capacity and enhance integration in many different studies. Combinations of bovine bone-derived growth factors in collagen and DBM or coralline HAP carriers have been shown to be as good as iliac crest autografts when studied as fusion rates in spinal arthrodesis in rabbits and monkeys.

Commercially available synthesized biomaterials have been developed and can be used as filling material or inlay as well as onlay support. Unfortunately, these materials lack the biological activity needed to initiate bone regeneration. Synthetic carriers prepared from such materials including polylactic acids and hyaluronic acids are described e.g. in the patent U.S. Pat. No. 5,366,508. Bone morphogenetic protein (BMP) is considered an important factor in osteogenic devices and participates actively in the implantation process.

EP 0 883 410 B1 discloses a method for producing the modified bone morphogenetic protein (BMP) complex for an osteogenic device wherein the modified BMP complex is obtainable by a method comprising the steps of (a) pulverizing demineralized bone material; (b) extracting the bone material in step (a) with guanidinium hydrochloride (GuHCl); (c) performing a filtration using a tangential flow system; (d) performing a gel filtration by which a partially purified BMP complex demonstrating three peaks comprising three protein fractions, which are characterized by having different molecular weights, Fraction I being a high MW (100-700 kD) protein with osteoinductive BMP activity, Fraction II being a medium MW (25-55 kD) immunogenic protein lacking BMP activity and Fraction III being a low MW (15-25 kD) protein with osteoinductive BMP activity is obtainable; and (e) removing from the partially purified BMP a protein fraction with immunogenic and inflammatory properties having a MW of 25-55 kD as determined by gel filtration.

The need for more osteogenic materials that are useful for a variety of bone repair applications, especially, materials that are compatible with the carrier materials typically used in the applications described above, is manifest.

SUMMARY OF THE INVENTION

It was surprisingly discovered that a bone protein extract containing growth factors, among other proteins, provides unique osteogenic properties. The bone protein extract, for example, can accelerate desorption of a scaffold or carrier, wherein the extract is incorporated.

Accordingly, several embodiments include methods for preparing a bone protein preparation, wherein the methods are practiced by:

a) demineralizing the bone and extracting the bone matrix with guanidine hydrochloride to obtain a bone protein extract, b) filtering the extract with a microfilter with cut-off size sufficient for removing big particles and non-proteinous material but enabling proteins to pass, c) filtering the flow-through with a cassette ultrafilter having the cut-off size about 5-10 kDa to recover the bone protein preparation.

Several embodiments described herein comprise a bone protein preparation obtained by one or more of the aforementioned methods.

Some embodiments include a bone protein preparation containing growth factors, differentiation factors and signaling molecules which provide, when combined, a synergistic effect and/or activity which can be useful for osteoinductive purposes e.g. to promote advantageous bone induction properties. The growth factors, differentiation factors and signaling molecules may include proteins defined herein, such as bone morphogenetic protein(s) (BMP) and proteins found in native demineralized bone extracts. In one embodiment the bone protein preparation containing growth factors, differentiation factors and signaling molecules is obtained with any method described herein.

Aspects of the present invention also include a bone protein preparation containing one or more of the proteins described herein, for example, some embodiments comprise or consist essentially of a Matrix Gla protein, SPP-24 (secreted phosphoprotein), BMP-2, BMP-7 and/or TGF-beta 1.

Aspects of the invention also include pastes or gels, such as an injectable paste or gel, comprising one or more of the bone protein preparations described herein. The paste or gel may be mouldable, which form may also be called putty.

Accordingly, some embodiments include a putty, a pellet, a disc, a block or a granule comprising a bone protein preparation that comprises one or more of the proteins described herein, for example, some embodiments comprise or consist essentially of a Matrix Gla protein, SPP-24 (secreted phosphoprotein), BMP-2, BMP-7 and/or TGF-beta 1.

Some embodiments also include an osteogenic device, such as a bone implant, containing one or more of the bone protein preparations described herein, for example impregnated in matrix, such as a porous matrix. That is, some embodiments are osteogenic devices that comprise one or more of the proteins described herein, for example, some embodiments comprise or consist essentially of a Matrix Gla protein, SPP-24 (secreted phosphoprotein), BMP-2, BMP-7 and/or TGF-beta 1. In some embodiments, one or more of the bone protein preparations described herein may be used for treating, ameliorating, inhibiting, or preventing a disorder or condition related to bone, cartilage, tendon or tooth defects, wherein regeneration, repair or growth thereof is desired, such as cancer.

Some embodiments described herein include a pharmaceutical composition containing one or more of the bone protein preparations described herein. These pharmaceutical compositions may be used for treating, ameliorating, inhibiting, or preventing a disorder or condition related to bone, cartilage, tendon or tooth defects, wherein regeneration, repair or growth thereof is desired, such as cancer.

In some embodiments, methods for inducing the formation of bone, cartilage, tendon, or teeth, in vitro or in vivo, are contemplated and these methods are practiced by providing or administering one or more of the bone preparations described herein (desirably, in an osteogenic device or suitable matrix) to a subject in need thereof, e.g., a human or animal (including domestic and companion animals). Optionally, the subject can be identified or classified as a subject in need of an agent that induces formation of bone, cartilage, tendon, or teeth and such evaluation can be made by clinical diagnosis by a physician, dentist, or surgeon. Optionally, these methods also include analysis, observation, measurement, or clinical evaluation of the bone, cartilage, tendon, or tooth formation before and/or after providing or administering one or more of the bone preparations described herein (desirably, in an osteogenic device or suitable matrix) to the subject in need thereof.

In more embodiments, methods for treating, ameliorating, inhibiting, or preventing a disorder or condition related to bone or cartilage defects, such as cancer, are contemplated. These methods can be practiced by providing or administering one or more of the bone preparations described herein (desirably, in an osteogenic device or suitable matrix) to a subject in need thereof, e.g., a human or animal (including domestic and companion animals). Optionally, the subject can be identified or classified as a subject in need of an agent that treats, ameliorates, inhibits, or prevents a disorder or condition related to bone or cartilage defects, such as cancer, and such evaluation can be made by clinical diagnosis by a physician, dentist, or surgeon. Optionally, these methods also include analysis, observation, measurement, or clinical evaluation of the bone, cartilage, tendon, or tooth formation before and/or after providing or administering one or more of the bone preparations described herein (desirably, in an osteogenic device or suitable matrix) to the subject in need thereof. Optionally, these methods also include analysis, observation, measurement, or clinical evaluation of the progression, inhibition, amelioration, or treatment of the disease, disorder, or condition associated therewith and these analyses, observations, or measurements can be made by clinical evaluation or diagnostic approaches.

In still more embodiments, one or more of the bone protein extracts described herein are combined with a scaffold or carrier, such as tricalcium phosphate or calcium sulfate, and the resultant composition is used to accelerate the desorption of the scaffold or carrier, thereby, improving the bone healing process, in a subject in need of bone healing. Accordingly, methods for accelerating the formation of bone, cartilage, tendon, or teeth, in vitro or in vivo, are contemplated and these methods are practiced by providing or administering a composition comprising one or more of the bone protein extracts described herein and tricalcium phosphate or calcium sulfate to a subject in need thereof, e.g., a human or animal (including domestic and companion animals). Optionally, the subject can be identified or classified as a subject in need of an agent that accelerates formation of bone, cartilage, tendon, or teeth and such evaluation can be made by clinical diagnosis by a physician, dentist, or surgeon. Optionally, these methods also include analysis, observation, measurement, or clinical evaluation of the bone, cartilage, tendon, or tooth formation before and/or after providing or administering one or more of the bone preparations described herein (desirably, in an osteogenic device or suitable matrix) to the subject in need thereof.

BRIEF DESCRIPTION OF THE DRAWINGS

FIG. 3 shows the flux rates during ultrafiltration through type V 10 kDa filters. A stands for 22 liter batch and B for 23 liter batch.

FIG. 4 shows a SDS-PAGE analysis of the end permeate from the filtration through type V 10 kDa cassette filter (lane 2). The electrophoresis was performed using reduced conditions and constant voltage of 200 V for 50 minutes. The sizes of molecular weight standard proteins (lane 1) starting from the top are 250, 150, 100, 75, 50, 37, 25, 20, 15 and 10 kDa.

FIG. 5 shows the determination of critical flux for microfiltration. Flux (up) and TMP (down) at initial cross-flow rates of 1.15 l/min (A) and 1.66 l/min (B).

FIG. 23A shows HAP/TCP/CS 30:60:10 active, FIG. 23B shows HAP/TCP/CS 30:60:10 control without bone protein extract, FIG. 23C shows CS hemihydrate active, FIG. 23D shows CS hemihydrate control, FIG. 23E shows CS dihydrate+stearic acid active, and FIG. 23F shows CS dihydrate+stearic acid control. C=calcified cartilage cells, B=bone, M=muscle, F=fibrotic tissue, and I=implant carrier. (Original magnification 10×).

FIG. 24A shows HAP/TCP/CS 30:60:10, FIG. 24B shows CS hemihydrate, and FIG. 24C shows CS dihydrate+stearic acid.

FIG. 27 shows μCT examples of β-TCPld active (P2.3) and control (P2.4) groups after 3 weeks follow-up. Some bone formation around the granules can be seen. Resorption of granules is yet slow.

FIG. 28 shows μCT examples of β-TCPld active (P7.3) and control (P7.4) groups after 8 weeks follow-up. Most of TCP-granules have resorbed in active side and replaced by new bone. On the control side granules have resorbed slower and bone formation can be found only around the granules. There is clearly more bone formation in the active group than in the control group.

FIG. 29 shows μCT example of β-TCPhd active group after 3 weeks follow-up. Granules did not yet resorbed and bone formation can be found around the granules. Control example is missing.

FIG. 30 shows μCT examples of β-TCPhd active (P9.1) and control (P10.3) groups after 8 weeks follow-up. Bone formation is more effective and resorption of granules is faster in active side compared to control side.

DETAILED DESCRIPTION OF THE INVENTION

Figure 1:
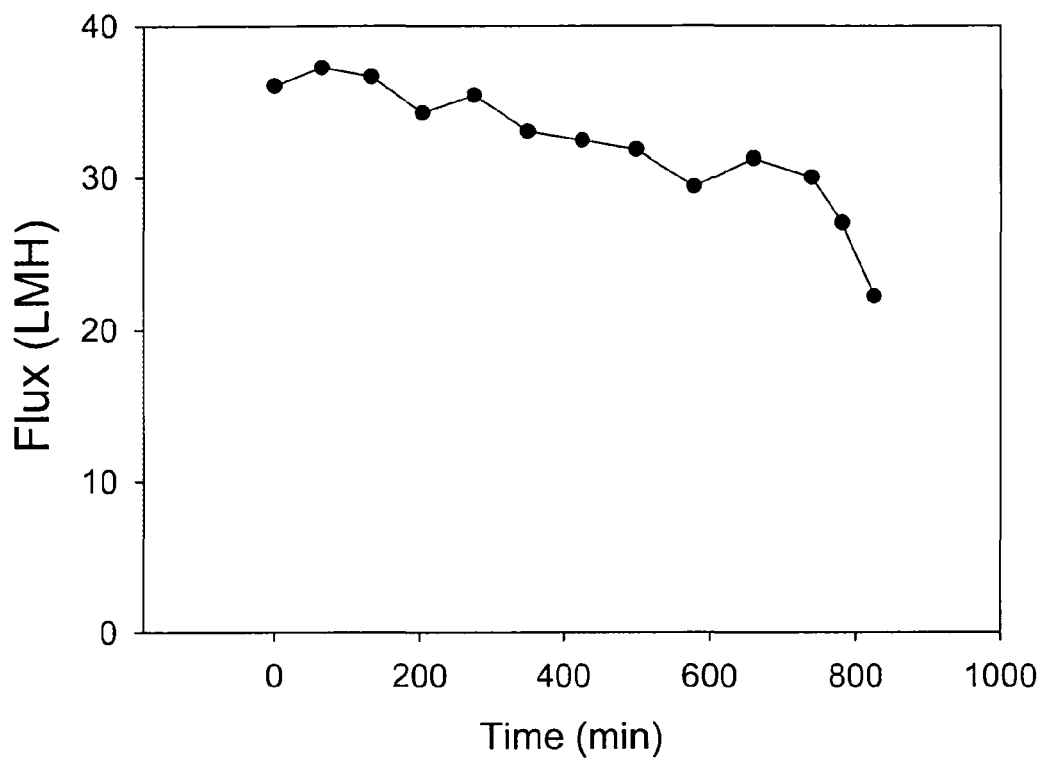
FIG. 1 shows the changes in filtrate flux during 1000 kDa filtration. The total batch volume was 45 liters.

Aspects of the present invention concern methods for preparing a bone protein preparation, wherein the methods are practiced by:

a) demineralizing the bone and extracting the bone matrix with a solvent, such as guanidine hydrochloride, to obtain a bone protein extract, b) filtering the extract with a microfilter with cut-off size sufficient for removing big particles and non-proteinous material but enabling proteins to pass, and c) filtering the flow-through with a cassette ultrafilter having the cut-off size about 5-10 kDa to obtain the bone protein preparation.

In one embodiment the treatment with guanidine hydrochloride solution in step a) may be replaced with treatment with urea solution which is a known equivalent. Generally 4 M guanidine hydrochloride solution may be used.

The term "microfilter" in step b refers to any suitable filter which is sufficient for removing said big particles and non-proteinous material but enabling proteins to pass. This may also be called "clarification" or "pre-filtering" which is done in order to remove for example suspended particles, colloids, macromolecules, cells and cell debris from solution. The molecules of interests will pass the microfilter. Examples of such filters or filtration methods include Normal flow filtration (NFF, Millipore) and Tangential flow filtration (TFF). Said cut-off size in step b) may be in the range of 0.1-10 μm (nominal micron rating), for example about 0.22-0.1 μm, or about 1000 kDa.

In the ultrafiltration step c) even the cut-off range of 1-500 kDa may be useful. The ultrafilter may be a regenerated cellulose filter or polyethersulfone filter.

In one embodiment of the present invention the bone protein preparation is dialyzed, for example with water, to concentrate and to further purify it.

In another embodiment the bone protein preparation is further dialyzed with a citrate solution to promote the proper folding of the proteins.

In still another embodiment the bone is mammalian bone. In still another embodiment the bone is reindeer bone. In still another embodiment the bone is antler bone. In still another embodiment the bone is long bone.

Aspects of the invention also include a bone protein preparation containing, for example, one or more proteins found in the native extract demineralized with HCl, the preparation of which is described herein, including biglycan, thrombin, lamin A/C, vimentin, osteonectin, biglycan, lysyl oxidase, osteonectin, SPP-24 (secreted phosphoprotein), dermatopontin, chondroadherin and/or matrix-Gla protein. At least the following proteins are contemplated to promote, induce, or accelerate osteoinduction: Matrix Gla protein, SPP-24 (secreted phosphoprotein), BMP-2, BMP-7 and/or TGF-beta 1. Accordingly, the bone protein composition may also contain at least one of the following: biglycan, thrombin, lamin A/C, vimentin, chondroadherin, 22K extracellular matrix protein, lysyl oxidase, osteonectin, collagen or dermatopontin in substantial amounts.

In some embodiments the bone protein composition contains at least Matrix Gla protein, biglycan, SPP-24, chondroadherin, 22K extracellular matrix protein, lysyl oxidase, osteonectin, collagen, BMP-2, BMP-7 and/or TGF-beta 1. One or more of the other proteins mentioned herein may be included, as well. The bone protein preparation contains said proteins in substantial amounts, e.g. an amount sufficient to provide a physiological effect, such as osteoinductive effect or activity. Other proteins may also be present in trace amounts, such an amount too low to be seen on a stained SDS-PAGE or to be sequenced, and such proteins are not essential or required for the osteoinductive or accelerating activity of the protein preparation or a composition comprising said protein preparation. Table 14, for example, "The proteins in HCl demineralized native extract," provides guidance as to how to make a bone preparation of the present invention. These preparations may be obtained with the method described above, but any other suitable method may also be used.

In more embodiments, the bone protein preparation is incorporated or impregnated in matrix, such as a porous matrix. The matrix, carrier or scaffold, which words may be used interchangeably, is enhances the activity and therapeutic potential of the bone protein extract at the site of application (e.g., the matrix, carrier or scaffold when added to a bone protein extract allows for a gradual release of active proteins and reduces the migration of these factors.

Desirably, a carrier matrix meets several criteria. The matrix is preferably biocompatible, bioabsorbable, malleable, and sterilizable. Desired materials are structurally strong, immunologically inert, highly osteoconductive and variably biodegradable. Examples of known organic and inorganic matrixes are described by Kirker-Head, C. A.: Potential applications and delivery strategies for bone morphogenic proteins, *Advanced Drug Delivery Reviews* 43 (2000) 65-92, and Moore et al, Synthetic bone graft substitutes, *ANZ J. Surg.* (2001) 71, 354-361, all of which are hereby expressly incorporated by reference in their entireties.

In another embodiment, a bone protein preparation prepared as described herein is incorporated in granules. In still another embodiment, the granules are β-tricalcium phosphate (TCP) granules, or the granules contain β-tricalcium phosphate. In still another embodiment, the granules are calcium sulfate granules, or the granules contain calcium sulfate. In still another embodiment, the granules are hydroxyapatite granules, or the granules contain hydroxyapatite. In another embodiment, the bone protein preparation prepared as described herein, is incorporated in a matrix. In still another embodiment, the bone protein preparation is incorporated in granules in a matrix. In one embodiment, the matrix is polyethylene glycol/glycerol (PEG-GLY) matrix. In a further embodiment, said preparation contains stearic acid. All said embodiments may be applied to any of the applications, methods, or uses described herein.

In still another embodiment the bone protein preparation prepared as described herein is in a form of a lyophilizate.

Some embodiments also include a paste, such as an injectable paste or gel, comprising one or more of the bone protein preparations described herein. The paste may also be mouldable, which form may also be called putty. Accordingly, some embodiments, include a putty comprising one or more of the bone protein preparations, prepared by a method described herein. Similarly, some embodiments include a pellet, disc, block or granule comprising one or more of the bone protein preparations, prepared by a method described herein. In another embodiment, the bone protein preparation is provided as a coating on said pellet, disc, block or granule.

Several embodiments also include an osteogenic device, such as a bone implant, comprising one or more of the bone protein preparations described herein, for example matrix, such as a porous matrix, impregnated or coated with one or more of the bone protein preparations, prepared by a method described herein.

In some embodiments, a bone protein preparation prepared as described herein is used as medicament, for example for treating disorders related to bone, cartilage, tendon or tooth defects wherein regeneration, repair or growth thereof is desired, or other diseases.

Pharmaceutical composition containing said bone protein preparations are also contemplated. Preferably said pharmaceutical compositions contain a therapeutically effective amount of one or more of the bone protein preparations prepared as described herein and a pharmaceutically acceptable vehicle, carrier and/or excipient.

Said pharmaceutical composition may be used for treating disorders related to bone, cartilage, tendon or tooth defects wherein regeneration, repair or growth thereof is desired, or other diseases, such as cancer.

Aspects of the present invention also provide a method for inducing formation of bone, cartilage, tendon, tooth or the like, in vitro or in vivo, wherein said bone, cartilage, tendon, tooth or the like is treated with one or more of the bone protein preparations described herein, or with an osteogenic device or other application form containing thereof.

Additional embodiments include methods for treating disorders related to bone or cartilage defects, wherein regeneration, repair or growth thereof is desired, or other diseases, such as cancer, by administering said isolated bone protein preparation to a patient suffering from said disorders.

"Disorders related to bone, cartilage, tendon or tooth defects" as used herein refers generally to any known disorder wherein bone, cartilage, tendon or periodontal healing or reconstruction, e.g. regeneration, is desired. Non-limiting examples of treatments of disorders related to bone, cartilage, tendon or periodontal defects or diseases or the like are regeneration, repair and growth of bone and periodontal tissue; regeneration, repair and growth of bone in mammals, such as human or any other animal; treatment of abnormalities of bone formation or regeneration; wound healing, ectopic bone induction and healing of segmental bone defects in vertebrates; treatment of skeletal disorders and deformations; repair of large bone defects originating from trauma, excision of tumors or congenital malformations, reconstructing bone stocks worn off by an implanted endoprothesis in revision operations and healing delayed or non-united fractures; repair of bone and cartilage defects such as critical size defects, non-critical size defects, non-union fractures, segmental non-union of fractures; acute fractures, chondral defects, osteochondral defects, subchondral defects; local bone and cartilage formation; defects resulting from degenerative diseases; dental applications such as repair of periodontal tissues, alveolar bone, cementum, tooth root membrane, filling of the tooth root canal and improvement or enhancement of fixation of the dental implant. Examples of such disorders can be found in Ann Rheum Dis, Volume 62, 2003, 73-78: Reddy AH: Cartilage morphogenetic proteins: role in joint development, homoeostasis and regeneration, all of which are hereby expressly incorporated herein by reference in their entireties.

In one embodiment an osteogenic device, such as an implant, is provided containing the bone protein preparation. The osteogenic device may contain a biocompatible matrix, such as a calcium phosphate, carboxy methyl cellulose or collagen matrix or combinations thereof. In one embodiment said calcium phosphate matrix is a hydroxyapatite matrix. Said matrix may provide slow release of the bone protein preparation and/or the appropriate environment for presentation of the bone protein preparation. The osteogenic device may also contain a metal implant surrounded by said biocompatible matrix. One example of said metal is titanium. Some examples of such osteogenic devices are disclosed in WO 98/51354, which hereby expressly incorporated by reference in its entirety.

Non-limiting examples of the different framing materials, carriers or frames for forming e.g. different kinds of osteogenic devices or the like with the protein of the present invention are a medium in the form of powder, sponge, strip, film, gel, web or solution or suspension; semi-solid liquid carrier suitable for intramuscular, intravenous, intramedullary or intra-articular injection; isolated mesenchymal stem cells; any pharmaceutically acceptable vehicle; crusted auto- or allograft; any pharmaceutically acceptable matrix; a material selected from the group comprising hydroxyapatite, collagen, polymers (e.g. polylactic acid, polyglycolic acid), synthetic polymers, hyaluronic acid, α-BSM, calcium phosphate, tricalcium phosphate, aporous ceramic biopolymers, aporous resorbable biopolymers, coral, demineralized bone, bioglass, any biodegradable material and combinations thereof; binding agents selected from the group comprising mannitol, dextrans, white petrolatum, alkyl and methyl celluloses, wetting agents such as sodium salt, fobrin glue, mammalian fibrinogen and thrombin and combinations and admixtures thereof. The osteogenic device may be for example a structurally stable, three dimensional implant in form of a cube, cylinder or block or in the shape of an anatomical form or an injectable form. Examples of osteogenic devices, useful materials and techniques are disclosed in book "Skeletal reconstruction and bioimplantation" (T. Sam Lindholm, 1997, Springer-Verlag, Heidelberg, Germany, which is hereby expressly incorporated by reference in its entirety).

An additional embodiment provides a method for inducing the formation of bone, cartilage, tendon, tooth or the like wherein said bone, cartilage, tendon, tooth or the like is treated with the bone protein preparation, in vitro or in vivo. Still another embodiment provides a method for treating disorders described in the specification comprising administering the bone protein preparation to a patient suffering from said disorders. Said bone protein preparation may be administered as a pharmaceutical composition or as an osteogenic device described above. Further morphogenetic proteins or other useful agents may be administered together with said bone protein preparation, as described above, to enhance the therapeutic effect.

Examples

Optimization and Scale-Up of Tangential Flow Filtration of Bone Protein Extract

The following study is based on the master's thesis "Optimization and scale-up of tangential flow filtration of bone protein extract", Viitanen, M. University of Oulu, 2010, which is hereby expressly incorporated by reference in its entirety.

The purpose of this study was to investigate tangential flow micro- and ultrafiltration of animal bone protein extract. The processes were optimized and based on the results, scaled up into the production scale.

In biopharmaceutical applications the solution containing the desired components is often subjected to fractionation and concentration. Usually these steps are carried out using filtration. Tangential flow filtration is an excellent choice for filtration of large volumes, since the filter does not block up as easily as in traditional dead-end filtration. This is due to the feed flow that is parallel to the membrane, and thus sweeps the particles off.

During this study the process parameters of micro- and ultrafiltration of bone protein extract were optimized to achieve a process that was as effective as possible. Two different membranes and feed channel types were also compared for ultrafiltration purposes. A software for design of experiments and optimization was used to study the effect of process variables.

The results show that the animal bone protein extract can be effectively processed using tangential flow filtration. The protein yield was good, both in micro- and ultrafiltration. Neither of the membrane materials tested possessed significant fouling.

However, there were differences in the maximal filtration fluxes. The processes could be even further optimized. Based on the results obtained, calculations for up-scaling the filtration process to the production scale were done. The calculations show that the process can be carried out in desired time and with reasonable costs.

1 Introduction

Tangential flow filtration is widely used in biopharmaceutical and many other industrial applications, e.g., to concentrate or fractionate proteins by ultrafiltration or to remove microorganisms and cells by microfiltration. In this study microfiltration and ultrafiltration of bone protein extract were evaluated. Tangential flow filtration using cassette filters can be an ideal technique for large-scale processing of an extract made from this type of tissue.

The study started with a feasibility study of both the microfiltration and ultrafiltration steps. Different cassette filters for ultrafiltration were compared. Systematic design and modeling software (MODDE) was used for experimental design. Detailed process parameter optimization was conducted for all tested filters. Finally, calculations for process up-scaling were made based on the results obtained.

Not much published data is available about results of optimization experiments that correspond directly to this study. Most of them cover the ultrafiltration of whey. Typically, this kind of information is generated by companies having filtration as a process step. Therefore, it is not necessarily published. Also, each biological filtration process is unique, with a case-specific solution involving choice of membrane material and other characteristics. Behavior of the system is hard to predict and case-specific optimization is always needed.

2 Tangential Flow Filtration 2.1 Overall Description of Tangential Flow Filtration Filtration can in general be split in two different operational categories. They are normal flow filtration (NFF) and tangential flow filtration (TFF). In NFF the solution flows by means of pressure or even gravity in perpendicular direction to the membrane or depth filter. Particles larger than a certain size will be retained on the membrane surface or inside the meshwork of the depth filter. However, accumulating particles will eventually block the filter. NFF is commonly used for sterile filtration and prefiltration prior to micro- or ultrafiltration.

In contrast to NFF, TFF utilizes the feed flow that is parallel to the membrane. This creates the sweeping effect that prevents the blocking of the membrane by particles. Permeate flow, which means the flow passing the membrane, is generated by pressure. Molecules smaller than the pores of the membrane will go with the permeate and larger ones will concentrate in the retentate stream. Generally, TFF is used for concentrating solutions and/or separating molecules or particles based on their size differences. Separation of molecules through a membrane generally follows a Gaussian distribution over the average size of the pores (cut-off value). In addition to the theoretical size of molecules, also the shape and charge have influence of their passage through the pores (Millipore Corporation 1992). The following section addresses different types of TFF processes, filtration units, membranes and factors having influence on them, with special attention given to ultrafiltration.

2.2. Definition of Membrane Separation Processes

Separation processes can be classified according to the size range of particles to be divided. Commonly used definitions include microfiltration (MF), ultrafiltration (UF), nanofiltration (NF) and reverse osmosis (RO), which has also been referred to as hyperfiltration in older literature. Particle filtration is often used as a pre-filtration step prior to micro- or ultrafiltration in order to remove large solid particles and colloidal materials which may cause blockage of feed channels of subsequent filters. The boundaries between the classes are not exact.

2.2.1 Microfiltration

The membrane pore size cut-off (nominal micron rating) used in most microfiltration applications ranges between 0.1 and 10 μm. Microfiltration is used for separation of suspended particles, colloids and macromolecules from solutions. Microfiltration is widely used, for example, in the chemical and mineral industries, and in water clarification applications. In the biotechnological industry it is often utilized to separate cells and cell debris from the media after the fermentation period. Products can be recombinant proteins, metabolites of the organism, or the cells themselves, as in the cultivation of baker's yeast. MF can also be used as a method for sterile filtration of solutions. In this case, a pore size cut-off of less than 0.45 μm is commonly used, or a cut-off of 0.2 μm can be chosen if complete retention is desired.

2.2.2. Ultrafiltration

Ultrafiltration is an excellent choice for concentrating and fractionating proteins. This method is less harsh for proteins compared to evaporation, and is more economical compared to gel permeation filtration. In UF, the range of separation is between 1 kDa and 500 kDa. Many membrane manufacturers provide UF cassettes with a cut-off up to 1000 kDa, equivalent to about 0.1 μm. Pressure range in UF is typically about 1.5-6.5 bar.

UF is widely used in the biopharmaceutical industry in the downstream purification of monoclonal antibodies and recombinant proteins. The dairy industry was one of the first to widely adopt this technique. Typical applications are found in cheese making and in the fractionation of cheese whey.

3 Aims of the Work

The aims of this work were to examine the suitability of membrane cassette filters for micro- and ultrafiltration of bone protein extract and to optimize the processes in small-scale. The selection of the membrane type was one of the major goals. The work was more focused on ultrafiltration because it is more critical and complex from the optimization point of view. Microfiltration served mainly as a purification step for removal of particles and macromolecules larger than typical proteins. Although categorized as microfiltration in this work, the step was executed using a filter having similar type of membrane as in the filters used for ultrafiltration. However, the filter has so large pore size that the optimization is done as for microfilters.

First, preliminary micro- and ultrafiltration experiments were carried out using one type of filter. Based on the results and experience gained, two new and slightly different ultrafilters were chosen for further studies. A program for experimental design (MODDE) was used to examine different parameters having influence on the ultrafiltration process. In addition to filter type, the studied parameters were temperature, pressure and volumetric feed rate. The filters were exposed to various optimization protocols to find the best setpoints and thus make the large-scale process as economical as possible. Microfiltration process was also optimized with respect to the critical flux. Throughout the study the word flux alone refers to filtrate flux.

Regeneration of the membranes after the cleaning step subsequent to filtration was studied with physical and chemical methods. Based on the results, the cleaning methods were evaluated. Finally, calculations for process scale-up were performed using the data obtained from small-scale experiments.

4 Equipment

Filtration experiments were carried out at the University of Oulu, Kajaani University Consortium's Laboratory of Biotechnology in Sotkamo.

4.1 the Filtration Equipment

4.1.1 Millipore BenchScale Unit

In this study, the Millipore BenchScale unit (Millipore Corp., USA) was used exclusively for pre-filtration purposes and for measurements of filter integrity. The unit has a two-liter feed container, which was considered too small for the planned filtration test batch volumes. A pre-filtration capsule filter was attached to the pump hose.

4.1.2 Millipore ProScale Unit

Filtration experiments were carried out using the Millipore ProScale unit. It has a ten-liter glass feed container. If larger volumes were needed, the solution was siphoned out of an extra container. In this case, the retentate stream was directed into this container to ensure proper mixing of the solution. Heating and cooling of the ProScale unit was achieved by means of circulating hot or cold tap water in the heat exchanger.

4.2 Membranes

All of the membranes used in this study were obtained from Millipore Corp., USA. According to the manufacturer's recommendation, the solution was pre-filtered through at least a 100 μm filter prior to MF and/or UF filtration. An Opticap™ XL capsule filter with Polygard® CR media (Millipore Corp., USA) with 50 μm cut-off was always used. Each capsule filter was used maximum two times. Between the filtrations, the capsules were autoclaved at 121° C. for 20 minutes.

4.2.1 Membrane for Microfiltration

For microfiltrations, the protein solution was filtered through a Pellicon® 2 Biomax® cassette having a molecular weight cut-off (MWCO) value of 1000 kDa. The filtration area was 0.1 m² and the screen type was V. The membrane material was polyethersulfone. Millipore classifies the membrane feed channels as type V, C and A. Type V has the most open feed channel geometry whilst A has the tightest.

4.2.2 Membranes for Ultrafiltration

Three different ultrafiltration cassettes were tested in this study and are listed in Table 1. Preliminary experiments were conducted using a Biomax V-screen type of cassette. The type V was selected because nothing was known about the possible fouling effect or formation of aggregates during filtration in the case of this specific solution. The feed channels of the cassette are the most open in type V cassettes, which accounts for why they do not block up so easily. Cassettes of type C having narrower feed channel diameter were selected for further experiments based on the positive results obtained.

TABLE 1

Cassettes used for ultrafiltration experiments.

| Filter brand | Filter material | MWCO kDa | Filtration area m² | Screen type |
|---|---|---|---|---|
| Biomax | Polyethersulfone | 10 | 0.1 | V |
| Biomax | Polyethersulfone | 10 | 0.1 | C |
| Ultracel | Regenerated cellulose | 10 | 0.1 | C |

5 Experiments

The experiments were carried out at Kajaani University Consortium's Laboratory of Biotechnology in four stages. In the first stage, feasibility tests were conducted to find out how the system behaves overall. The second stage of the experiments included the optimization steps of flux and transmembrane pressure (TMP) for both 1000 kDa and 10 kDa (type V) cassettes.

The third stage employed an experimental design plan created using the modeling and design program "MODDE". The goal was to determine the factors that have the strongest effect on ultrafiltration, including the type of the membrane. The cassettes studied at this point were Biomax and Ultracel type C. In the final stage, both type C 10 kDa cassettes (Biomax and Ultracel) were subjected to flux versus TMP optimization tests.

Before every filtration the cassettes were flushed with reverse osmosis (RO) water so that at least five liters were collected from the permeate side. After that, the system was balanced by circulating one liter of pure four-molar (4 M) GuHCl in the system for ten minutes. The system was then emptied before the protein extract was poured into the feed container. After each filtration the retentate circuit was emptied and flushed with a known volume of 4 M GuHCl prior to cleaning.

5.1 Stage One: Feasibility Tests

Filterability of the pre-filtered protein extract through the 1000 kDa cassette was studied first by filtering one batch of 45 liters. A pump speed of 5 Hz was used. The range of TMP remained between 0.65 and 0.73 bar. Samples for protein analysis were always taken from permeate and retentate streams when 4 liters of permeate had been collected. When 44 liters of permeate were collected, one liter of 4 M GuHCl was added to the feed container. This so-called displacement was used to increase the yield of protein in permeate. The filtration was continued until one more liter of permeate had been collected. Samples were taken also at the end of displacement. The volumetric concentration factor (VCF) of the filtration was 45.

Permeate from the preceding 1000 kDa filtration was subjected to ultrafiltration. Two separate filtrations using 22 l and 23 l batch volumes were conducted. The VCFs applied were 10.5 and 8.5, respectively. A TMP of 0.75-0.78 was obtained by using the pump speed of 12 Hz in both runs. Samples were taken for analysis in that same manner as had been applied following microfiltration.

5.2 Stage Two: Optimization of Flux and TMP for Type V Cassettes 5.2.1 Optimization of Flux and TMP for Microfiltration Cassette For open membranes, like those commonly used in microfiltration, the critical flux is determined in the total recycle mode. In this study, 5 liters of pre-filtered protein extract was circulated in the system using four different feed flow rates. Pump speeds of 5, 7.5, 10 and 12.5 Hz were used to create feed flow rates of about 1.15, 1.66, 2.15 and 2.75 l/min, respectively. Because the filtrate flux was so insignificant in the beginning of the experiment, these values also correspond to initial cross-flow rates. The term cross-flow rate refers to retentate flow rate and is commonly used in the context of flux versus TMP curves. Initially, the permeate choke valve was closed. At a given flow rate the flux was increased slightly by barely opening the valve. The system was allowed to stabilize for 10-20 minutes. Flux and TMP were recorded at 5-minutes intervals. This procedure was continued until the valve was completely open or TMP was no longer linear with flux. In the latter case the critical value for flux (filtrate flux) had been reached.

5.2.2 Optimization of Flux and TMP for Type V Ultrafiltration Cassette

Optimization of parameters for ultrafiltration cassette is different than for microfiltration. In this study flux versus TMP curves were determined for microfiltered extract at two concentrations (VCF 1 and 10) using a couple of different feed flow rates.

In the case of VCF 1 the feed flow rates (and initial cross-flow rates) were 1.15, 1.66, 2.15 and 2.75 l/min. The corresponding pump speeds were 5, 7.5, 10 and 12.5 Hz. In the case of VCF 10 the feed flow rates used were 1.66 and 2.75 l/min, respectively.

Experiments were started by circulating 10 liters of protein extract in the total recycle mode. At each flow rate TMP was progressively raised at 5-10 minute intervals by closing the retentate choke valve. Changes in the flux were recorded. If the slope of the flux versus TMP curve started to decrease, the optimum point of TMP had been reached. After the procedure was carried out with all four cross-flow rates, the protein extract was concentrated to a VCF 10. The procedure described above was then repeated.

5.3 Stage Three: Experimental Design Using MODDE

A systematic design of experiments was created using the modeling and design software MODDE (MODDE 8, Umetrics AB, Umeå, Sweden). All the factors involved in the ultrafiltration process were first summarized in the Ishikawa diagram, also known as the fishbone diagram. The four factors selected for experiments are listed in Table 2. The factors can either be qualitative or quantitative. The value of a quantitative factor can be adjusted. The type of membrane is a typical example of a qualitative factor. Responses measured during the tests were the duration of each filtration and the yield (total protein concentration in concentrated solution).

TABLE 2

Factors selected for the MODDE experiments and their properties.

| Factor | Quantitative/ Qualitative | Controllable | Range |
| --- | --- | --- | --- |
| Pump speed (feed flow rate) | Quantitative | Yes | 3-6 Hz |
| Temperature | Quantitative | Yes | 15-30° C. |
| Retentate choke | Quantitative | Yes | 20-80% |
| Membrane | Qualitative | Yes | A or B |

The whole setup of the tests is presented in Table 3. There were altogether 11 test runs. During the study, the Biomax C membrane was referred to membrane "A" and the Ultracel C membrane as membrane "B". The range of "retentate choke" (20-80%) was defined as the percentage of closure of the retentate choke valve. Pump speeds of 3, 4.5 and 6 Hz created feed flow rates of 730, 1035 and 1350 ml/min, respectively. Temperature between 15 and 30° C. was the fourth selected factor.

Some factors, namely, volume, initial concentration, batch differences and permeate choking were ignored. Differences between batches have found to be unsubstantial (results not shown). Volume and concentration of the protein extract will be constant in the final filtration process. Use of permeate choking would only slow down the process, so there was no reason to study its impact. The operator and the equipment, except for membranes, were considered to have a negligible effect on the result of filtration.

A set of 11 filtrations in randomized order was created using software and selecting "Screening" for objective and linear "Fractional Factorial" for design model. The resolution was IV. The design was then executed using an initial volume of three liters in each filtration. The VCF of 10 was then applied, which stopped the filtration when 2.7 liters of permeate were collected. The time required for filtration was recorded (accuracy of 1 minute) and samples were taken from the permeate and concentrate for the determination of the total protein concentration. The protein profile was also analyzed for some of the runs (see Chapter 5.6.2). Results were evaluated with MODDE using partial least squares methods (PLS). The filtration experiments number 9, 10 and 11 were so called centre point runs. The process was repeated three times using the same setpoints of the factors. In centre point runs the values of the factors are always in the middle of the range of each factor. These repeated runs are used to evaluate the variability of the tests, including the analytical methods.

TABLE 3

Design of the filtration tests generated using the MODDE software.

| Exp No | Exp Name | Run Order | Incl/excl | Pump Hz | Retentate choke valve % | Temp ° C. | Membrane |
|---|---|---|---|---|---|---|---|
| 1 | N1 | 5 | Incl | 3.0 | 20.0 | 15 | A |
| 2 | N2 | 1 | Incl | 6.0 | 20.0 | 15 | B |
| 3 | N3 | 2 | Incl | 3.0 | 80.0 | 15 | B |
| 4 | N4 | 6 | Incl | 6.0 | 80.0 | 15 | A |
| 5 | N5 | 3 | Incl | 3.0 | 20.0 | 30 | B |
| 6 | N6 | 7 | Incl | 6.0 | 20.0 | 30 | A |
| 7 | N7 | 8 | Incl | 3.0 | 80.0 | 30 | A |
| 8 | N8 | 4 | Incl | 6.0 | 80.0 | 30 | B |
| 9 | N9 | 9 | Incl | 4.5 | 50.0 | 22.5 | A |
| 10 | N10 | 11 | Incl | 4.5 | 50.0 | 22.5 | A |
| 11 | N11 | 10 | Incl | 4.5 | 50.0 | 22.5 | A |

5.4 Stage Four: Optimization of Flux and TMP for Type C Ultrafiltration Cassettes Compared to type V cassettes the feed channels in type C cassettes are tighter. Thus, a lower feed flow rate is required to create TMP values equal to type V cassettes. In this study, flux versus TMP curves were determined at two concentrations (VCF 1 and 5). The values of initial feed flow rates for both cassettes and VCFs are presented in Table 4. The Biomax cassette is referred to as membrane A and the Ultracel cassette as membrane B. The experiments were started with 5 liters of protein extract in the total recycle mode. Otherwise, the procedure is the same as described in Chapter 5.2.3. One additional item was the checking of the so-called hysteresis: When the highest point of TMP was reached, TMP was gradually lowered. If the flux returned to its initial value the membrane had not been fouled.

TABLE 4

Selected characteristics for flux versus TMP optimization of type C 10 kDa cassettes.

| Membrane/VCF | Pump/feed flow rate (Hz/l/min) | | | |
|---|---|---|---|---|
| | 3/0.730 | 4/0.945 | 5/1.125 | 6/1.350 |
| A/VCF 1 | | x | x | x |
| A/VCF 5 | | x | | x |
| B/VCF 1 | x | x | x | |
| B/VCF 5 | | x | x | |

5.5 Membrane Cleaning Protocol

After each filtration cycle the membranes were subjected to cleaning. The volume of the cleaning solution was 1 l (10 l/m² membrane area). The solution was circulated in the system and the temperature was adjusted via a heat exchanger. A temperature range of about 35 to 45° C. was used. Sodium hydroxide (NaOH) was used as a cleaning agent in concentration of 0.1 to 0.4 M. The contact time range was 30, 45 or 60 minutes, depending on the case. The system was rinsed with RO water so that a total of 5 to 7 liters were collected from the permeate outlet. After that, the value for normalized water permeability (NWP) was measured as described in Chapter 5.6.4. If necessary, the cleaning was repeated, possibly under harsher conditions.

5.6 Measurements Conducted

The samples for protein concentration and SDS-PAGE analysis were performed at a Finnish company, Oulu. The other measurements were conducted at Kajaani University Consortium's Laboratory of Biotechnology. It must be noted that not all the measurements were necessarily done for each sample.

5.6.1 Protein Concentration

The samples from the feasibility tests (stage one) were analyzed for their protein concentration using NanoDrop 2000 device (Thermo Scientific, USA). The analysis is based on UV-spectrometry. Determination of total protein concentration from all other samples was conducted using Bradford's colorimetric assay (Bradford 1976). The dye reagent used was purchased from Bio-Rad Laboratories, USA and bovine serum albumin (BSA) from MP Biomedicals, USA. BSA was used as the reference protein material for preparing protein concentration standard curves. However, the results varied depending on the test method used. That is why the results obtained from the preliminary tests using NanoDrop were used only for screening purposes.

5.6.2 SDS-PAGE Analysis

Sodium dodecyl sulfate polyacrylamide gel electrophoresis (SDS-PAGE) is a common method for separation of proteins according to their size. The protein profile can be visualized on a gel using a protein-specific dye. In filtration processes SDS-PAGE provides excellent information on how the filtration has succeeded. For example, it can be clearly seen if the filter is functioning according to its nominal molecular weight cut-off value. In this study, SDS-PAGE was performed using Bio-Rad Mini-Protean II device according to the manufacturer's instructions (Bio-Rad Laboratories, USA). The method is based on the system described by Laemmli (1970).

Because GuHCl interrupts SDS-PAGE analysis, the samples from filtration experiments first had to be dialyzed against water. During dialysis most of the proteins in the extract precipitate. That is why the precipitate and the supernatant were lyophilized together after dialysis. A portion of the lyophilized protein material was weighed and dissolved in 6 M urea. The protein concentration was measured using the method of Bradford (1976). The samples for SDS-PAGE were then prepared according to the manufacturer's instructions (Bio-Rad Laboratories, USA). In the case of filtration permeate the amount of lyophilized material was sometimes so minor that weighing was not possible. Instead, they were randomly dissolved in 6 M urea and the protein concentration was then analyzed.

Fifteen micrograms of protein was typically loaded into wells of gels. In the case of permeate samples the amount could be lower. Precision Plus Dual Color Protein Standard (BioRad Laboratories, USA) was used as a molecular weight standard. The electrophoresis was performed using a constant voltage of 200 V and the average time of the run was about 50 minutes.

5.6.3 Flow Rates and Transmembrane Pressure

The Millipore Proscale system was equipped with digital permeate flow meter. The retentate flow rate, or cross-flow rate was measured using a stopwatch and graduated glass cylinder of one or two litres. The unit of the permeate flow rate was kg/min but was measured to be quite close to l/min, also when using 4 M guanidine hydrochloride solutions. The feed flow rate could be calculated by adding together the retentate and permeate flow rates. The transmembrane pressure (TMP) is shown directly in the Proscale system but can also be calculated using Equation (1):

$$TMP(\text{bar}) = \left(\frac{P_{feed} + P_{retentate}}{2}\right) - P_{permeate} \quad (1)$$

where $P_{feed}$ is the feed pressure (bar),
$P_{retentate}$ is the retentate pressure (bar) and
$P_{permeate}$ is the permeate pressure (bar).

5.6.4 Normalized Water Permeability

When a filter is used for the first time, its initial normalized water permeability must be determined. It will be the value to which later measurements are compared. It is wise to always use the same process parameters to determine the NWP. Equation (2) is used for the calculation of NWP:

$$NWP = \frac{Q_{permeate} \cdot F}{TMP \cdot A} \quad (2)$$

where $Q_{permeate}$ is the permeate flow rate (l/h),
A is total filter area (m$^2$),
TMP is the transmembrane pressure (bar) and
F is the temperature correction factor from Appendix 1.

The measurement of NWP was always performed after cleaning and before filtrations. Measuring the NWP is the most straightforward demonstration of cleaning efficiency. The closer it can be restored to its original value the better is the cleaning efficiency.

5.6.5 Integrity of filter

To confirm the integrity of filters a specific air flow test must be performed regularly. The filter module was attached to the Millipore Benchscale system and the test was done according to the procedure provided by the manufacturer (Millipore Corporation 1998). Briefly, the cleaned and wetted filter module was attached to regulated gas (air or nitrogen) supply. Gas was passed in from the feed side of the filter at a membrane-specific pressure. A plastic tube was connected to the permeate outlet. The other end of the tube was led into an inverted graduated glass cylinder full of water. This cylinder was placed into a larger container full of water. The air flow rate could be then determined by measuring the volume of air displaced into the glass cylinder in a given time. Each membrane type and size has its own maximum limit of air flow to fulfill the requirements for integrity.

5.6.6 Fouling of Membrane

Typically, the degree of membrane fouling can be calculated using the following Equation (3):

$$\text{Fouling \%} = \frac{Flow_{start} - Flow_{end}}{Flow_{start}} \cdot 100\% \quad (3)$$

where $Flow_{start}$ is the permeate flux at the beginning of the filtration and
$Flow_{end}$ is the permeate flux at the end of the filtration.

One way to calculate membrane fouling is to compare water flow rates before and after filtration prior to cleaning. In this study many of the proteins in the extract precipitate when they come in contact with water. Thus, the fouling percentages calculated do not necessary indicate the fouling which occurred during the filtration. The overall fouling can also be monitored during the filtration to observe the decrease of the flux. The fouling effect can be calculated from the decline of flux during this period using Equation (3).

5.6.7 Mass Balance

In order to understand how proteins are distributed in the process, mass balance calculations are performed. A useful equation for this purpose is Equation (4):

$$\text{Mass balance \%} = \left[\frac{(V_{ret}C_{ret}) + (V_{perm}C_{perm}) + (V_{flush}C_{flush})}{V_{initial}C_{initial}}\right] \cdot 100\% \quad (4)$$

where $V_{ret}$ is the volume of the retentate (l),
$C_{ret}$ is the protein concentration of the retentate (mg/ml or g/l),
$V_{perm}$ is the volume of permeate (l),
$C_{perm}$ is the protein concentration of the permeate (mg/ml or g/l),
$V_{flush}$ is the volume of the solution used for flushing the circuit (l),
$C_{flush}$ is the protein concentration of the solution used for flushing the circuit (mg/ml or g/l),
$V_{initial}$ is the volume of the initial feed solution (l) and
$C_{initial}$ is the protein concentration of the initial feed solution (mg/ml or g/l).

Due to many reasons, the mass balance percentage is seldom 100. Some portion of proteins will be fouled into the membrane. There is always some hold-up volume in the cassette and equipment. Also, the determination methods are not accurate.

6 Results

6.1 Integrities of the Filters

The integrity of all membrane filters analyzed was at the allowed level. Results of the tests are not shown here.

6.2 Feasibility of Cassette Microfiltration

Figure 2:
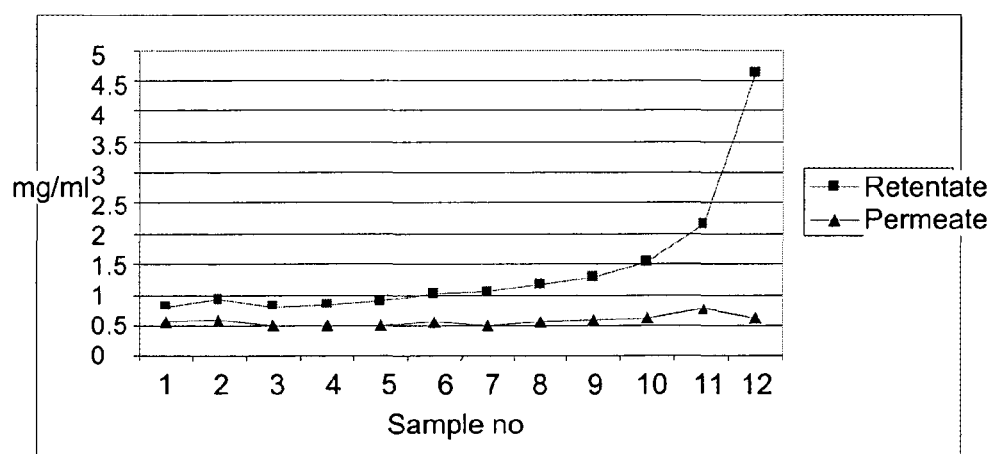
FIG. 2 shows the total protein concentration (mg/ml) in permeate and retentate streams during microfiltration. Sampling was always performed when four liters of permeate was accumulated and at the end point.

The feasibility of the 1000 kDa polyethersulfone cassette filter was studied using 45 liters batch volume and the final VCF of 45. FIG. 1 presents how filtrate flux evolved in the course of the filtration. It can clearly be seen that the flux remains between 36 and 30 LMH most of the time. The drop at the end is probably due to increased concentration polarization. There was a sharp rise in total protein concentration in the retentate stream at the end of filtration (FIG. 2). The concentration in the permeate remained almost constant during the filtration.

6.2.1 Mass Balance in Microfiltration

The mass balance of the microfiltration was determined. The results are summarized in Table 5. The mass balance percentage calculated using Equation (4) was 94, meaning that 6% of protein was in some way missing after the filtration. There is always a certain loss due to the holdup volume of the filter cassette, piping and pump. Some loss probably originates in fouling of the membrane. The holdup volume for cassettes used in this work is in the range of 30 ml. After flushing step the amount of protein in the holdup volume is therefore considered to be negligible.

TABLE 5

Mass balance calculations for 1000 kDa filtration.

| Fraction | Total volume (l) | $C_{protein}$ (mg/ml) | total protein (g) | percentage value (%) |
|---|---|---|---|---|
| Feed | 45 | 0.625 | 28.125 | 100 |
| Permeate | 45 | 0.513 | 23.085 | 82 |
| Concentrate | 0.5 | 3.945 | 1.973 | 7 |
| Flushing | 0.4 | 3.680 | 1.472 | 5 |
| Mass balance % | | | | 94 |

6.3. Feasibility of Cassette Ultrafiltration

Microfiltered batches of 22 and 23 liters were ultrafiltered using type V 10 kDa filter. It took 5 hours to reach VCFs of 10.5 and 8.5, respectively. The two filtrations behaved overall quite similarly which can be seen from the flux rates (FIGS. 3A and B). In both cases the drop in the flux within the first 10 minutes was 6-7%. This is usually caused by concentration polarization and possibly by fouling. When the final VCFs had been reached the fluxes were 72 and 73% (39 and 38.4 LMH) from the initial values of 54 and 52.8 LMH, respectively.

6.3.1 Mass Balances in Ultrafiltrations

The two ultrafiltrations yielded mass balances very close to each other. The mass balance loss percentages were 3 and 5%. Most of the protein could be found in the concentrate (retentate) as seen in Table 6. One striking difference was the protein concentration ($C_{protein}$) in the feeds. The measured concentrations were 0.47 and 0.555 mg/ml although the material was the same. This could be because of variations in the analysis method.

TABLE 6

Mass balance calculations for two 10 kDa filtrations (type V cassette).

| Fraction | Total volume (l) | $C_{protein}$ (mg/ml) | Total protein (g) | Percentage value (%) |
|---|---|---|---|---|
| Feed | 22 | 0.47 | 10.43 | 100 |
| | 23 | 0.555 | 12.77 | 100 |
| Permeate | 19.2 | 0.05 | 0.96 | 9 |
| | 20 | 0.05 | 1.0 | 8 |
| Concentrate | 2.1 | 4.1 | 8.61 | 83 |
| | 2.75 | 3.88 | 10.67 | 84 |
| Flushing | 0.4 | 1.535 | 0.61 | 6 |
| | 0.4 | 1.225 | 0.49 | 4 |
| Total mass balance | | | | 98 |
| | | | | 95 |

6.3.2 SDS-PAGE Analysis of Permeate in Ultrafiltration

The protein profile of the permeate shows excellently how well the membrane fulfills its specifications. The integrity test usually reveals if the membrane has lost its selectivity but SDS-PAGE analysis also shows the details for the intact cassette. FIG. 4 shows the protein profile of the permeate from the 23-liter ultrafiltration. It can be clearly seen that there are no proteins larger than about 13 kDa. This is a very good result for a 10 kDa cut-off cassette.

6.4 Optimization of Flux and TMP for Microfiltration Cassette

Optimization of the flux performance of microfiltration is described in Chapter 5.2.2. The goal was to determine the conditions where the highest stable flux was achieved. Four different cross-flow rates were used. The results are presented in FIGS. 4 and 5.

A common feature of all four cases was the drop in flux in the beginning of the experiments. This is probably due to the fouling effect or concentration polarization. After the first 15 minutes the flux appeared to stabilize. From FIG. 5 one cannot conclude that the critical flux was achieved using the cross-flow rates of 1.15 or 1.66 l/min. However, around the 70 minute time point there was a decrease in flux at constant TMP in both cases. When fully opening the permeate valve in the following stage, the fluxes seemed to be stable.

Figure 6:
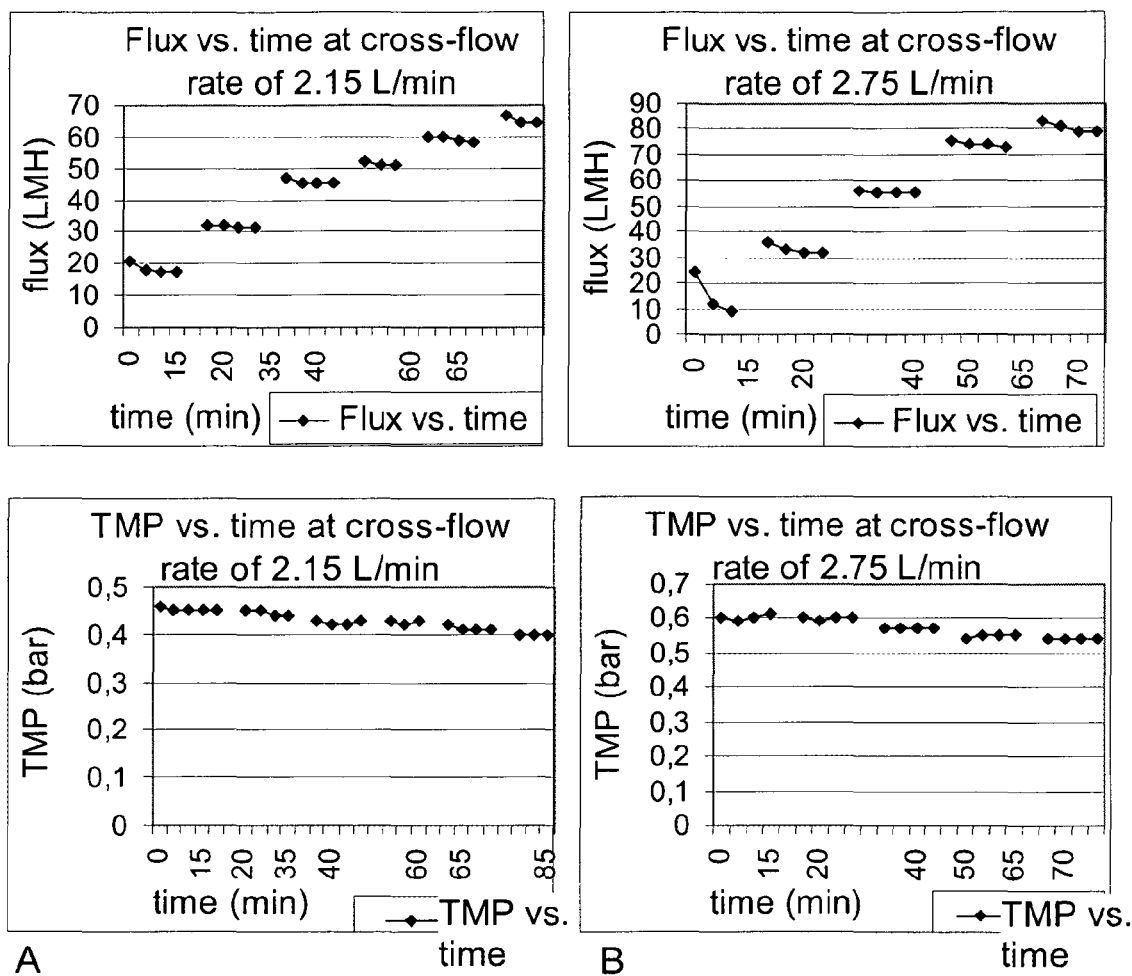
FIG. 6 shows the determination of critical flux for microfiltration though 1000 kDa cassette filter. Flux (up) and TMP (down) at initial cross-flow rates 2.15 l/min (A) and 2.75/min (B).

When cross-flow rates of 2.15 and 2.75 l/min were used (FIG. 6) making conclusions is more complicated. There is a slight decrease in the flux during the first 15 minutes of every stage. However, a more significant decrease could be seen during the last stage in both cases. The critical fluxes could therefore be defined to be around 60-66 LMH when the initial cross-flow rate is 2.15 l/min and around 72-78 LMH when the cross-flow rate is 2.75 l/min.

6.5 Optimization of Flux and TMP for Type V Ultrafiltration Cassette

Figure 7:
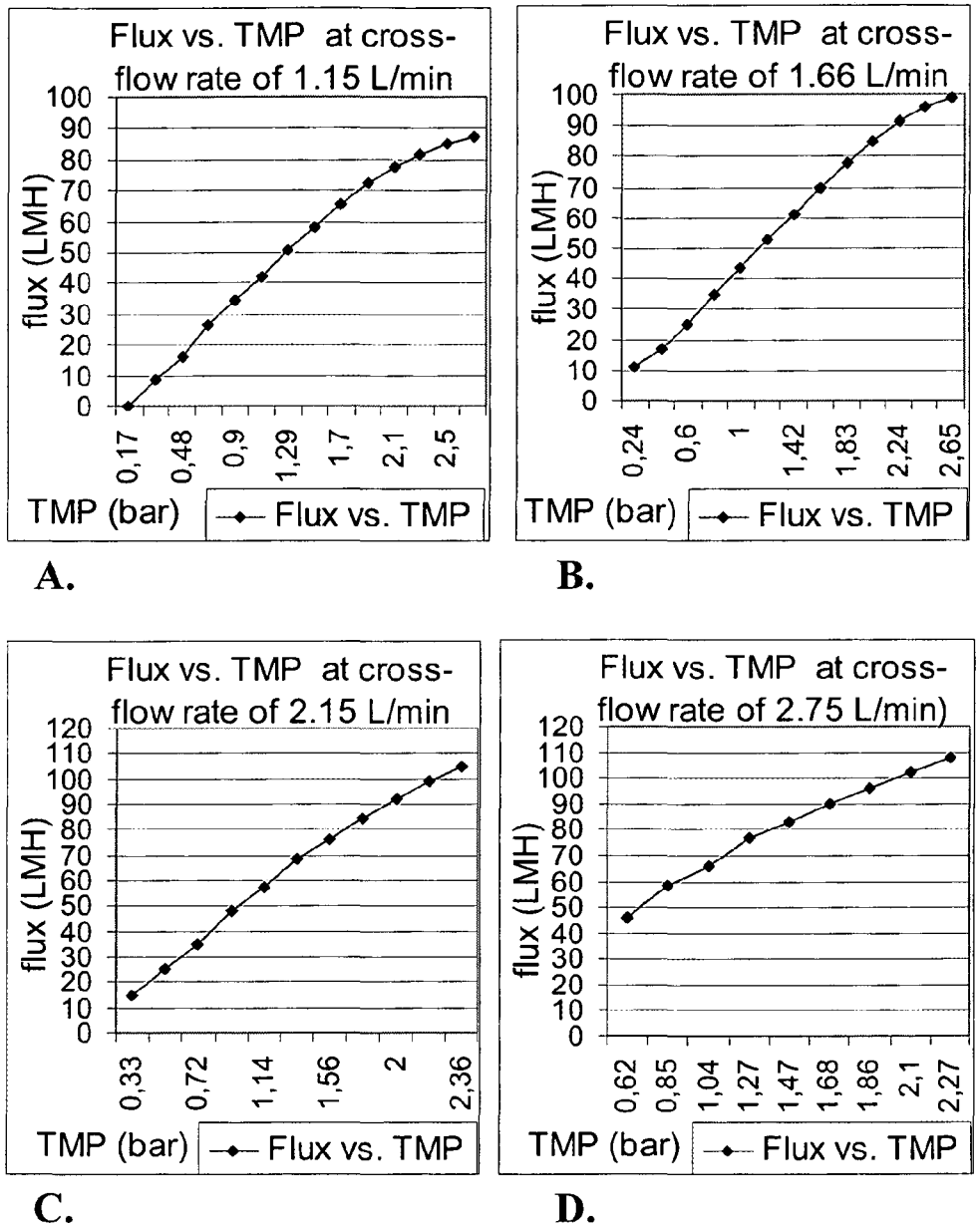
FIG. 7 shows the flux vs. TMP optimization curves in the case of VCF 1 for type V 10 kDa ultrafiltration cassette filter. The initial cross-flow rates used were 1.15 l/min (A), 1.66 l/min (B), 2.15 l/min (C) and 2.75 l/min (D).

As described in Chapter 5.2.2, flux versus TMP was studied using four different cross-flow rates and two VCF values (1 and 10). The curves obtained are presented in FIGS. 7 (VCF 1) and 8 (VCF 10).

When VCF was 1, the slope of the curve started to descend only at cross-flow rates of 1.15 and 1.66 l/min (FIGS. 7A and B). This happened in both cases at a TMP of around 2.5 bar and the corresponding optimal fluxes were about 84 and 96 LMH, respectively. At higher pressure the flushing of the membrane surface may not be sufficient at these two lower cross-flow rates. At higher cross-flow rates (2.15 l/min and 2.75 l/min) the phenomenon was not observed (FIGS. 7C and D). TMP could have been raised more but the feed pressure was already almost 3 bar when TMP was 2.36 bar and 2.27 bar, respectively. The fluxes at these pressures were 105 and 108 LMH and are in the linear range.

Figure 8:
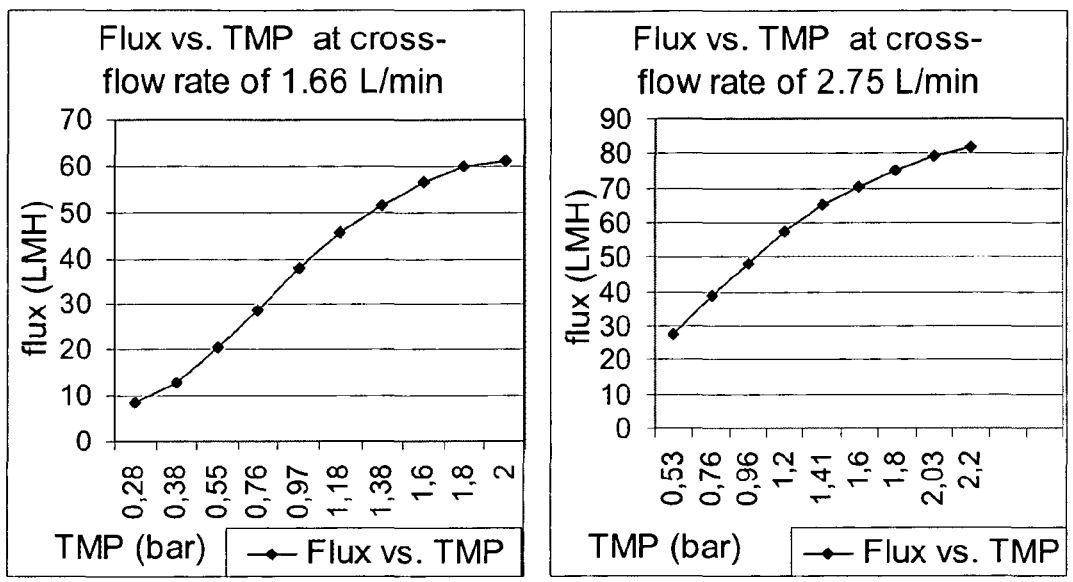
FIG. 8 shows the flux vs. TMP optimization in the case of VCF 10 for type V 10 kDa ultrafiltration cassette filter. The initial cross-flow rates used were 1.66 l/min (A) and 2.75 l/min (B).

Using higher concentration of the protein solution (VCF 10), the descent in the slope was more clearly seen. As shown in FIG. 8A, the optimal TMP is 1.8 bar yielding the flux of 60 LMH at the cross-flow rate of 1.66 l/min. When the cross-flow rate was 2.75 l/min the comparable values are 2 bar for TMP and about 78 LMH for the flux (FIG. 8B). All the results, including the ones for VCF 1 are summarized in Table 7.

TABLE 7

Optimal TMPs and corresponding values of flux for different initial cross-rates and VCFs.

| VCF | Cross-flow rate (l/min) | Optimal TMP (bar) | Flux (LMH) |
|---|---|---|---|
| 1 | 1.15 | 2.5 | 85 |
| 1 | 1.66 | 2.65 | 99 |
| 1 | 2.15 | >2.36 | >105 |
| 1 | 2.75 | >2.27 | >108 |
| 10 | 1.66 | 1.8 | 60 |
| 10 | 2.75 | 2 | 78 |

6.6 Experimental Design Using MODDE

A series of experiments designed using the MODDE software was carried out. It consisted of 11 ultrafiltrations with different compositions of parameters. The measured responses were the duration of concentrating 3 liters of protein extract to VCF 10 and the final protein concentration. The direct results are presented in Table 8. The values of TMP varied depending on the pump speed and retentate choking. The range was 0.5-1.45 bar in the case of membrane A and 0.65-1.85 in the case of membrane B.

TABLE 8

A summary of parameters and responses obtained from ultrafiltration experiments designed using the MODDE software.

| Exp No | Exp Name | Run Order | Incl/excl | Pump Hz | Retentate choke % | Temp ° C. | Membrane | Time min | Conc mg/ml |
|---|---|---|---|---|---|---|---|---|---|
| 1 | N1 | 5 | Incl | 3.0 | 20.0 | 15 | A | 51 | 2.02 |
| 2 | N2 | 1 | Incl | 6.0 | 20.0 | 15 | B | 18 | 2.08 |
| 3 | N3 | 2 | Incl | 3.0 | 80.0 | 15 | B | 30 | 2.2 |
| 4 | N4 | 6 | Incl | 6.0 | 80.0 | 15 | A | 20 | 2.22 |
| 5 | N5 | 3 | Incl | 3.0 | 20.0 | 30 | B | 31 | 2.28 |
| 6 | N6 | 7 | Incl | 6.0 | 20.0 | 30 | A | 25 | 2.24 |
| 7 | N7 | 8 | Incl | 3.0 | 80.0 | 30 | A | 40 | 2.4 |
| 8 | N8 | 4 | Incl | 6.0 | 80.0 | 30 | B | 13 | 1.9 |
| 9 | N9 | 9 | Incl | 4.5 | 50.0 | 22.5 | A | 33 | 2.18 |
| 10 | N10 | 11 | Incl | 4.5 | 50.0 | 22.5 | A | 33 | 2.2 |
| 11 | N11 | 10 | Incl | 4.5 | 50.0 | 22.5 | A | 33 | 2.02 |

6.7.1 Fitting of the Model

Figure 9:
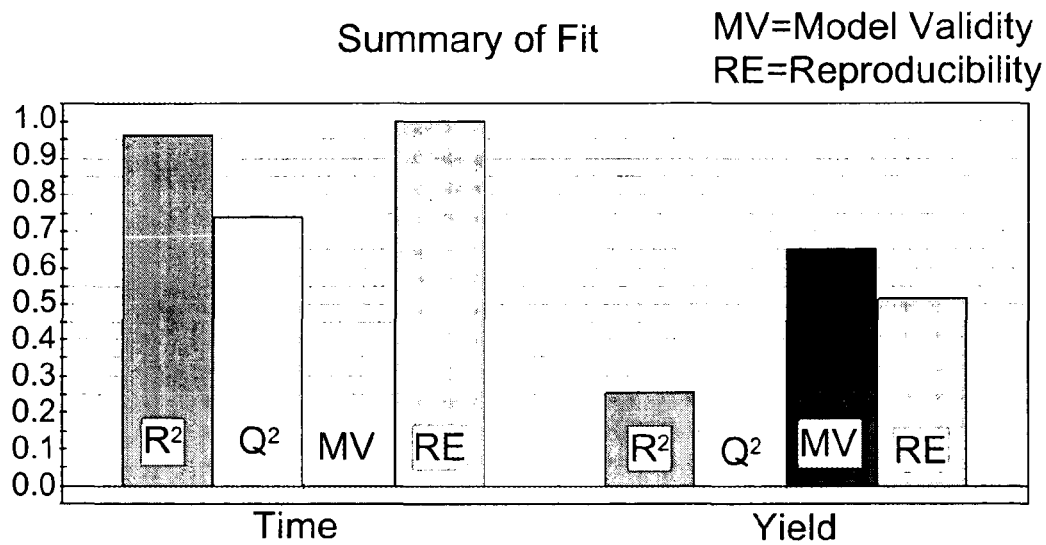
FIG. 9 shows the summary of the model fitted using partial least squares (PLS) method in MODDE. The two responses in the model were time and protein concentration (yield).

The values of the responses (time and protein concentration, or yield) were inserted into MODDE. The model was fitted using the partial least squares method (PLS) and subjected to analysis of variance (ANOVA). FIG. 9 presents the plot called Summary of Fit. For every fitted response there are 4 bars in the plot. According to the MODDE software manual, the values for $R^2$ and $Q^2$ provide the best summary of the model. $R^2$ describes how well the regression model can be made to fit the raw data and is called "goodness of fit". $Q^2$ is referred to as "goodness of prediction" and describes the predictive power of the model. Generally, $R^2$ and $Q^2$ should be high and not separated more than 0.2-0.3. The bar "MV" in FIG. 20 describes the validity of the model. If the value is under 0.25, the error of the model is remarkably larger than the reproducibility shown as bar "RE". (Umetrics AB 2003)

For the Time value, all the evaluative parameters are good except the model validity (FIG. 9). The model validity cannot be calculated because the center point replicate runs gave exactly the same result (100% reproducibility). For yield (protein concentration) the goodness of the model and the prediction are low or zero, meaning that the filtration system is very robust with respect to yield: Changes within the selected parameter range then do not have an influence on the yield.

The ANOVA table for the yield (Table 9) shows that the lack of fit is not significant with a 95% confidence level since p>0.05. As seen also in FIG. 9, there is no model error in respect to the yield. The p-value of regression is 0.730, which is well beyond the critical value 0.05. Regression is then not significant with a 95% confidence level, and the yield cannot be predicted using the model. For the time value, the ANOVA table (Table 10) looks different. The p-value for the lack of fit (model error) could not be determined. All the center point runs namely resulted in the same time values. Therefore, there is no actual error in the model. For the regression the p=0.000 indicating very good model in respect to the filtration time.

TABLE 9

ANOVA table for the Yield. DF is degree of freedom, SS is sum of squares, MS is mean of squares and SD is standard deviation.

| Yield | DS | SS | MS (variance) | F | p | SD |
|---|---|---|---|---|---|---|
| Total | 11 | 51.434 | 4.67582 | | | |
| Constant | 1 | 51.2352 | 51.2352 | | | |
| Total Corrected | 10 | 0.198757 | 0.0198757 | | | 0.140981 |
| Regression | 4 | 0.0506643 | 0.0126661 | 0.513167 | 0.730 | 0.112544 |
| Residual | 6 | 0.148093 | 0.0246822 | | | 0.157106 |
| Lack of Fit (Model error) | 4 | 0.128626 | 0.0321566 | 3.30375 | 0.246 | 0.179322 |
| Pure Error (Replicate error) | 2 | 0.0194667 | 0.00973334 | | | 0.0986577 |

N = 11
DF = 6
Comp. = 2
$Q^2$ = 0.000
$R^2$ = 0.255
$R^2$ Adj = −0.242
Cond. no. = 1.049
Y-miss = 0
RSD = 0.1571

TABLE 10

ANOVA table for the Time. DF is degree of freedom, SS is sum of squares, MS is mean of squares and SD is standard deviation.

| Time | DS | SS | MS (variance) | F | p | SD |
|---|---|---|---|---|---|---|
| Total | 11 | 10847 | 986.091 | | | |
| Constant | 1 | 9720.82 | 9720.82 | | | |
| Total Corrected | 10 | 1126.18 | 112.618 | | | 10.6122 |
| Regression | 4 | 1079.47 | 269.867 | 34.6618 | 0.000 | 16.4276 |
| Residual | 6 | 46.7143 | 7.78571 | | | 2.79029 |
| Lack of Fit (Model error) | 4 | 46.7143 | 11.6786 | — | — | 3.41739 |
| Pure Error (Replicate error) | 2 | 0 | 0 | | | — |

N = 11
DF = 6
Comp. = 2
$Q^2$ = 0.738
$R^2$ = 0.959
$R^2$ Adj = 0.931
Cond. no. = 1.049
Y-miss = 0
RSD = 2.79

Figure 10:
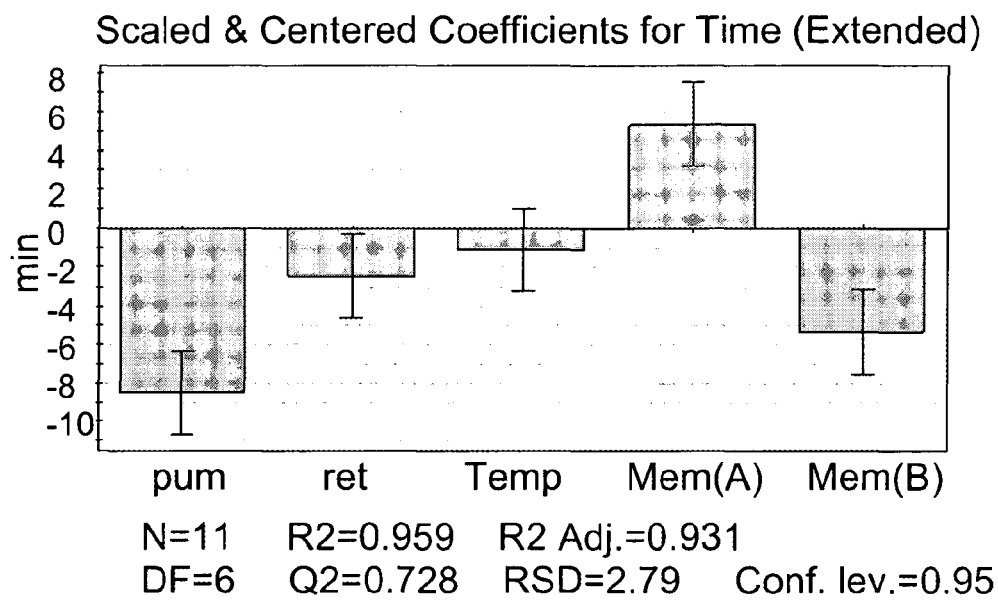
FIG. 10 shows the effect of the studied parameters on duration of ultrafiltrations designed using MODDE software. The shortening "pum" refers to pumping speed, "ret" to retentate choking, "Temp" to filtration temperature, "Mem(A)" to membrane A (Biomax type C, polyethersulfone filter) and "Mem(B)" to membrane B (Ultracel type C, regenerated cellulose filter).

Time was the only response one could affect. FIG. 10 shows how each parameter influenced ultrafiltration time. It can be clearly seen that pump speed (i.e. feed flow rate) has the major effect on the duration of filtration. A higher speed results in faster filtration. Choking the retentate stream has a minor influence. Temperature does not seem to play any role since its error bar is even larger than the actual bar describing the effect. When comparing membranes, it seems obvious that membrane B is a better choice. Selecting membrane B provides over 5 minutes shorter filtration time compared to the average time. For membrane A, the corresponding time is over 5 minutes longer.

Figure 11:
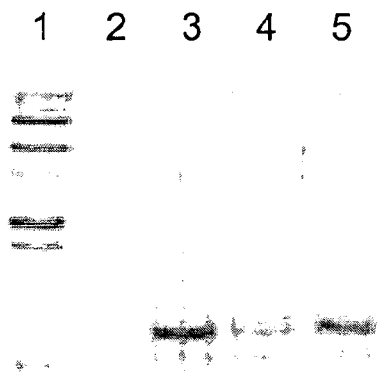
FIG. 11 shows protein profiles of four permeates of ultrafiltrations designed using MODDE software. The SDS-PAGE analysis was done using non-reducing conditions and 200 V constant voltage for 50 minutes. Lane 1: Molecular weight standard, lane 2: Permeate from run 1 (membrane B), lane 3: Permeate from run 4 (membrane B), lane 4: Permeate from run 7 (membrane A) and lane 5: Permeate from run 10 (membrane A). The sizes of the molecular weight standard proteins (lane 1) starting from the top are 250, 150, 100, 75, 50, 37, 25, 20, 15 and 10 kDa.

The quality of the filtration is another important factor. It was studied by taking samples from the permeates and measuring their protein concentration. In all samples the concentration was below 0.05 mg/ml except in the permeate of run 4 where the concentration was 0.06 mg/ml. The protein profile of the four permeates was studied using SDS-PAGE analysis. The profiles are shown in FIG. 11. The permeates from runs 1 and 4 (lanes 2 and 3) were obtained from ultrafiltrations using membrane B and the permeates from runs 7 and 10 (lanes 4 and 5) using membrane A. There are no proteins larger than 13 kDa visible in any of the samples. This means that in all filtrations studied here the membrane functioned according to its theoretical cut-off value. In the case of run 1, hardly any proteins are seen.

6.8 Optimization of Flux Versus TMP for Type C Ultrafiltration Cassettes.

The type C filters had proven to be a good choice for ultrafiltration of the bone protein extract. They provide better turbulence and less shear stress than type V filters that have more open feed channels. Shear is lower with type C filters because the same TMP as for type V filter is obtained with a lower feed flow rate. The optimization of flux versus TMP was studied according to the plan shown in Table 4. In the case of the Biomax filter cassette the results are presented in FIG. 12 for VCF 1 and in FIG. 13 for VCF 5. For the Ultracel filter cassette the corresponding figures are FIG. 14 and FIG. 15. In this study the concentration from VCF of 1 to VCF of 5 was not performed using the highest possible values. Mass balances were determined after the optimization experiments.

6.8.1 Biomax Filter

In the case of VCF 1 the only clear evidence of a decreasing flux was observed at an initial cross-flow rate of 0.945 l/min (FIG. 12A). This and all the other values including the check of hysteresis are summarized in Table 11. At TMP 2.3 bar the flux was about 108 LMH. At higher cross-flow rates no decrease of flux was observed at TMP around 2.8 bar. Higher values were not tested because the feed pressure was already at 3.6 bar due to retentate choking. Thus, at least a flux of 138 LMH can be safely achieved at a cross-flow rate of 1.125 l/min and 132 LMH at 1.350 l/min, respectively.

Figure 13:
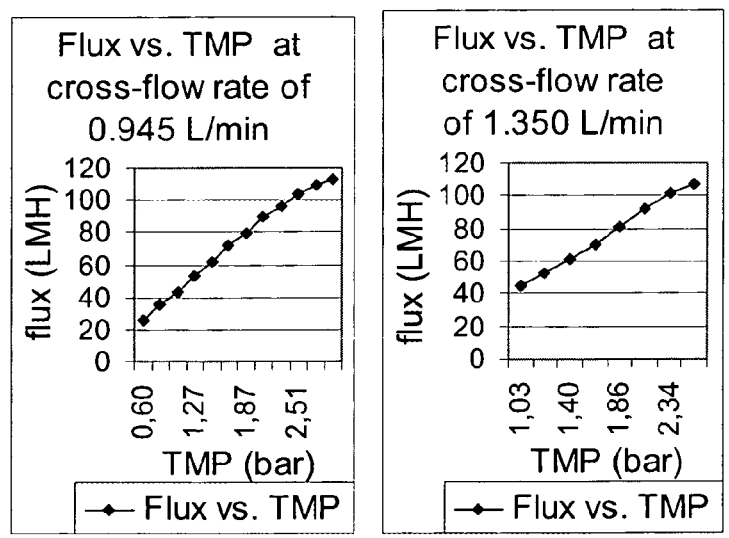
FIG. 13 shows the curves for flux versus TMP optimization for type C Biomax ultrafiltration cassette. The VCF was 5 and initial cross-flow rates 0.945 l/min (A) and 1.350 l/min (B).

When higher concentration (VCF 5) of the protein extract was tested at an initial cross-flow rate of 0.945 l/min there was a slight decrease in flux at high values of TMP (FIG. 13). This may indicate that the critical flux point was near. Again, the experiment was stopped because of high feed pressure. At the highest cross-flow rate (1.350 l/min) the knee point was observed when TMP was 2.5 bar with the flux 108 LMH.

6.8.2 Ultracel Filter

The Ultracel and Biomax filters differ in membrane material. This causes different flow characteristics. How this affects the filtration events is case-specific. In this study using bone protein extract, the equal flow rate of 0.945 l/min led to initial TMP of 1.04 bar and flux of 57 LMH in the case of Ultracel filter compared to initial TMP of 0.62 bar and flux of 30 LMH for the Biomax filter (FIGS. 14B and 12A). In comparison, corresponding values for the type V Biomax filter, even at a higher cross-flow rate (1.15 l/min), were as little as 0.17 bar and practically zero flux (FIG. 7A). This would justify the use of type C Ultracel cassette.

Figure 14:
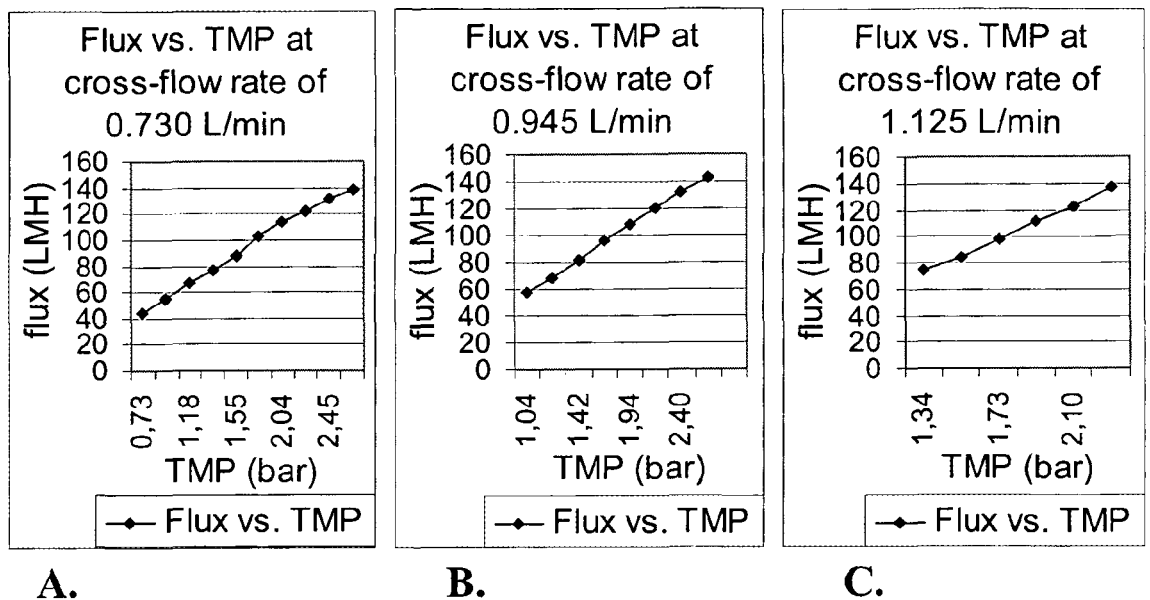
FIG. 14 shows the curves for flux versus TMP optimization for type C Ultracel ultrafiltration cassette. The VCF was 1 and initial cross-flow rates 0.730 l/min (A), 0.945 l/min (B) and 1.125 l/min (C).
Figure 15:
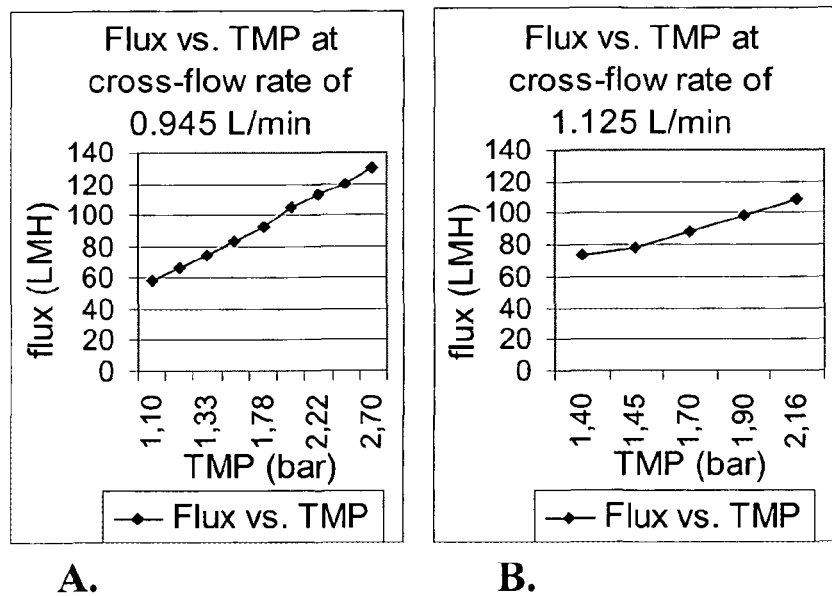
FIG. 15 shows the curves for flux versus TMP optimization for type C Ultracel ultrafiltration cassette. The VCF was 5 and initial cross-flow rates 0.945 l/min (A) and 1.125 l/min (B).

From FIGS. 14 and 15 it can be concluded that at none of the cross-flow rates used in this study the upper limit of TMP and thus maximal flux was reached. This was the case for both VCF 1 and VCF 5. This was due to the limitations in feed pressure, which exceeded 3.6 bar. It appears that the Ultracel filter was not easily fouled even at high pressures and fluxes. The check of hysteresis confirmed this because the initial flux was achieved after the experiments. Table 16 summarizes all the results.

6.8.3 Summary of the Results of Optimization of Ultrafiltration Using Type C Cassettes.

Table 11 summarizes the results obtained during the optimization steps for type C Biomax and Ultracel cassette filters. It is clearly seen that the optimal flux was reached in few cases. Therefore, both membrane types display good performance. As a comparison, the type V Biomax filter had shown a critical flux of 84 LMH at a cross-flow rate of 1.15 l/min, whereas the type C filter's critical flux is more than 138 LMH at an almost equal cross-flow rate.

The results of the hysteresis check indicate that the Biomax membrane is more easily fouled than the Ultracel membrane. Flux rates of the Ultracel filter returned to the initial values in all but one case. For the Biomax filter, the average flux rates were 97% from the initial values which is a good result. However, additional tests should be done before final conclusions are made.

TABLE 11

Summary of the results of flux versus TMP optimization for type C ultrafilters.

| Membrane/VCF | Cross-flow rate (l/min) | Optimal TMP (bar) | Flux (LMH) | Hysteresis (% of initial flux) |
|---|---|---|---|---|
| Biomax/1 | 0.945 | 2.3 | 108 | 100 |
| Biomax/1 | 1.125 | >2.95 | >138 | 92 |
| Biomax/1 | 1.350 | >2.8 | >129 | 99 |
| Biomax/5 | 0.945 | >2.85 | >114 | n.d. |
| Biomax/5 | 1.350 | 2.5 | 108 | 96 |
| Ultracel/1 | 0.730 | >2.7 | >138 | 100 |
| Ultracel/1 | 0.945 | >2.6 | >144 | 100 |
| Ultracel/1 | 1.125 | >2.4 | >138 | 100 |
| Ultracel/5 | 0.945 | >2.7 | >129 | 100 |
| Ultracel/5 | 1.125 | >2.4 | >117 | 98 |

Mass balances of the experiments shown above were calculated and results presented in Table 12. In both cases no detectable amount of protein was found in the permeate. The protein concentrations in flushing and feed solutions were the same. The only difference was found in concentrate which contained 87% of total protein measured from the feed in the case of the Biomax filter. The corresponding value for the Ultracel filter was 95%. This high value resulted in a 6% increase in the final mass balance. However, this single comparison does not reliably indicate that the Ultracel filter provides a higher yield. When calculating the average yields from seven filtrations using the Biomax filter, and four filtrations using the Ultracel filter (Table 8), the results are 2.18 and 2.12 mg/ml, respectively. As already evaluated using the MODDE software, there are no notable discrepancies regarding yield.

TABLE 12

Mass balance calculations of ultrafiltrations using type C Biomax and Ultracel cassette filters.

| Fraction/Membrane | Total volume (l) | $C_{protein}$ (mg/ml) | Total protein (g) | Percentage value (%) |
|---|---|---|---|---|
| Feed/Biomax | 5 | 0.46 | 2.3 | 100 |
| Feed/Ultracel | 5 | 0.46 | 2.3 | 100 |
| Permeate/Biomax | 4 | 0 (<0.05) | 0 | 0 |
| Permeate/Ultracel | 4 | 0 (<0.05) | 0 | 0 |
| Concentrate/Biomax | 1 | 2.01 | 2.01 | 87 |
| Concentrate/Ultracel | 1 | 2.18 | 2.18 | 95 |
| Flushing/Biomax | 0.5 | 0.5 | 0.25 | 11 |
| Flushing/Ultracel | 0.5 | 0.52 | 0.26 | 11 |
| Mass balance/Biomax | | | | 98 |
| Mass balance/Ultracel | | | | 106 |

6.9 Efficiency of the Cleaning of Membranes

Figure 16:
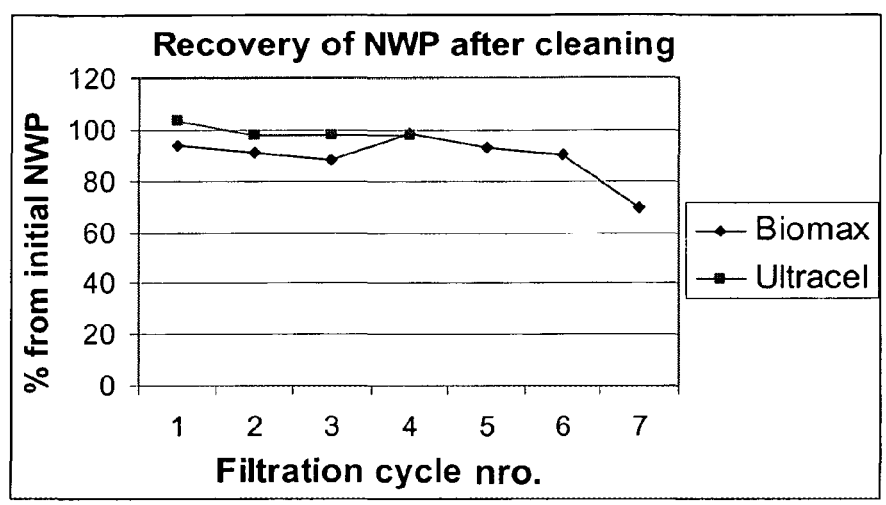
FIG. 16 shows the recovery of NWP of type C Biomax and Ultracel filters after cleaning cycle with 0.1 M NaOH at 37° C. for 30 minutes. The preceding filtrations were done using 3 l feed volume to VCF of 10.

The value of NWP was measured after the cleaning step, performed after each filtration. The results are summarized here. The Biomax membrane seemed to foul easier than the Ultracel membrane. FIG. 16 shows the cleaning efficacy evaluated by NWP values. Seven filtration cycles were done using the Biomax membrane and four using the Ultracel membrane. Filtrations were described in Chapter 5.3. The cleaning experiments were carried out using 0.1 M NaOH for 30 minutes at 37° C. In the case of the Ultracel filter, NWP nearly returned to its initial value in all four cleanings. The Biomax filter showed lower recovery although it was generally over 90%, except after filtration number 7. After the flux vs. TMP optimization experiments (see Chapter 6.8), using these same filters the recovery of NWP was 99% for the Ultracel filter and 72% for the Biomax filter when cleaning was carried out using 0.1 M NaOH for 30 minutes at 37° C. Subsequently, when subjecting the Biomax filter to harsher cleaning with 0.2 M NaOH for 60 minutes at 45° C., the NWP returned to 78% of its initial value. Increasing the concentration of NaOH to 0.3 M and circulating it for 45 minutes at 45° C. provided an NWP value of 80%. This same protocol was found to be required in order to restore the NWP of the type V Biomax ultrafiltration and type V microfiltration cassette to values over 80% (results not shown).

6.10 Up-Scaling of the Filtration Process

Cassette filters are linearly scalable. Therefore, the required membrane area and feed flow rate in the final manufacturing scale can be calculated based on the results obtained in small-scale. In this study the calculations for up-scaling the ultrafiltration process were performed for the type C Biomax and Ultracel filters. The values obtained in the experiments described in Chapter 6.8 were used. The value of VCF was 5. The absolute maximum for filtrate fluxes for the Biomax and Ultracel filters were not reached in those experiments. The highest values shown in Table 11 are used in the up-scaling calculations. Summary of the up-scaling results is shown in Table 13.

6.10.1 Defining the Average Filtrate Flux

The flux usually decreases during the filtration. For scaling purposes an average value is needed. The average filtrate flux $J_f$ can be calculated using Equation (5):

$$J_f = 0.33 \cdot J_{initial} + 0.67 \cdot J_{final} \quad (5)$$

where $J_{initial}$ is the initial filtrate flux (l/m²/h, LMH) and $J_{final}$ is the filtrate flux at the end of the filtration (LMH). Therefore, $J_{initial}$ is the flux when VCF is 1, and $J_{final}$ in this case is the flux for VCF of 5. The highest flux values from Table 11 for both VCFs are used in the calculations using Equation (5). When VCF is 1, those values are 138 LMH for Biomax and 144 LMH for Ultracel. When VCF is 5, the corresponding values are 114 LMH and 129 LMH, respectively. Substituting these values in Equation (5) gives $J_f$ of 121 LMH for Biomax and 134 LMH for Ultracel. If a very robust system is desired, using purely the $J_{final}$ as $J_f$ can be used. It must be noted that, unfortunately, the critical flux for Biomax in the case of VCF of 5 was not tested for the feed rate of 1.125 l/min. The use of this feed rate yielded the highest fluxes when VCF was 1. The value of 114 LMH obtained by the feed rate of 0.945 l/min is used in the calculations which may distort the results to some extent.

6.10.2 Up-Scaling of the Membrane Area

Membrane area required for filtration (concentration) of a certain volume of solution in desired process time can be determined from Equation (6):

$$A = \frac{(V_{filtrate}/J_f)}{t} \quad (6)$$

where $V_{filtrate}$ is the volume of the filtrate to be processed (l),
$J_f$ is the average filtrate flux (LMH) determined in the small-scale and
t is the desired filtration process time (h).

If the volume of the filtrate in the manufacturing scale is 800 L (VCF of 5 from 1000 l batch) and the desired time four hours, the required membrane area A can be calculated using Equation (6). Substituting the values of $J_f$ calculated above will give a membrane area of 1.65 m² for the Biomax membrane and 1.49 m² for the Ultracel membrane. An additional safety factor of 20% for the membrane area is recommended (Millipore 2008). Therefore, the values are 1.98 m² and 1.79 m². In practice this means the use of four 0.5 m² membranes, giving the final membrane area of 2 m². The up-scaled membrane area can also be calculated using Equation (7). The end result is the same as obtained via Equation (6).

$$A_{scaled} = A_{exp} \frac{V_{scaled}}{V_{exp}} \frac{t_{exp}}{t_{scaled}} \quad (7)$$

where $A_{exp}$ is the membrane area used in the experiment (m²),
$V_{scaled}$ is the volume of the large-scale process (l),
$V_{exp}$ is the volume used in the experiment (l),
$t_{scaled}$ is the desired filtration time in the large-scale process (h) and
$t_{exp}$ is the filtration time of the experiment (h).

6.10.3 Calculation of the Feed Rate in Up-Scaled Process

For the large-scale filtration process the feed rate must also be up-scaled. It can be determined from Equation (8):

$$Q_{feed,scaled} = \frac{Q_{feed,exp}}{A_{exp}} A_{scaled} \quad (8)$$

where $Q_{feed, exp}$ is the feed rate used in the experiment (l/min),
$A_{exp}$ is the membrane area used in the experiment (m²) and
$A_{scaled}$ is the membrane area in the large-scale process (m²).

Feed rates used in the small-scale experiments are selected from Table 16. For the highest filtrate flux using the Biomax filter it was 1.125 l/min. For the Ultracel filter it was 0.945 l/min. The membrane area $A_{exp}$ in the experiments was 0.1 m². When inserting the values of up-scaled membrane areas calculated in Chapter 6.10.2 and rounded up to the next higher possible value (2 m² for both membranes) Equation (8) gives $Q_{feed}$, scaled of 22.5 l/min for Biomax and 18.9 l/min for Ultracel. In the final scale filtration equipment, the capacity of the pump should be dimensioned to fulfill these requirements. Otherwise one has to accept an increased in process time.

6.10.4 Summary of the Up-Scaling Results

The theoretical example of the 1000 l batch volume and VCF of 5 was used in the calculations for process up-scale. The full-scale process time was set to 4 hours. Commonly, a time frame of 3-4 hours is recommended (Millipore 2008). Results are summarized in Table 13. The membrane unit prices are starting prices from Millipore Corporation's web pages (www.millipore.com). Linear scalability of the cassette filters allows quick adjustments to the calculations. For example, if the filtration volume is doubled and the filtration time is kept constant, this would require doubling the membrane area. As can be seen in Table 13 the differences between the two membranes are not big in this experiment. The Ultracel filter is a little bit more expensive than the Biomax filter.

TABLE 13

Summary of the up-scaled process factors and membrane costs.

|  | Biomax 10 C membrane | Ultracel 10 C membrane |
|---|---|---|
| Volume $V_{feed}$ (l) | 1000 | 1000 |
| Volume $V_{filtrate}$ (l) | 800 | 800 |
| Filtration time t (h) | 4 | 4 |
| Feed rate $Q_{feed}$ (l/min) | 22.5 | 18.9 |
| Membrane area A (m²) | 2 (1.74) | 2 (1.67) |
| Membrane unit price (eur) for 0.5 m² filter | 2227 | 2498 |
| Number of membrane units needed | 4 | 4 |
| Total membrane cost (eur) | 8908 | 9992 |

7 Discussion

Filtration processes of complex biological materials are always case-specific. Each material has its own protein composition and other elements, and their effects cannot be predicted. In addition, the solution and other conditions also affect the result.

In this study, bone protein extract was subjected to micro- and ultrafiltration and a series of experiments were used to optimize the process as much as possible. No other published study has been found that is directly comparable to this study. This kind of optimization data is typically gathered within the industry and is therefore not necessarily published.

Figure 12:
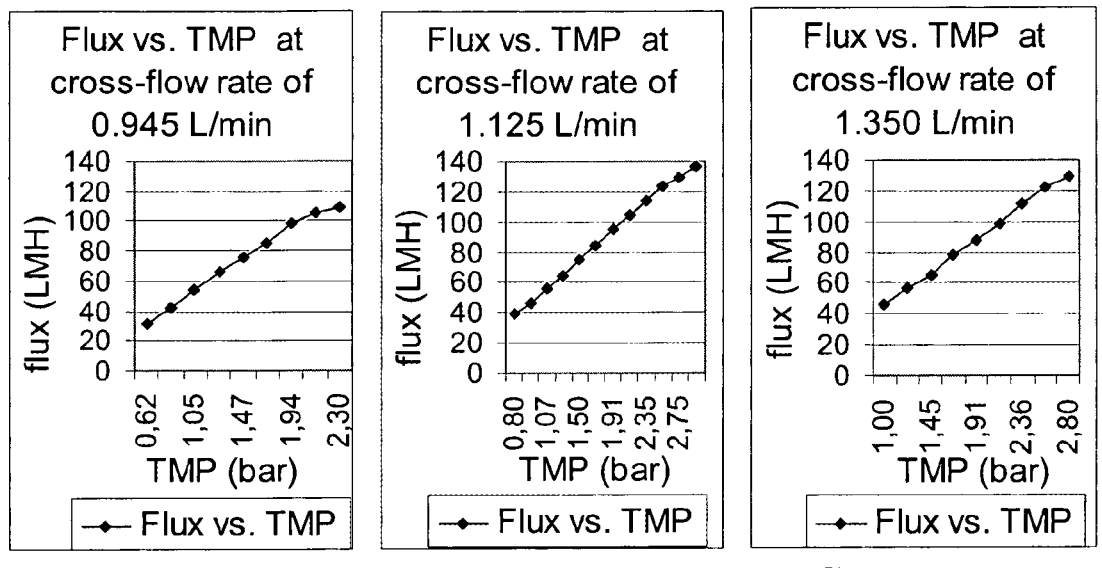
FIG. 12 shows the curves for flux versus TMP optimization for type C Biomax ultrafiltration cassette. The VCF was 1 and initial cross-flow rates 0.945 l/min (A), 1.125 l/min (B) and 1.350 l/min (C).

The first feasibility tests showed that the cassette filters can be applied efficiently for micro- and ultrafiltration of protein extract. No significant decrease in the filtrate flux was observed, either during the micro- or ultrafiltration steps, as shown in FIGS. 12 and 14. The volumetric concentration factor was as high as 45 for microfiltration, and 10 for ultrafiltration. In addition, the mass balance percentages were satisfactory: 94% for microfiltration and 95-98% for ultrafiltration. If the total product mass recovery is less than the initial product mass, it is typically due to adsorption and/or solubility losses during processing (Millipore Corporation 2007). However, the protein analysis method used in this study is not absolutely accurate.

One objective of this study was to select the proper ultrafiltration filter. In the feasibility tests, filters having open feed channel geometry (type V) were used. For this type of filters, a relatively high feed rate was needed in order to provide sufficient flux. Because of this fact and the positive results obtained in the feasibility tests, two ultrafilters, the Biomax and Ultracel, were identified. Both filters possess narrower feed channels (type C). The Biomax is based on a composite polyethersulfone membrane while the Ultracel is a composite of regenerated cellulose. Regenerated cellulose is often selected for biopharmaceutical applications due to its low fouling property.

Both ultrafiltration membranes were compared and other process parameters were screened during eleven different filtration experiments. These experiments were designed using MODDE software. Based on the results, the Ultracel filter appears to give a shorter filtration time. Increasing the feed rate also shortened the filtration time. Surprisingly, choking of the retentate stream did not show a significant effect. However, this was probably due to the fact that the choking valve could not block the stream enough, even when it was 80% closed. This was the maximal value in these experiments. It is obvious that limiting the retentate stream causes the filtrate flux to increase, up to a certain point. The experiment could be re-designed using a higher n-value and leaving out the factors that showed no influence (e.g., temperature) to obtain more exact results. Both of the tested filters showed equal protein yields, so the possible higher fouling of the Biomax membrane is not significant enough to cause detectable loss of proteins.

For the bone protein extract, the critical flux of 138 LMH was achieved under TMP of 2.95 bar using the 10 kDa cut-off polyethersulfone membrane type C (Biomax, Millipore Corporation). In the case of Millipore's 10 kDa cut-off regenerated cellulose type C membrane (Ultracel) the corresponding values were 144 LMH and 2.6 bar, respectively. In both cases the absolute critical value for the flux was not reached due to the feed pressure limitations. For comparison, the type V Biomax yielded a critical flux of 108 LMH at TMP of 2.5 bar.

As was observed during the optimization studies, the type C ultrafilters provided higher fluxes with lower feed flow rates compared to type V filters. Type A filters have the narrowest and most turbulence-promoting feed channels. Therefore, high or even higher fluxes could be obtained with these filters, compared to type C (and type V) filters. This means that the same efficiency can be achieved, but with lower feed rates, or lower operating costs. Less energy is needed for pumping and also the pump shear stress towards the product diminishes. The same kind of additional optimization should be applied for microfiltration. In this study only one type of a microfilter (Biomax type V with 1000 kDa cut-off) was used.

Analyzing the adequacy of the membrane cleaning protocols by means of monitoring the changes in the NWP showed some differences between polyethersulfone membrane (Biomax) and regenerated cellulose membrane (Ultracel). The standard cleaning protocol using one liter of 0.1 M sodium hydroxide at +37° C. for 30 minutes was enough to restore the original NWP. The same protocol was used for the Biomax membrane and was able to restore 90% of the original NWP in most cases (FIG. 16). NWP ±20% of the original typically results in process reproducibility (Millipore 2000). However, in those cases where sufficient NWP was not reached, cleaning with 0.3 M NaOH at +45° C. for 45 minutes was needed to restore 80% of the original NWP. This suggests fouling of the membrane. The Biomax filter may need cleaning with hypochlorite every now and then.

Efficacy of cleaning of Biomax and Ultracel filters after filtration of solution containing 2-25% human serum albumin have been studied (Millipore Corporation 2000). It was shown that cleaning with 0.25 M NaOH at +40° C. for 60 minutes was sufficient for the Ultracel membrane to return NWP values to near-initial levels. A similar effect was obtained for the Biomax membrane using the same solution fortified with 250 ppm sodium hypochlorite. The removal of chlorine from the membrane after cleaning must be verified, which requires an additional analysis step.

Calculations for the up-scaling of the ultrafiltration process, although not being definitive, provide an idea how the scaling-up can be done. The suggested 1000-liter process can be completed within four hours. This is because reasonably high fluxes were obtained with both membranes (Biomax and Ultracel) even compared to fluxes presented in the literature.

8 Conclusions

Cassette filters were found to be suitable for tangential flow micro- and ultrafiltration of bone protein extract. Only one type of filter was subjected to microfiltration studies. The filter used was Biomax which utilizes polyethersulfone as membrane material. The molecular weight cut-off value was 1000 kDa and the screen channel type was V. The critical flux of about 75 LMH was achieved. The results may be improved by introducing a filter possessing tighter feed channels, like type C or A. Alternatively, regenerated cellulose based filters might also be investigated for use in microfiltration. Regenerated cellulose was found to be less susceptible to fouling than polyethersulfone in ultrafiltration.

Ultrafiltration was investigated using three filters having a molecular weight cut-off value of 10 kDa. They were Biomax having a screen channel type of V or C and Ultracel with type C screen channel. The membrane materials were polyethersulfone and regenerated cellulose, respectively. Type C was found to give a better filtrate flux to feed rate ratio. Therefore, the type C Biomax and Ultracel filters were further compared. The critical average flux obtained was 121 LMH for the Biomax and 134 LMH for the Ultracel. The obtained fluxes were not the maximum values for these filters because the flux was increasing linearly with transmembrane pressure in both cases when the feed pressure limit of the equipment was reached. This suggests further testing of type A filters. They do not necessarily yield higher critical average fluxes compared to type C filters, but the fluxes can be achieved by using lower feed rates.

Different parameters having influence on the ultrafiltration process were systematically studied using a software (MODDE) for design and analysis of experiments. The parameters studied in respect of the duration of each filtration and the yield were temperature, feed rate (pump speed), choking of the retentate stream and membrane. No significant differences were observed in yield. The Ultracel membrane gave a faster filtration rate compared to the Biomax filter. Increased feed rate had a similar effect, as expected. The experiment was designed and evaluated with a method that does not take into account the interactions between the parameters. A larger set of experiments would be needed in order to fully investigate possible interactions.

Differences in cleaning were observed between polyethersulfone (Biomax) and regenerated cellulose membranes (Ultracel). Cleaning results were evaluated by comparing the values of NWP. The Ultracel membrane was cleaned efficiently by using 0.1 M NaOH for 30 minutes at +37° C. In many cases, the Biomax membranes required cleaning using 0.3 M NaOH for 45 minutes at 45° C. Based on the literature, polyethersulfone is known to be more susceptible to fouling than regenerated cellulose. This subject could be systematically studied using MODDE. The use of chlorine as an additive for cleaning of polyethersulfone membranes is one way to improve the results. It may shorten the duration of cleaning and lower temperature could also be possible to use. These improvements directly affect the process economy. Cleaning at room temperature could even be tested.

In this study, Pellicon-2® filters manufactured by Millipore Corporation were used. It would be possible to use and test other manufacturers' filters if they had identical outer dimensions. However, none of the data obtained in this study would be applicable to the other filters. The inner geometry of the filters, the membrane and the rating of the molecular weight cut-off values differ between the manufacturers. The results, recommendations and calculations for process up-scaling are therefore valid for only the specific filters evaluated in this study.

9 Summary

The purpose of this work was to study cassette tangential flow filtration of bone protein extract. When further processed, the proteins can be used in orthopedic implants to improve bone growth. Tangential flow filtration has for a long time been used in various industrial applications. In biopharmaceutical applications, cassette filters are often preferred because of their linear scalability, high yield and lot-to-lot manufacturing repeatability.

The theoretical part of this study explored the different designs of filtration equipment, different membrane types and their properties. Cassette ultrafiltration and its use in biopharmaceutical applications was the primary focus of this study. Fouling, cleaning and sanitation of membranes were also addressed.

The experimental part of the study consisted of various filtration experiments, evaluation of cleaning efficacy and performing process up-scaling calculations. The extract was first filtered through a cassette having a molecular weight cut-off value of 1000 kDa. The step was considered as microfiltration, although the membrane format is the same as in ultrafilter. The very open pore size, however, roughly equals to the low end of microfiltration range (0.1 μm). The parameter optimization protocol for open membrane is the same as for microfilters. The permeate of microfiltration was then subjected to ultrafiltration through a cassette having cut-off value of 10 kDa. The parameters affecting the filtrations were studied thoroughly and optimized.

The two filter brands studied for ultrafiltration were Biomax and Ultracel. Biomax consists of a polyethersulfone membrane material while the Ultracel membrane consists of regenerated cellulose. The Biomax exhibited a slightly greater fouling than did the Ultracel filter, however; it also required harsher cleaning conditions. As a result of fouling, the Ultracel yielded slightly higher fluxes and would therefore make a better filter choice for the final process. Absolute critical filtrate fluxes could not be reached in either of the two cases. Further studies are needed, using filters with tighter feed channels, for both micro- and ultrafiltration. Higher filtrate fluxes could then be achieved with lower pressures, improving significantly the process economy.

Calculations for the scaled-up process were based on a 1000-liter batch volume and a VCF of 5. For tested ultrafilters, the process could be completed within four hours using two square meters of total filter area with a cost of around 9000 €. The same filters can often be used for years. Therefore, the membrane cost per batch is moderate. Microfiltration was not optimized as thoroughly as ultrafiltration. Calculations for up-scaling were therefore not performed. However, based on the results obtained so far, the overall cost of the microfiltration step should be within the same range as ultrafiltration costs.

Figure 17:
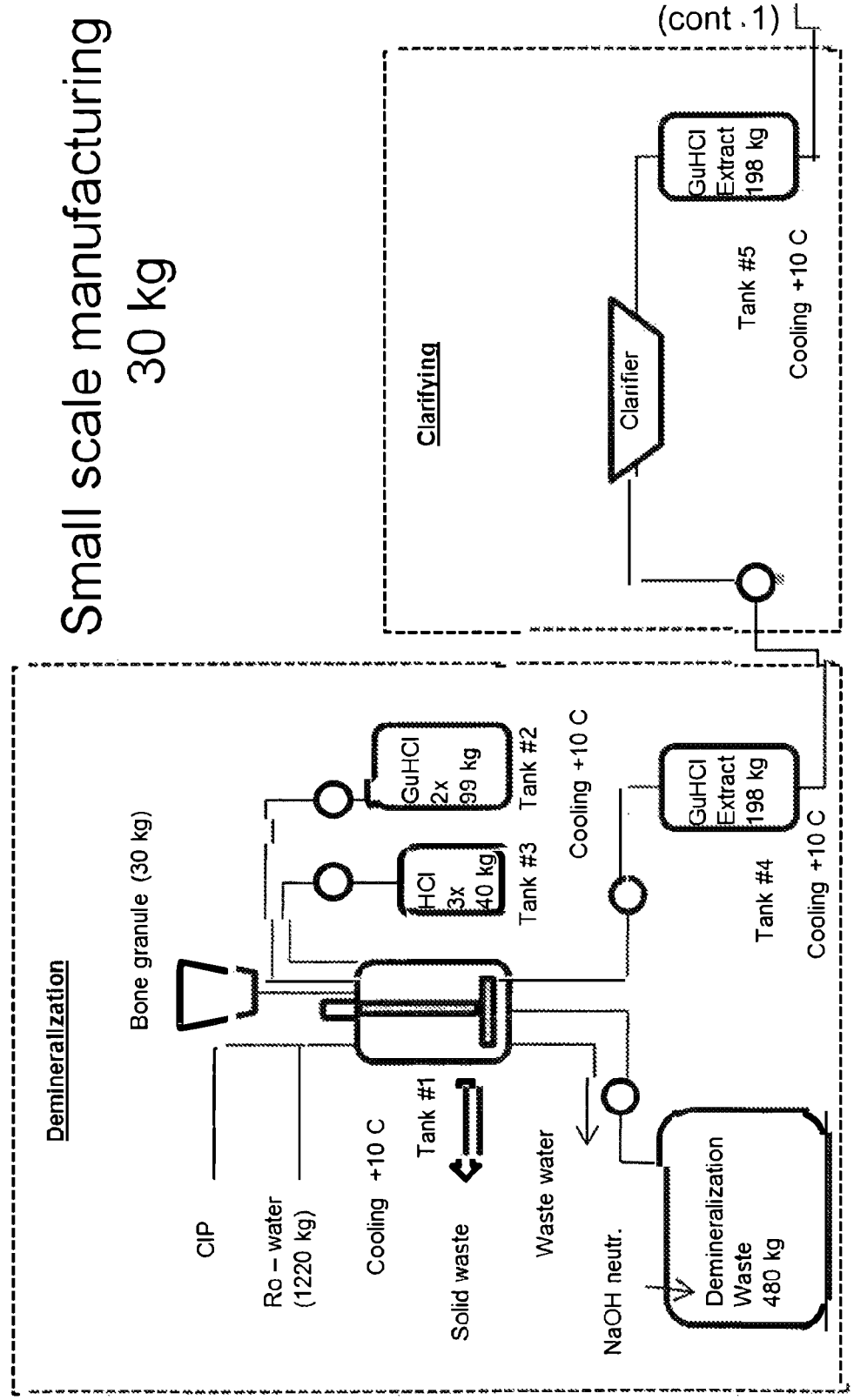
FIG. 17 shows a chart of an exemplary setup in a small scale manufacturing process.
Figure 17:
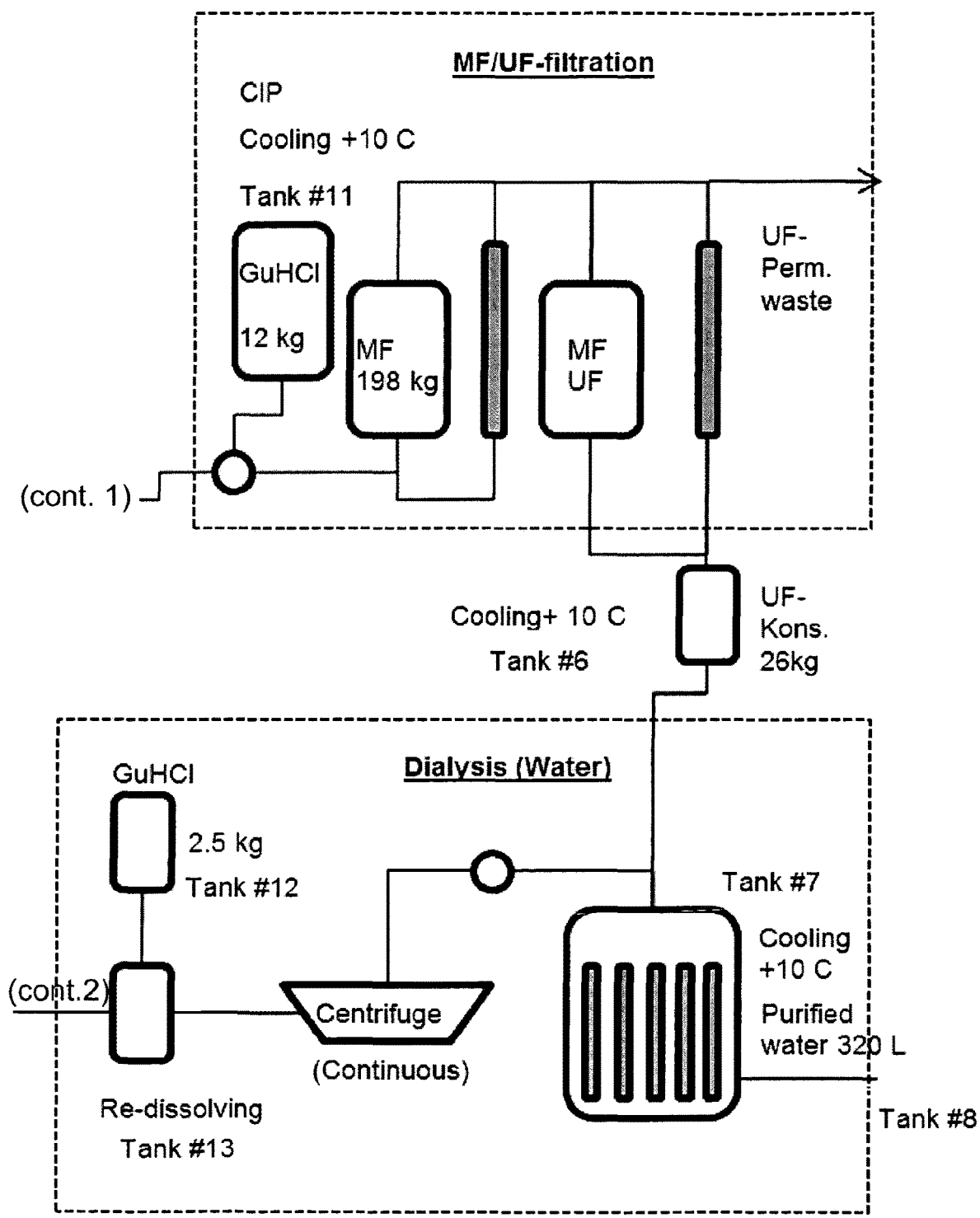
Figure 17:
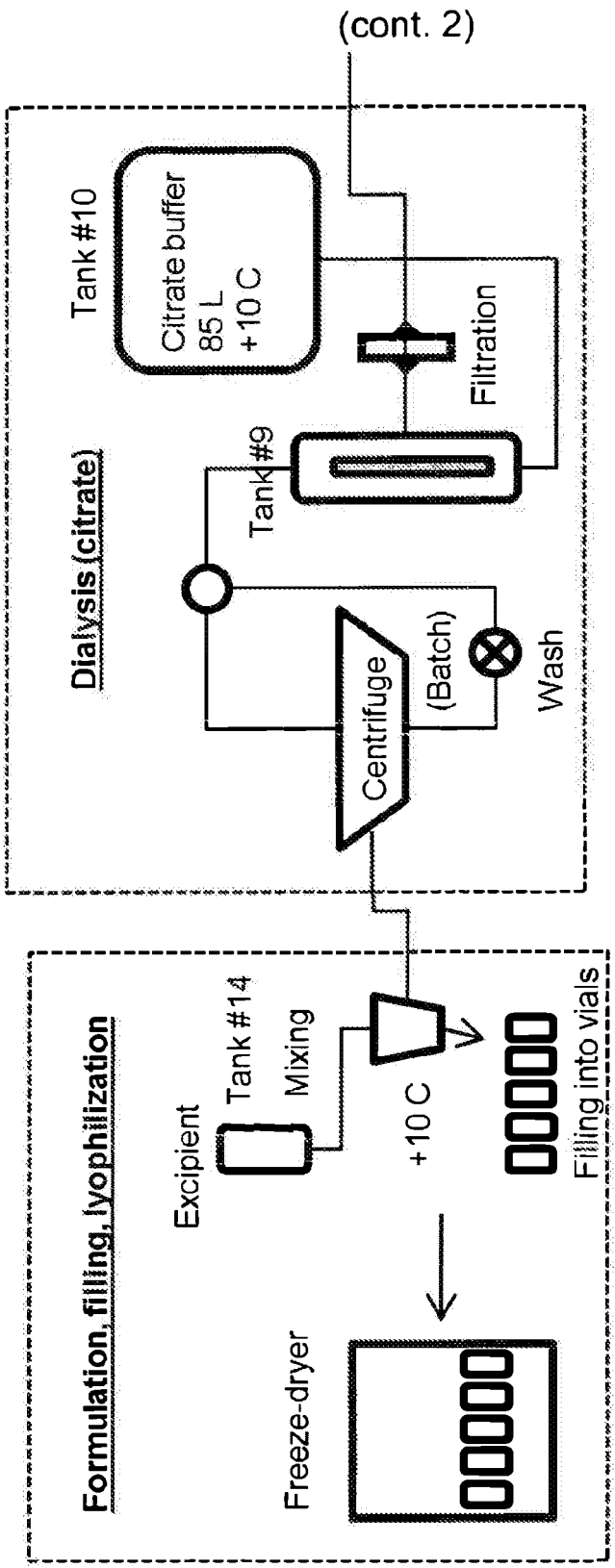
Figure 18:
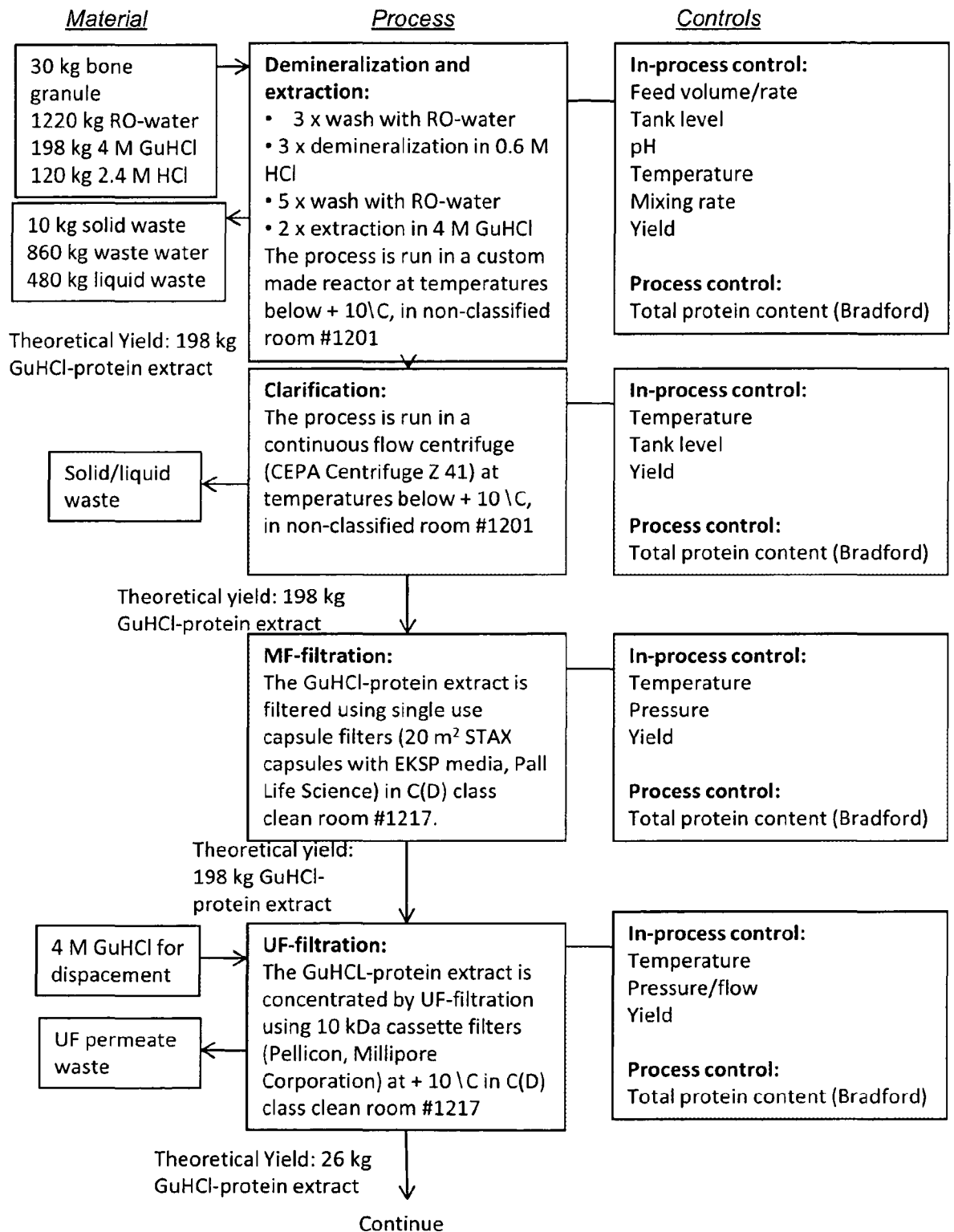
FIG. 18 shows a flowchart of an exemplary process for obtaining the bone protein extract.
Figure 18:
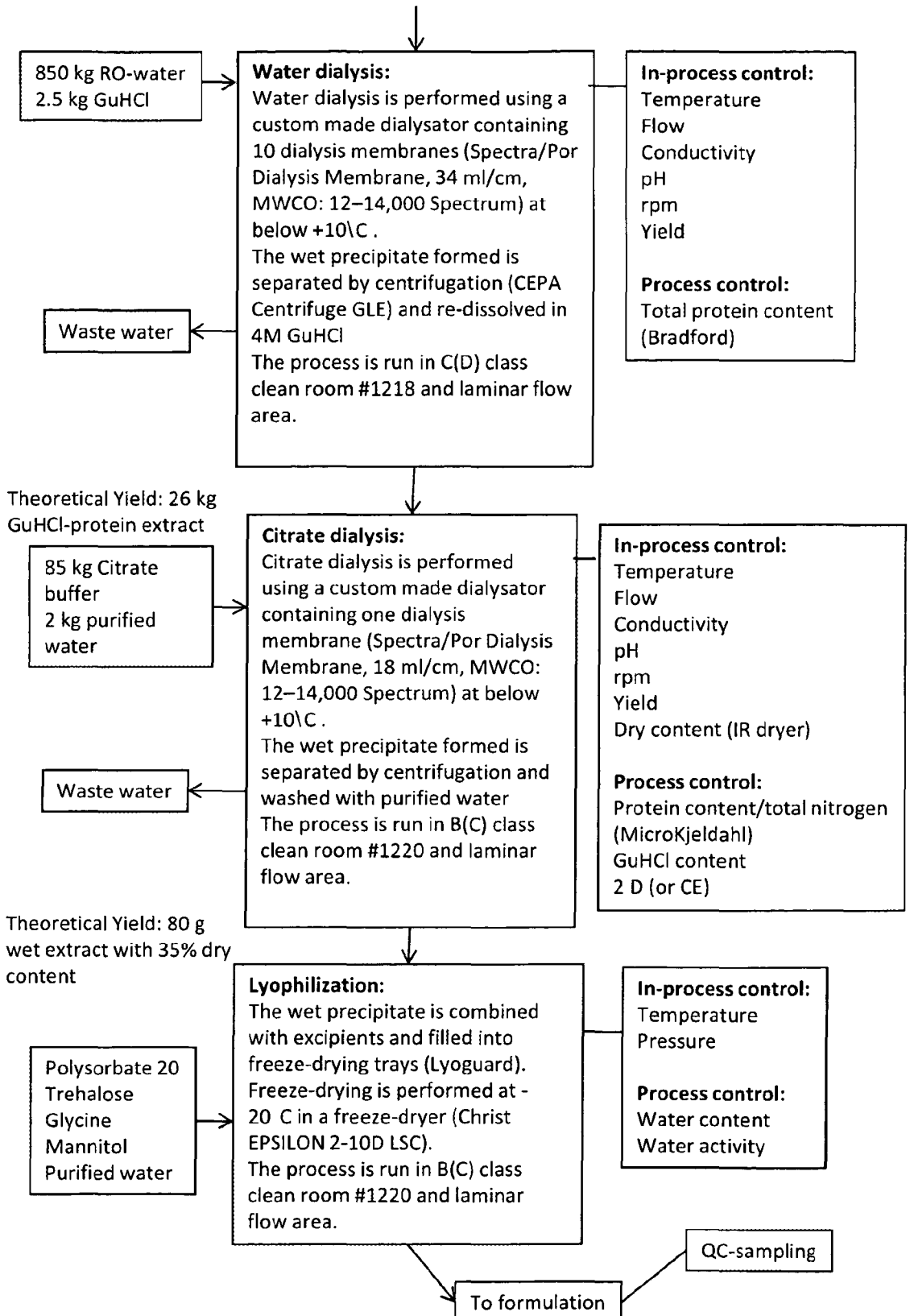
Figure 19:
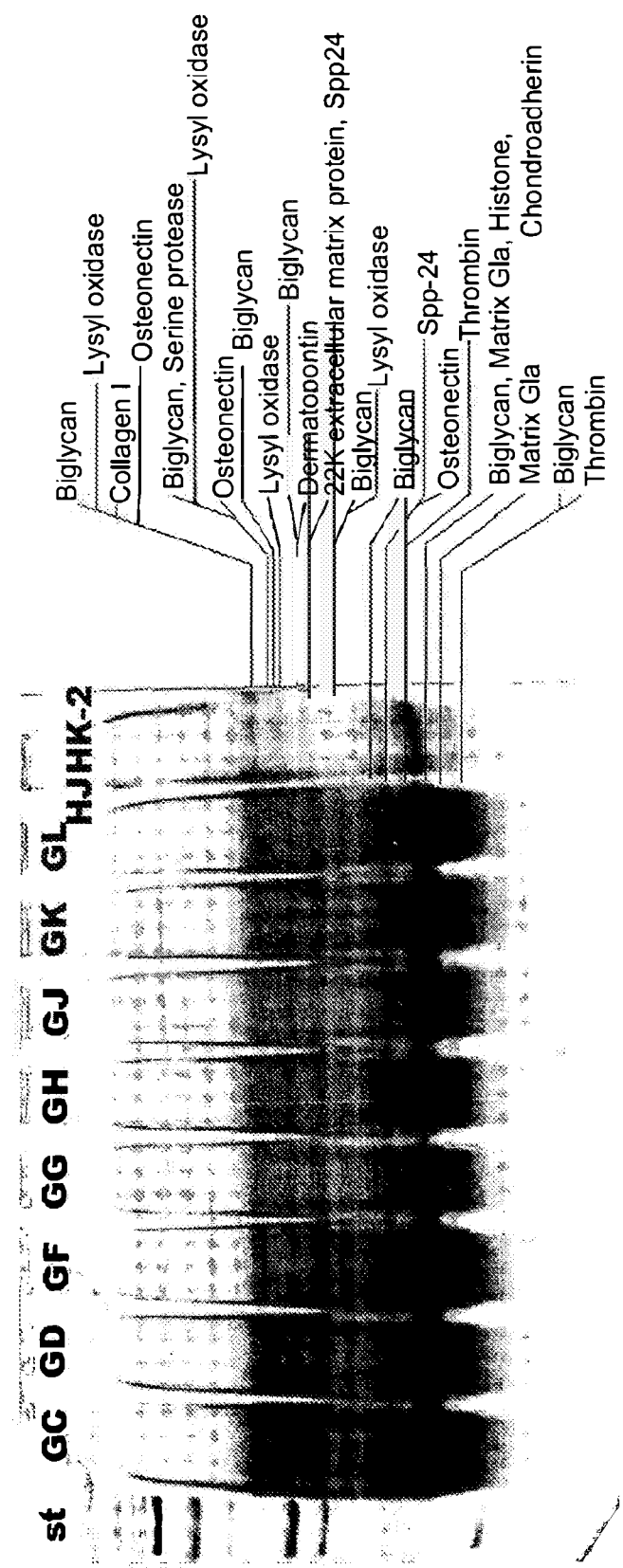
FIG. 19 shows a SDS-PAGE of native extract demineralized with formic acid. The protein bands were isolated from SDS-PAGE and analyzed with MS-MALDI-TOF
Figure 20:
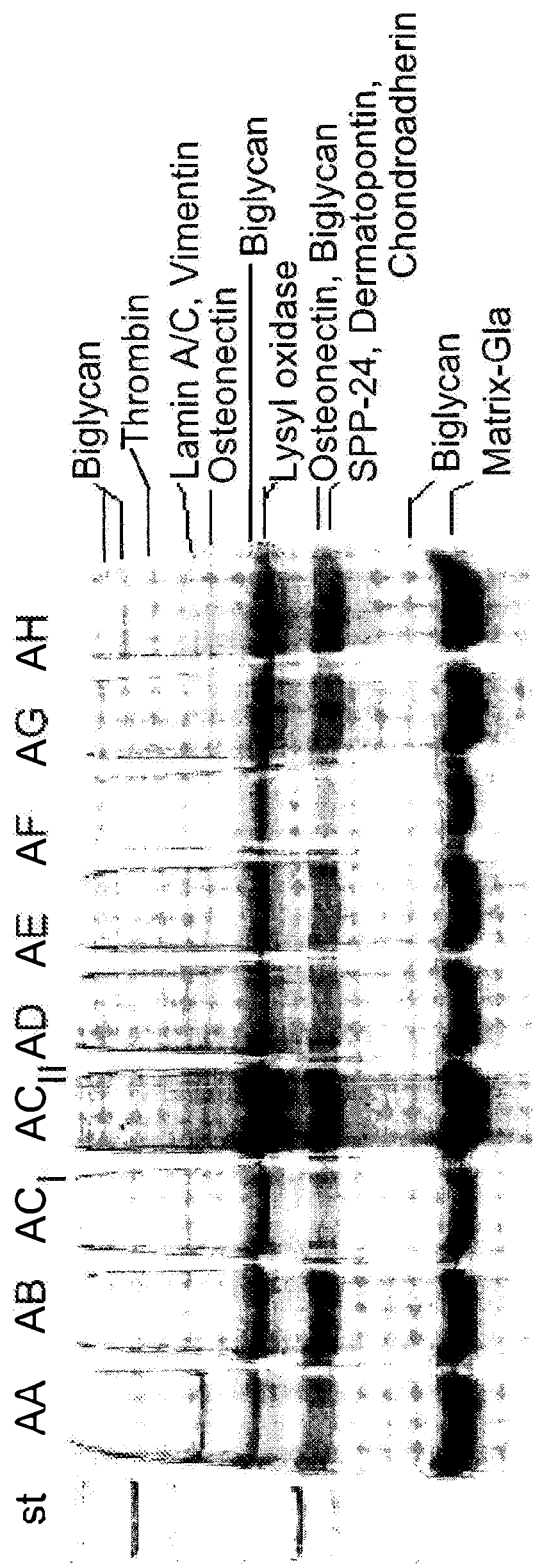
FIG. 20 shows a SDS-PAGE of native extract demineralized with HCl. The protein bands were isolated from SDS-PAGE and analyzed with MS-MALDI-TOF

The following is an exemplary protocol for the extraction of reindeer bone. The different steps described can be applied to other similar protocols separately. Examples of such protocols are also disclosed in FIGS. 17 and 18. FIGS. 19 and 20 shows SDS-PAGEs of native extracts demineralized using either formic acid or HCl.

1. Cleaning and Milling Raw Bone to Bone Granules (all Washing Steps Performed at <10° C.)

1.1. Bones stored at −20° C. are weighed and the epiphyseal bone ends are cut and discarded. The outer surface is high-pressure washed with water.

1.2. Bones are cut with a bone saw to approximately 10 cm lengths and the inner surfaces are washed with high-pressure water. The wash is performed in order to remove marrow and soft tissue.

1.3. After washing, the cleaned cortical bones are frozen in liquid nitrogen for approximately 20 min, and then ground to a particle size of 1.0 $mm^3$ using a HeavyDuty Cutting Mill SM 2000 (Retsch GmbH, Haan, Germany).

1.4. The bone granules are stored at −20° C.

1.5. Sample is taken from every milling batch for a subsequent total viable aerobic count (TVAC).

2. Demineralization of Bone Granules 2.1. About 30 kg of the bone granules are washed three times in cold reverse osmosis (RO)-water (<10° C.) with a mixing time of about 5 minutes per wash. Thereafter the bone granules are demineralized in three steps with dilute 0.6 M HCl.

2.3. In the first demineralization step about 120 kg RO-water, and about 40 kg of 2.4 M hydrochloric acid (HCl), is added to the washed bone granules to achieve HCl concentration of 0.6 M. Rate of the HCl feed is about 2.4 l per minute. The mixing is performed in a custom made container with cooling (BBS Oy, Bioengineering) and continuously stirred. The temperature for this step and all subsequent HCl addition steps is maintained at <10° C. The pH and temperature are monitored continuously.

2.4. After completed HCl feed and after additional 15 minutes mixing, the mixer is stopped and the bone granules are allowed to settle for 20 min. The demineralized water mixture is removed by a peristaltic pump and discharged as wasted.

2.5. The second demineralization is performed identical to the first demineralization step.

2.6. The third demineralization step is performed by adding 120 kg water to the bone granule mixture and then adding about 20 kg of 2.4 M HCl over a period 1 h. The mixing is continued for approximately 16 h until the pH remains constant between 2.8 and 3.0 for at least two hours. The demineralized water mixture is then removed by a peristaltic pump and discharged as waste.

2.7 The demineralized bone is washed five times with about 60 kg of RO-water for 15 minutes. The pH of the water in the last washing step should be between 2.4 and 2.6.

3. Extraction of the Bone Matrix with Guanidine Hydrochloride (GuHCl)

3.1. About 100 kg of 4 M GuHCl (GuHCl, NIGU Chemie GmbH) is added to the demineralized bone and mixed for 22 h in order to extract the bone protein. The demineralized and extracted bone granules are allowed to settle for 20 minutes, after which the GuHCl-protein extract is collected as product. The pH and temperature are measured continuously.

3.2. A second extraction is performed in the same manner, by adding about 100 kg of 4 M GuHCl to the extracted bone and by mixing for 22 h. The GuHCl-protein extract obtained is pooled with the first extraction. The pH is measured and should be between a pH of 3.9 to 4.5.

3.3. The total protein concentration of the GuHCl-protein extract is determined by Bradford method following both the first and second extractions and should be about 0.56 mg/ml±10%.

4. Centrifugation to Remove Solid Phase and Gel Components 4.1. The GuHCl-protein extract is maintained at <10° C. under continuous mixing for 24 h prior to clarification using continuous flow centrifugation (CEPA Zentrifuge Z 41). The separated material is discharged as waste.

5. Filtration 5.1. The obtained GuHCl-protein extract is filtered using single use capsule filters (20 m² STAX capsule with EKSP media, Pall Life Science) or alternatively using 0.2 μm MF-filtration (Pellicon, Millipore Corporation)

5.2. The filtered GuHCl-protein extract is concentrated by UF-filtration at <10° C., using 10 kDa cassette filters (Pellicon, Millipore Corporation).

5.3. At the end of UF-filtration step about 26 kg of UF-concentrate are collected and stored at <10° C. UF-permeate are discharged as waste.

6. Water Dialysis 6.1. The water dialysis is performed using a custom made dialysator equipment (BBS Oy/Bioengineering) containing 10 tubular dialysis membranes. The dialysis membranes (Spectra/Por Dialysis Membrane, 34 ml/cm, MWCO: 12-14,000 Spectrum) are treated with purified water 20 minutes before assembling.

6.2. The dialysis membranes are filled with the concentrated GuHCl-protein extract through aseptic membranes, about 3 l per membrane.

6.3. Parameter settings for water dialysis are: duration 47 h, temperature <10° C., amount of pumped RO-water 16 l/hrs. Conductivity from the inside of the membrane is measured continuously with the final conductivity of 2.2-3.5 mS/cm. The water-insoluble precipitate sinks to the bottom of the membrane during the dialysis.

6.4. The precipitate and the water phase are centrifuged at <10° C. (CEPA Zentrifuge GLE) and the precipitate is collected as we extract. The amount of wet extract is about 160 g.

7. Re-Dissolving and Filtration Before the Citrate Dialysis 7.1. The wet extract is re-dissolved into 4 M GuHCl and mixed with a magnetic stirrer for 16-20 hours. The pH and conductivity are measured. Conductivity is adjusted to 230 mS/cm with 6 M filtered GuHCl. The temperature during mixing is <10° C.

7.2. The re-dissolved extract is vacuum filtered through 0.45 μm (GN-6 sterile, PALL) and 0.2 μm (Supor 200 sterile, PALL) disk filters.

8. Citrate Dialysis 8.1. Citrate dialysis is performed using a custom made dialysator (BBS Oy/Bioengineering)

8.2. Dialysis membrane (4 Spectra/Por Dialysis Membrane, 18 ml/c, MWCO: 12-14,000, Spectrum) is treated with 0.25 M citrate-buffer (pH 3.1) for 20 minutes before assembly.

8.3. Parameter settings for dialysis are 47 h, 9° C., 200 kg 0.25 M citrate buffer, pump capacity 1.6 l/hrs. Conductivity from the inside of the membrane is measured continuously. The final conductivity is usually 9.5-10 mS/cm.

8.4. The citrate-buffer-insoluble material is centrifuged (tube rotor) at <10° C. The clear citrate buffer is decanted to the waste and the precipitate is retained.

9. Precipitate Washing and Lyophilization 9.1. The precipitate is washed three times with WFI-water. Between washes the water is removed by centrifugation.

9.2. The washed precipitate is weighed and samples are taken for analysis. The amount of precipitate is about 80 g with assumed 36% dry content.

9.3. Excipients (polysorbate 20, trehalose, glycine, mannitol) are added to the precipitate as lyoprotectants, and then filled into freeze-drying trays (Lyoguard).

9.4. Freeze-drying (lyophilization) is performed at −20° C. in a freeze-dryer (Christ EPSILON 2-10D LSC).

TABLE 14

The proteins in HCl demineralized native extract

| The sequenced proteins in native extract | Definition | Function |
| --- | --- | --- |
| Thrombin | Coagulation protein | Stimulation of bone resorption |
| Vimentin | Filament protein of the cell | Stabilization of cytoskeleton |
| Vitronectin | Glycoprotein in extracellular matrix | Promotes cell adhesion and spreading, inhibits membrane damaging effects |
| Secreted phosphoprotein 2, 24 kDa (Spp24) | Bone matrix protein, contains TGFβ receptor II homology domain (TRH1) | Osteoinductive degradation product (18.5 kDa) |
| Osteonectin | Calcium binding glycoprotein | Initiates mineralization, bone remodelling |
| Thrombospondin | Extracellular matrix proteins in bone | Bind/activate growth factors, bone regeneration |
| Lysyl oxidase | Extracellular copper enzyme | Collagen and elastin synthesis (cross linking) |
| Chondroadherin | Cartilage matrix protein | Mediates the adhesion of chondrocytes, binds to collagen |
| Biglycan | Leucine-rich repeat proteoglycan (SLRP) | Bone remodeling and mineralization, act together with TGF-β and BMP-4 |
| Dermatopontin (22K extracellular matrix protein) | Extracellular matrix protein with proteoglycan | Regulates the interaction of TGF-beta and decorin, is involved in collagen matrix organization, promotes bone mineralization and inhibits BMP-2 effects on osteoblast precursors. |

TABLE 14-continued

The proteins in HCl demineralized native extract

| The sequenced proteins in native extract | Definition | Function |
| --- | --- | --- |
| Matrix Gla protein | Extracellular calcium binding matrix protein | Inhibits extracellular matrix calcification in arteries and epiphyseal growth plate, regulatory protein for BMP-2 |
| Collagen type I | Fibrous structural protein | Repairs tissue injury, provides strength, integrity and structure |
| Transforming growth factor beta 1(TGFβ-1) | Isoform of TGFβ; growth factor synthesized by skeletal cells | Bone remodeling, controls proliferation and cellular differentiation |
| Lamin A/C (LMNA) | Nuclear lamina proteins | Forms nuclear lamina, factor required for osteoblast differentiation |
| Vitrin | Extracellular matrix protein | Stabilize extracellular matrix |
| PEDF, Pigment epithelium-derived factor | Extracellular glycoprotein | Regulation of cartilage, bone formation and angiogenesis |

20

Evaluation of Various Calcium Salts as Scaffolds for Bone Protein Extract in Bone Substitutes 1. Introduction Native bone contains growth and differentiation factors and signaling molecules, such as bone morphogenetic proteins (BMPs) that are important for bone and cartilage regeneration. These factors and molecules and their specific concentrations are required during the different phases of the entire fracture healing process. Thus, as a treatment of bone fracture, added bone protein extract requires a suitable delivery system, or carrier, to prevent migration from the site of application with a gradual release that results in new bone formation.

An optimal carrier matrix must fulfill several criteria. The matrix should be biocompatible, bioabsorbable, malleable, and sterilizable. Inorganic materials fulfill these requirements because most of them are structurally strong, immunologically inert, highly osteoconductive and variably biodegradable. Calcium salts, as inorganic materials, have been used for years in different variations because the composition of this material is close to that of natural bone composition.

Tricalcium phosphate (TCP) has been shown to be a useful carrier for recombinant human BMPs (rhBMPs) and demineralized bone matrix (DBM). TCP has many positive features for use in in vivo implants, such as the resorption rates closely match the course of normal cancellous bone remodeling and it can bond directly to bone and has a primarily osteoconductive nature. TCP is also more soluble than hydroxyapatite (HAP). HAP is relatively osteoconductive and has high protein-binding capacity. The continuous structure of the HAP design provides a flexibility to achieve high porosity and high surface area, which makes HAP a good candidate for scaffolds. However, HAP is often combined with TCP to form a more resorbable and porous carrier with a greater degree of bone formation. This combination of calcium phosphates has also been used as a carrier for rhBMPs and DBM. Calcium sulfate has been researched as a bone void filler for over one hundred years and has many functions as part of a bone graft composite. The calcium sulfate acts as a binder to improve the total bone contact and the volume surrounding the implant. Pore size is important for bone ingrowth, and increasing the pore size improves the bone healing effects of inorganic materials, such as calcium sulfates. Calcium sulfate has been used as a carrier for DBM for a number of years, and in clinical studies, it has shown excellent biocompatibility.

A mixture of bone morphogenetic proteins (BMPs), growth factors and other bone proteins have been extracted from the bone materials of a variety of animal species, humans and bone tumors. Previous works have demonstrated that reindeer bone protein extract is an effective stimulant for new bone formation in a muscle pouch mouse model. Furthermore, the good healing capacity of the reindeer bone extract in a segmental bone defect was previously demonstrated in the rabbit and rat. The ability of reindeer bone extract to heal various bone traumas is better than that of other extracts, for example, bovine or ostrich extract, which has been explained by the fact that reindeers renew their antlers annually. Furthermore, it has been suggested that more of the protein material extracted from the reindeer bone is in monocomponent form compared with other species, such as bovine, sheep and porcine. Reindeer bone protein extract is similar in composition, method of manufacture, and intended use and application to other animal-derived bone tissue extracts. The closest comparable products are Colloss® and Colloss® E, which are demineralized bone extracts created from bovine and equine bone, and human demineralized bone matrix (DBM) products, such as Osteoset® DBM Pellets.

This study was designed to be an in vivo evaluation of the inorganic scaffolding components to be combined with reindeer bone extract in a heterotopic mouse muscle pouch model of induced ectopic mineralization. Histological and radiographic assessments were used to determine implant responses and the potential formation of ectopic new bone tissue three weeks following implantation.

2. Materials and Methods 2.1. Bone Protein Extract

The bone protein extract was extracted and purified from the diaphyseal bone of the reindeer (Jortikka L, Marttinen A, Lindholm T. S. Partially purified reindeer (Rangifer Tarandus) bone morphogenetic protein has a high bone-forming activity compared with some other artiodactylis. Clin Orthop Relat Res 1993; 297: 33-7). The obtained bone protein extract was freeze-dried at −20° C. degrees using excipients (surfactant (Polysorbat 20, Fluka, Sigma-Aldrich), lyoprotectant (D-(+)-Trehalose Dihydrate, Fluka, Sigma-Aldrich), bulking agent (Glycine, Riedel-de Haen, Sigma-Aldrich) and buffer (D-Mannitol, Fluka, Sigma-Aldrich)).

Figure 22:
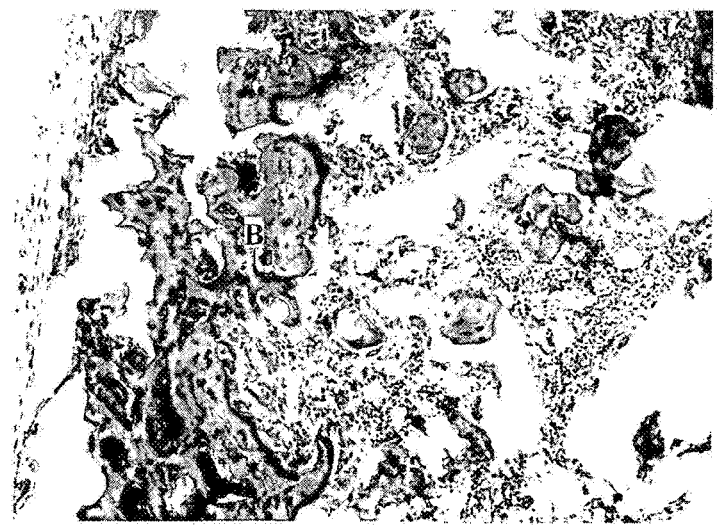
FIG. 22 shows the histological examination that shows the bioactivity and the new bone formation for a 3 mg dose of reindeer bone protein extract in a gelatin capsule in the mouse pouch model. B=bone. (Original magnification 10×).

The protein profile and the bioactivity of the dry bone protein extract were evaluated using the SDS-page and the mouse muscle pouch model study (FIG. 22).

2.2. Scaffold Materials and Study Groups

The used scaffold materials and study groups were a) Porous discs that were 5 mm×3 mm (Berkeley Advanced Biomaterials Inc, USA) with a composition of 30% hydroxyapatite (HAP), 60% tricalcium phosphate (TCP), and 10% calcium sulfate (CS); b) Cem-Ostetic porous discs (Berkeley Advanced Biomaterial Inc., USA) that were 5 mm×3 mm with a composition of 90% TCP and 10% CS; c) Cem-Ostetic® (Berkeley Advanced Biomaterial Inc., USA) powder for putty; d) CS hemihydrate (97%, Sigma-Aldrich) powder for putty; e) Non-porous discs (Berkeley Advanced Biomaterials Inc, USA) with a composition of 60% HAP, 30% TCP and 10% CS; and f) CS dihydrate granules with stearic acid with a composition of stearic acid 50, a mixture of fatty acids that consisted mainly of stearic acid and 40-60% palmitic acid (Fluka, Sigma-Aldrich).

2.3. Sample Preparation

The lyophilized reindeer bone extract (3 mg, BBS-Bioactive Bone Substitutes Ltd, Finland) was reconstituted in 0.9% physiologic saline solution (Natriumchlorid, Fagron, Tamro, Finland) and impregnated into the porous discs (a,b) and the non-porous disc (e), or mixed with the Cem-Ostetic powder (c) and CS hemihydrate (d) to form a moulded disc, or dry mixed with the CS dihydrate granules and stearic acid (f) to form a compressed disc.

The right leg was used as a control with containing the respective carrier and the excipients but excluding the bone extract.

2.4. Animals

A total of 48 mice of the strain BALB/c were used. Animals were supplied from the Laboratory Animal Centre, University of Oulu. Animals were 7-12 weeks in age at the time of the procedure. The study outline included 6 groups with 8 animals per group.

One mouse from group b died on the day of the procedure without any obvious cause. One mouse from group c died on the day of the procedure due to breathing problems. Furthermore, two mice from group d and one mouse from group f were sacrificed two days after the procedure because they had issues walking. Thus, 43 mice survived until the end of the study.

2.5. Surgical Procedure

Surgery was performed under general anesthesia with a blend of fentanylcitrate (80 μg/kg)-fluanisone (2.5 mg/kg) (Hypnorm®, Janssen Pharmaceutica, Inc., Beerse, Belgium) and midazolam (1.25 mg/kg) (Dormicum®, Roche, Basel, Switzerland). Both legs were cleaned, and the eyes of the animals were treated with eye gel to the prevent drying. The mouse was placed on a thermal mattress during the procedure. Transverse skin incisions were made near the spine at the site of the femur. Then, implants were introduced into both thigh muscle pouches in the bilateral hind legs. After the implantation, the muscles were closed with two sutures, and the skin was closed with one suture.

The pain medication post operation consisted of buprenorphine (Temgesic®, Reckitt & Colman Pharmaceuticals, Inc, Richmond, England) at a dose of 0.01-0.05 mg/kg subcutaneously. The animals were allowed full activity in their cages postoperatively. All animals were euthanized 21 days after the procedure, and the hind legs were harvested. The study protocol was approved by the institutional animal experiment and ethical committee.

2.6. Radiographic Evaluation of Bone Formation

Radiographic evaluation (20 kV, 8.00 mAs, 0.32 s/exp, Mamex Dc® ami, Orion Ltd., Soredex) was used to evaluate the formation of new bone and the resorption of the implant. New bone formation and resorption of the implant were evaluated by measuring the opalescent area in $mm^2$ (Osiris 4.19 Digital Imaging Unit, Geneva, software).

2.7. Histological Examination

Two samples from each group were prepared for histology. The specimens were fixed in 10% neutral-buffered formalin, decalcified in EDTA-formalin-solution (pH of 7), processed in a tissue processor, and finally embedded in paraffin. Next, 4.5-μm-thick slices were prepared using a microtome and stained with hematoxylin-eosin.

The quality of new bone and the inflammatory response on the defect site were evaluated by the histological analysis using light microscopy (Nikon Eclipse, E200, Japan).

2.8. Statistical Analysis

Statistical analysis was performed using the SPSS for Windows statistical package (SPSS Inc., version 15.0). The non-parametric Kruskal-Wallis test was used to evaluate the statistical differences between the groups. The Mann-Whitney test was used for pairwise comparison between the active and control groups. Values of $p<0.05$ were considered statistically significant. The results of the radiographic assessment are given as the mean and standard deviations. The differences between the active implants and the controls are shown as percent values.

3. Results

Figure 23A:
FIGS. 23A-F show the histological examination that shows the new bone formation and the implant response in the mouse pouch model using different carriers with the reindeer bone protein extract.
Figure 23B:
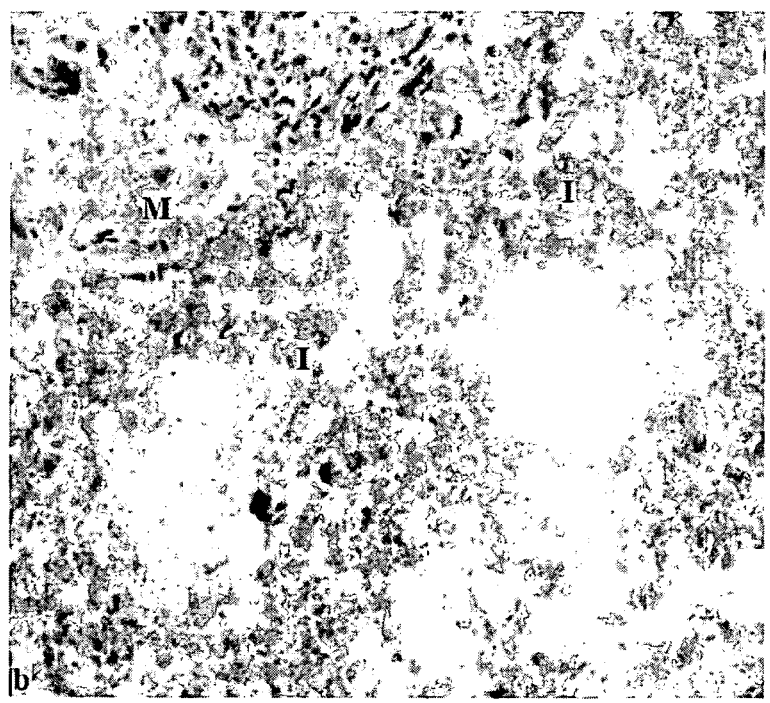

For group a, the radiographic evaluation of the hydroxyapatite-tricalcium phosphatecalcium sulfate discs (HAP:TCP:CS 30:60:10) demonstrated some bone formation outside the active implant; however, the control implants remained intact (Table 15, FIG. 23A). The measurement area was significantly higher for the active implants compared to the controls ($p<0.01$). The harvesting analysis indicated that this new formation was bone-like. The histological evaluation demonstrated that endochondral bone formation occurred in the active sample and not in the control sample (FIG. 23A, 23B).

For group b (TCP:CS 90:10), the radiography evaluation displayed some bone formation outside of the active implants; however, the control implants were nearly intact, and there were no statistically significant differences between the active implants and the controls (Table 15). Visual inspection during harvesting also indicated bone-like formations. The histological evaluation showed endochondral bone formation in the active sample and not in the control sample.

For group c (the Cem-Ostetic), the radiography analysis displayed no new visual bone formation; however, the measurement area was larger in the active group than in the control group ($p<0.01$) (Table 15). Harvesting and histological analysis confirmed that no new bone was found in the samples.

Figure 23C:
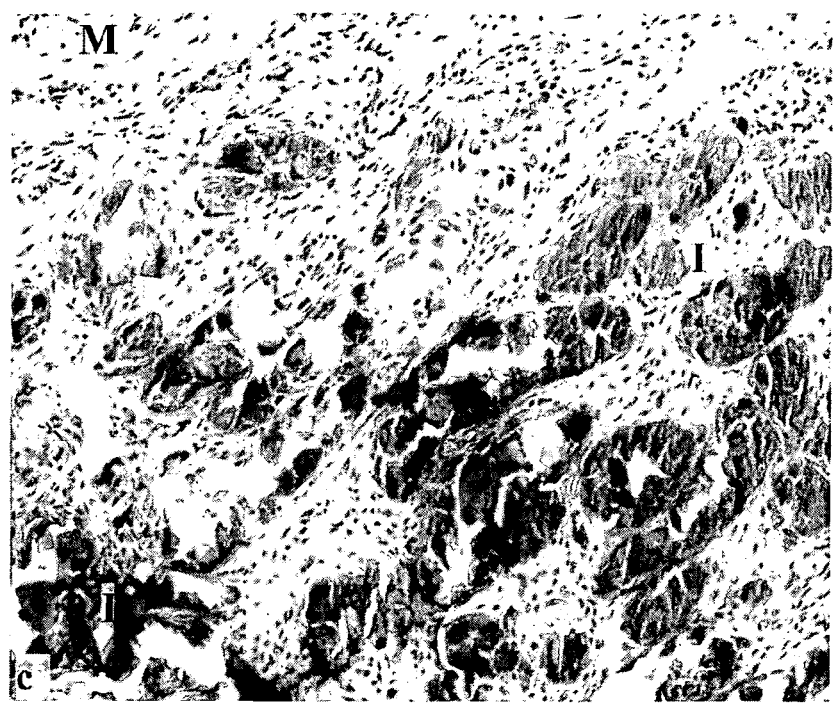
Figure 23D:
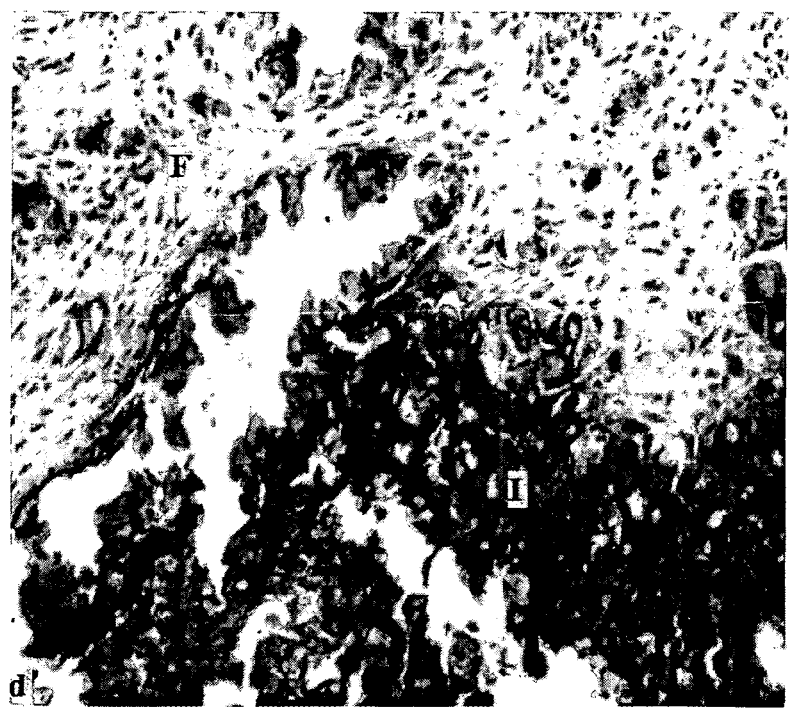
Figure 24A:
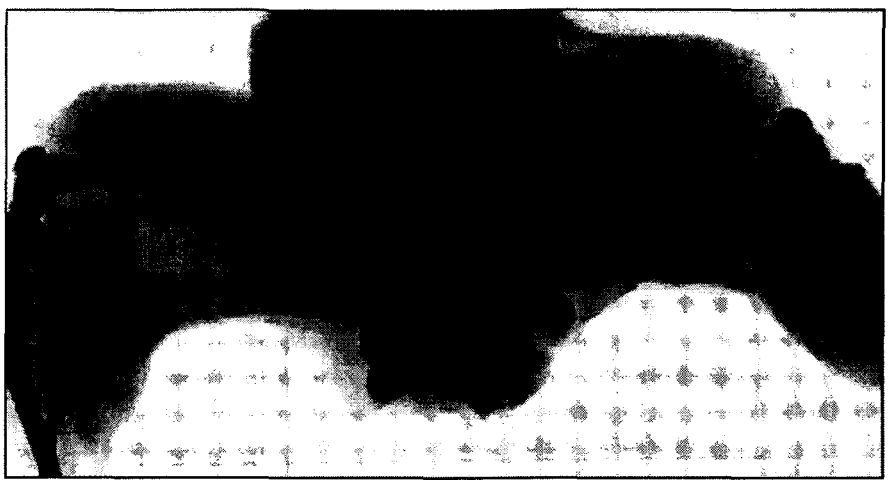
FIGS. 24A-C show the radiographic evaluation of the new bone formation in the mouse pouch model using different carriers with the reindeer bone protein extract. The control without the bone protein extract was located in the right side, and the active implant was located on the left side.
Figure 24B:
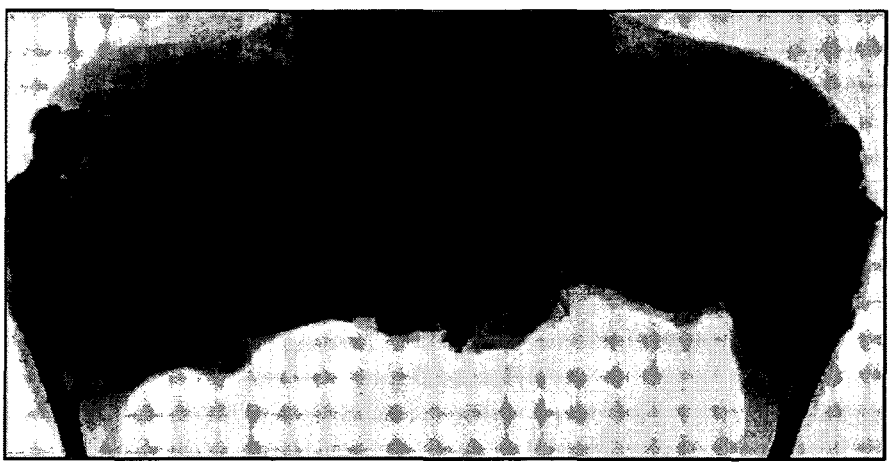

For group d (calcium sulfate hemihydrate discs), the radiography analysis revealed some new bone formation, and significant differences ($p<0.01$) were apparent between the active and control groups (the control group had visibly resorbed) (Table 15, FIG. 24B). However, the harvesting and histological analysis showed that no new bone was found in the samples (FIG. 23C, 22D).

For group e (HAP/TCP/CS 60:30:10), the radiography evaluation showed some bone formation outside of the implant on the active side and some in the control implants (Table 15). Furthermore, the active group had a larger measurement area than the control group ($p=0.001$). The harvesting analysis indicated that this new formation was bone-like. The histological evaluation revealed endochondral bone formation and mature cartilage cells in the active sample; however, none were found in the control sample.

Figure 23E:
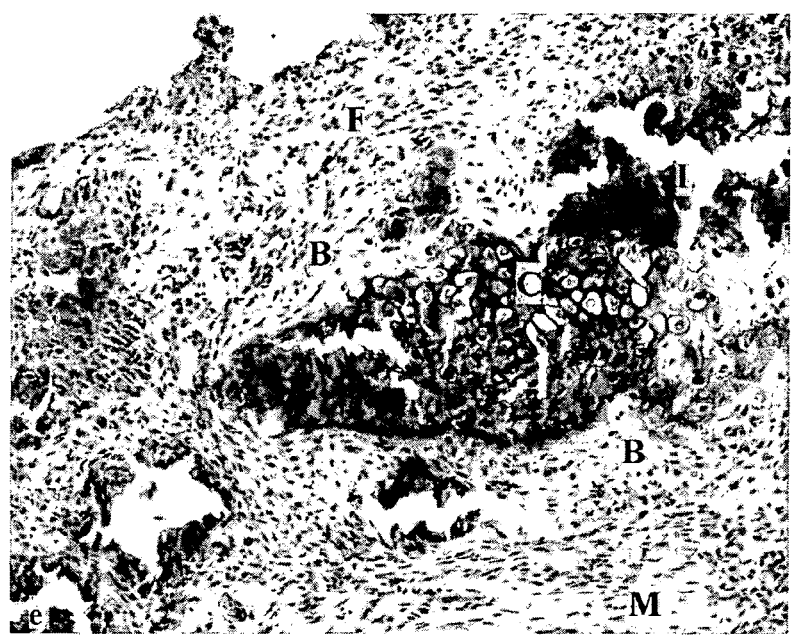
Figure 23F:
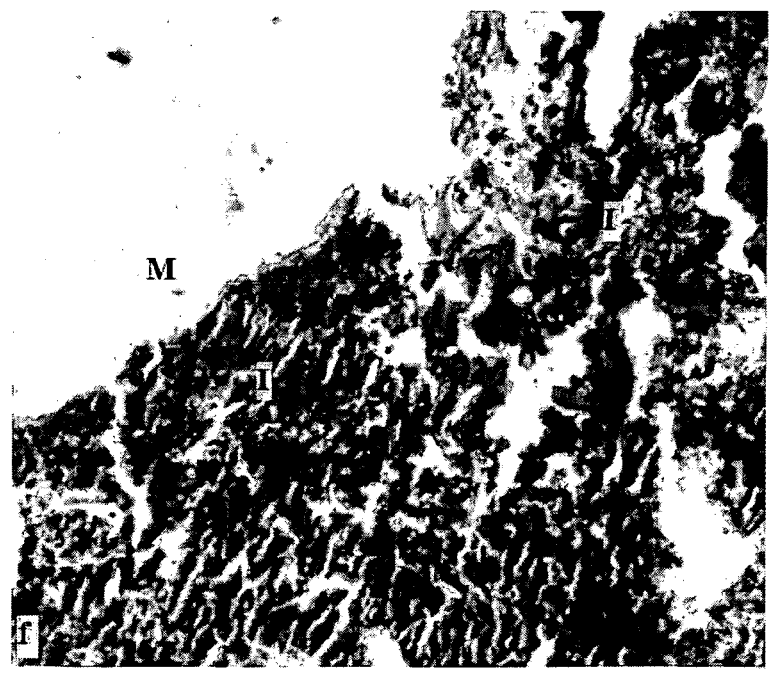
Figure 24C:
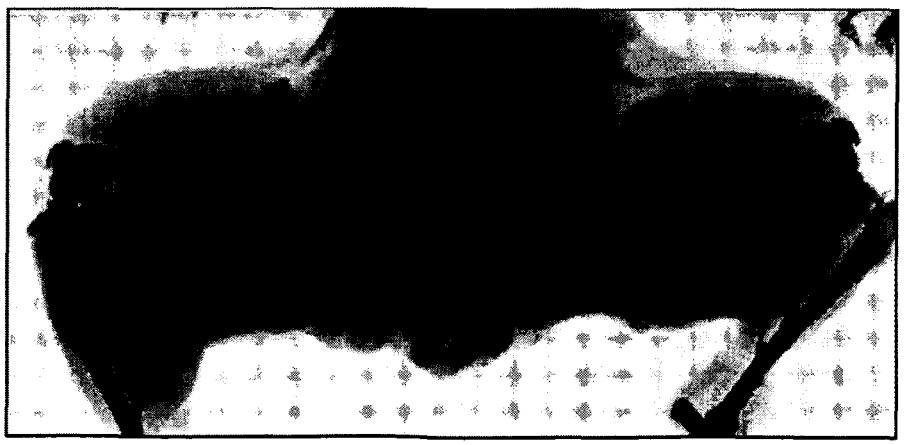
Figure 25:
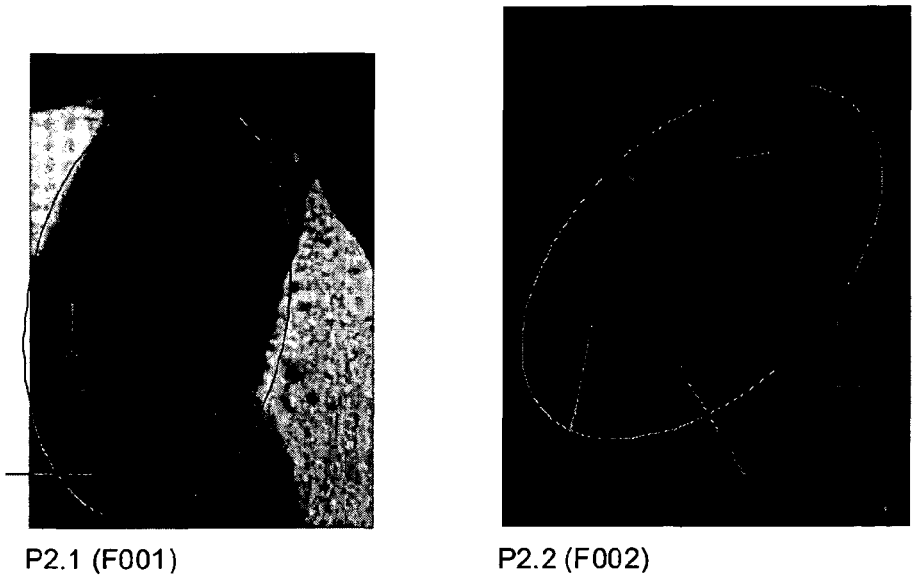
FIG. 25 shows μCT examples of CS active (P2.1) and CS control groups (P2.2) after 3 weeks follow-up. Pellets have resorbed and some bone formation is seen.
Figure 26:
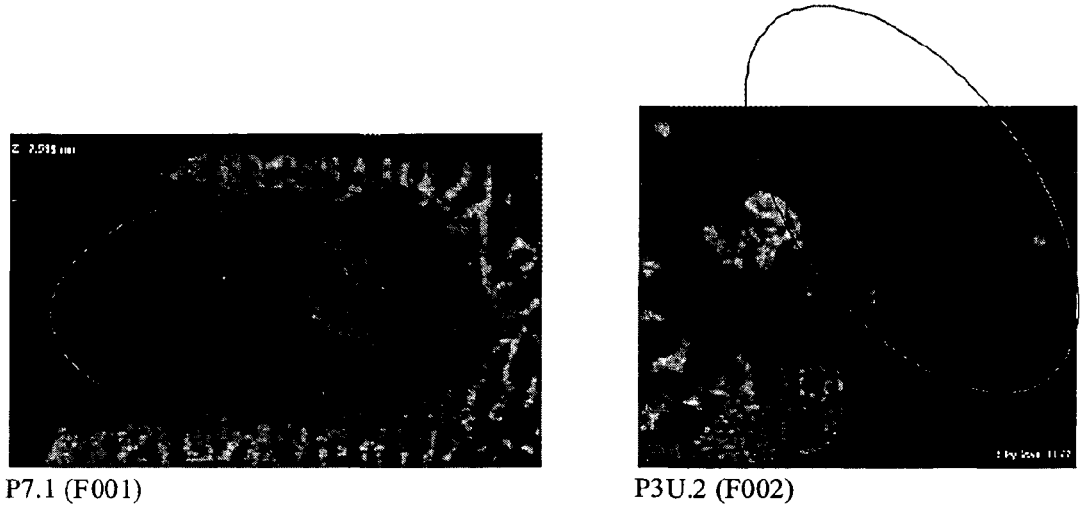
FIG. 26 shows μCT examples of CS active (P7.1) and control (P3U.3) groups after 8 weeks follow-up. More bone formation is seen in the active side compared to the control side.
Figure 31:
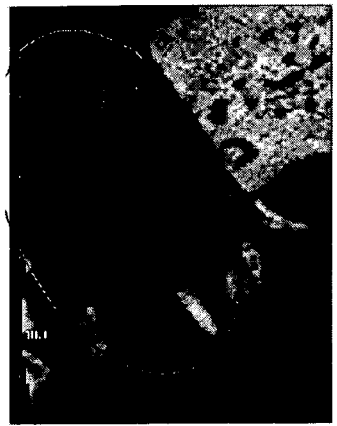
FIG. 31 shows μCT example of empty defect group after 3 weeks follow-up. Defect site is empty and no bone formation is seen.
Figure 32:
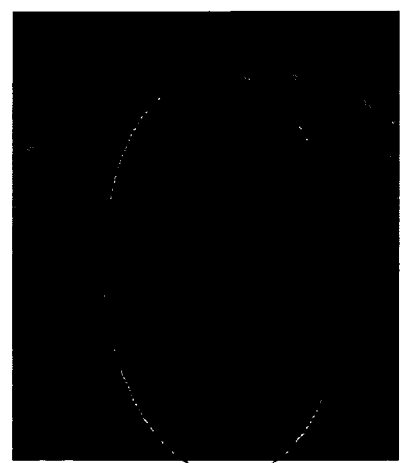
FIG. 32 shows μCT examples of empty defect group after 8 weeks follow-up. Normal, very minor, bone formation is seen on the edges of the defect but defect has not healed.

For group f (calcium sulfate dihydrate-stearic acid), the radiographic analysis and harvesting analysis revealed new bone formation in the active implant group (Table 15, FIG. 24C). The difference between the active implants and the controls was statistically significant (p<0.01). Also, histological analysis revealed clear bone formation and mature and calcified cartilage cells in the active sample (FIG. 23E). No visual bone formation was apparent in the control sample (FIG. 23F).

The comparison between all active groups revealed that group f had the largest measurement area, as determined by the radiographic analysis (p<0.05). Furthermore, groups c and d had significantly larger areas than groups a, b and e (p<0.01). There was also a statistically significant difference between active groups a and e (p<0.05).

4. Discussion

The primary aim of this study was to find a suitable, inorganic, carrier candidate for reindeer bone protein extract. Six different candidates, including four different raw materials, were chosen to evaluate bone formation and implant resorption in the mouse pouch model with a three-week follow-up evaluation. In particular, calcium sulfate-stearic acid was an encouraging carrier candidate for the reindeer bone protein extract.

The reindeer bone protein extract has high bone formation activity, as seen in the bioactivity and previous tests (FIG. 22); however, in a real bone healing situation, the extract cannot work without a scaffold system. Limitations of the carrier selection are set by the characteristics of the reindeer bone protein extract. The primary limitation is that the extract is not water-soluble. Thus, there are at least three different possibilities for implant preparation. The first is that the formulated bone extract suspension can be impregnated into a porous matrix. The second method is to mold the extract and carrier together to form putty or compress them into the discs, and in the third method, the carrier discs or granules are surface coated with the bone extract. Pure collagen has been tested as a carrier in some of our previous studies. Lyophilized extract was mixed into water and then pipetted onto the collagen sponge; alternatively, the collagen sponge was soaked in water and then, with the extract, was bundled up to form an implant. The results of this method showed good bone formation in the pouch mice model and in the segmental defect model; however, it seems that collagen does not support the functionality of the bone forming proteins in the required time. Therefore, an inorganic alternative would provide a better frame for the support of the bone healing effect of the extract. Previously, we have tested combinations of TCP, HAP and coral together with the extract and collagen sponge in the mouse model. Furthermore, bioglass was found to be an acceptable carrier alternative as tested in the rat defect model.

This study was designed to find alternatives for carrier selection while considering the absorption of bone extract and the pore size characteristics of the carrier. With excipients, the lyophilized extract was absorbed into the pores of the TCP:CS 90:10 group, partially surface coated and partially absorbed into the HAP:TCP:CS 30:60:10 group. Furthermore, the surface coating was used in the group of HAP/TCP/CS 60:30:10. The lyophilized reindeer bone protein extract was blended into the carrier material of the CSH and the Cem-Ostetic groups and dry blended, without re-suspending the lyophilized extract, for the CSD-stearic acid group. Because the combination of the lyophilized formulation and the carrier was different for each study group, the distribution and availability of the extract was also different for each group; therefore, statistical comparisons between carrier groups are not valid. The native roentgengraphic method was used to determine the activity of implants in this study; however, this method cannot show bone formation inside of the remnants of the implant. The microtomography imaging method may give more detailed information on bone growth and carrier resorption in future studies. However, new bone formation was clearly seen in the histological analysis completed for this study.

All groups with extract performed better than the control groups without bone extract. The largest amount of bone formation was found in the groups that had the bone extract readily available, which indicates that the bone-forming factors are required at sufficient concentrations during the early stage. This was seen particularly in the HAP/TCP/CS 60:30:10 and CSD-stearic acid groups. In the TCP/CS 90:10, Cem-Ostetic putty and CSH groups, differences between the active implants and the controls were observed, and the implants functioned as an implant with a bone-protein mixture coating. The smallest quantity of bone formation was found in the group HAP/TCP/CS 30:60:10, which indicates that the bone extract was absorbed deep into the scaffold during implant preparation, and the released quantity of bone proteins was too low to induce bone formation. These results support those from previous studies that showed that the formation of new bone depends on a ceramic content with a high HAP/TCP ratio and a high dose of bone proteins. Furthermore, this study confirms that the presence of bioactive components reduced fibrous tissue formation and increased bone formation surrounding the inorganic scaffolds. However, the quantity and availability of bone proteins should be in balance with bone healing and cascade formation.

The DBM products are comparable products for reindeer bone protein extract. The comparable amount of the commercially available DBM product had been also tested in the muscle pouch model but no any sign of bone formation either roentgengraphically or histologically was seen within 21 days (Data not shown). This indicates that proteins in the reindeer bone extract are more specific for inducing new bone, and bone formation capacity of extracted reindeer bone proteins is much better compared with the DBM.

It is known that the presence of bone cells is essential for the degradation of calcium sulfate material. Ideally, bone formation and scaffold degradation follow one another until the defect area has been entirely replaced by new bone. If bone formation is not sufficient to supply mechanical strength, then the scaffold material should degrade slowly to prevent exposure of the support characteristics. This study also revealed that stearic acid had positively affected the enhancement of bone ingrowth and formation in the environment of the calcium sulfate carrier. Stearic acid has been widely used as an excipient in tablet manufacturing because the addition of stearic acid decreases the viscosity of ceramic suspension while increasing the microstructural uniformity of particle packing. Stearic acid is also used as part of plaster castings. Acid is sprayed on the surface of the casting mold that is parted after the casting. Then, stearic acid reacts with the calcium in the plaster to form a thin layer of calcium stearate, which functions as a release agent. Wright Medical Technology Inc. has used stearic acid as a tablet aid in their calcium sulfate products as Osteoset® and recorded good bone healing capacity, as found in previous work by the authors. Thus, the conclusion is that calcium stearate not only has tablet-aiding properties, but also supports bone formation, similar to carboxymethylcellulose.

In conclusion, the greatest amount of bone formation occurred in the groups that had readily available bone extract near the surface of the implant. The combination of TCP or CS and stearic acid appeared to be the most ideal carrier alternative for reindeer bone extract. It was also suggested that the formulation of carrier materials as granules or in an injectable form would increase bone-formation efficacy. This hypothesis will be tested in further studies.

TABLE 15

Radiographic analysis of active implant containing the bone extract and control after 21-days follow-up (opalescent area in mm$^2$). The percent increase compared to the control is shown.

| Group | n | Active mm$^2$ (SD) | Control mm$^2$ (SD) | Increase % |
|---|---|---|---|---|
| a) HAP/TCP/CS 30:60:10 | 8 | 34 (6.08)$^a$ | 25 (3.14) | 36 |
| b) TCP/CS 90:10 | 7 | 41 (12.22) | 27 (1.41) | 52 |
| c) Cem-Ostetic | 7 | 76 (6.49)$^{a,c}$ | 50 (6.04) | 52 |
| d) CS hemihydrate | 6 | 78 (13.47)$^{a,c}$ | 44 (8.33) | 77 |
| e) HAP/TCP/CS 60:30:10 | 8 | 46 (12.87)$^{a,d}$ | 25 (2.77) | 84 |
| f) CS dehydrate + stearic acid | 7 | 97 (13.48)$^{a,b}$ | 49 (13.38) | 98 |

$^a$ $p < 0.01$ vs. control,
$^b$ $p < 0.05$ vs. other active groups,
$^c$ $p < 0.01$ vs. (a), (b) and (e),
$^d$ $p < 0.01$ vs. (a)

Evaluation of Calcium Sulfate and β-TCP as Carriers for Reindeer-Derived Bone Protein Extract in Sheep Implantation and Analytical Methods Evaluation Introduction Bone defects are formed as a result of trauma or in connection with reconstructive surgery where parts of bone is removed due to destructive tissue changes. Critical size bone defects are those where bone alone is not able for spontaneous regeneration of the formed gap and need physical help in regaining the gap between bone parts.

The present inventors have developed a bone protein extract for use in bone surgery. This reindeer bone extract induces effectively ectopic new bone formation in vivo. Reindeer bone protein extract has been prepared from the diaphyseal bone resulting in a mixture of various bone proteins.

The bone protein extract needs a carrier matrix to guide the bone formation and to protect bone proteins from non-specific lysis. The ideal matrix should be biocompatible, bioabsorbable, malleable, and sterilizable. The carrier matrix should bond to the host bone without the formation of scar tissue, and resorb at the same rate as the bone is regenerated.

Different implantation and analysis methods are available. The first product was targeted for the ankle fusion. It was supposed that hole-defect model can fine enough to model the real situation. The sheep hole-defect model has been widely used but not clear critical size defect model could not be defined according to the literature.

The most typical model size was 9 mm×6 mm hole thus we chosen size of 10 mm×6 mm.

According to the literature different imaging and histological methods are the most used and the most practical to show bone healing and reactions in an area of bone trauma. Main aim of this study was to test the operating system of sheep hole-defect model and different analysis methods.

Objectives

This study was designed for evaluation of in vivo performance of three different inorganic carrier candidates combined with reindeer bone protein extract in a sheep femur hole-defect model. Another aim of this study was to provide methodological information for the planning of future performance studies. These include the testing of the technical issues of the implantation study (size of critical size defect compared to the defect size that finding from the literature, operation methods with anaesthesia and pain killing, clinical observations, local tolerance and recovery from implantation, handling of the test material, follow-up time, and analytical methods) and information on the bone healing process with three different carrier candidates.

Materials and Methods

Study Design

The study has been approved by the Animal Care and Use Committee of the Southern Finland Provincial Government, approval number ESLH-2009-0568/Ym-23.

In this study two hole-defects with a diameter of 6 mm and a depth of 10 mm were induced to the femoral medial condyles of the sheep hind legs with a drill under general anesthesia. Location of defects was marked with small titanium K-wires. The drill holes of the left and right femur were filled with the carrier material and the reindeer bone protein extract, or with the carrier material alone, or left empty (untreated controls). The new bone formation was determined with fluorochrome in vivo. After predetermined time the animals were euthanized and femurs were harvested for further laboratory investigations ex vivo. The follow-up time was three (n=5) and eight weeks (n=5).

The test articles were (Table 16):
1. BBS001 F001: 30 mg/g surface coated Calcium sulfate (CS) pellets
2. BBS001 F002: CS control pellets
3. BBS001 F003: Beta Tricalcium phosphate (β-TCP, high porosity, low density) granules and Polyethylene Glycol/Glycerol (PEG/GLY) gel-→paste
4. BBS001 F004: β-TCP granules (high porosity, low density) with PEG/GLY control
5. BBS001 F005: Beta Tricalcium phosphate (β-TCP, low porosity, high density) granules and Polyethylene Glycol/Glycerol (PEG/GLY) gel-→paste
6. BBS001 F006: β-TCP granules (low porosity, high density) with PEG/GLY control

TABLE 16

Test articles

| Group code | Implant | Abbreviation |
|---|---|---|
| BBS001 F001 | Calcium sulfate, active | CS active |
| BBS001 F002 | Calcium sulfate, control | CS control |
| BBS001 F003 | TCP low density, active | TCPld active |
| BBS001 F004 | TCP low density, control | TCPld control |
| BBS001 F005 | TCP high density, active | TCPhd active |
| BBS001 F006 | TCP high density, control | TCPhd control |
| Empty | no implant | Empty |

The target composition of the BBS001 F001 product contained about 30 mg dry protein extract per 1 g of product, where the carrier was in the form of 3 mm×3 mm slightly conical pellets. The volume of the 6 mm×10 mm defect was 0.283 ml, and it could involve 6 pellets resulting in about 4 mg extract per defect.

The calcium sulfate pellet was manufactured by molding from beta calcium sulfate hemihydrate (Sigma-Aldrich, 97%, code 12090) and it included about 5 weight (w) % stearic acid (Merck PARTECK LUB STA (Stearic acid vegetable grade), PH EUR, batch K39557661). The wet protein extract was coated onto the pellets with Tween 20 (Ph. Eur., code: 44112, Fluka, Sigma-Aldrich), CMC (Carmellos. Natr. Ph. Eur, Tamro) and PEG 400 (Macrogol 400, 0784710, Tamro). The final composition contained 2.4% dry protein extract, 1.12% CMC, 0.19% PEG400, 0.036% Tween 20, 91.4% calcium sulfate and 4.8% stearic acid.

The target compositions of the BBS001 F003 and BBS001 F005 products contained by volume the same amount of dry extract as in BBS001 F001.

The PEG/GLY phase in the BBS001 F003 and BBS001 F005 products contained 1.62% lyophilized protein extract, 38.1% PEG 2K (Clariant, Kemi Intressen, code: 107903) and 60.3% Glycerine (Croda, Kemi Intressen, code: pricerine 9095). The β-TCP in BBS001 F003 and BBS001 F005 was in the size of 300-500 µm (Cambioceramics, lot GR090819B, high porosity, low density and Cambioceramics, lot GR090819A, low porosity, high density).

The wet protein extract was lyophilized before mixing with the PEG/GLY mixture. The dry lyophilized protein extract contained 0.35% Tween 20 (Ph. Eur., code: 44112, Fluka, Sigma-Aldrich), 0.97% Trehalose dihydrate (for microbiology, Fluka, Sigma-Aldrich, code 90210), 4.1% Glycin (puriss, Ph, Eur., code; 33226, Riedel-de Haën, Sigma-Aldrich) and 10.9% Mannitol (Ph. Eur., code:17311, Fluka, Sigma-Aldrich).

The final composition of the BBS001 F003 (high porosity, low density) contained 1.14% lyophilized extract, 29.7% TCP, 42.4% Glycerine and 26.8% PEG 2K.

The final composition of the BBS001F005 (low porosity, high density) contained 1.00% lyophilized extract, 37.8% TCP, 37.5% Glycerine and 23.7% PEG 2K.

Test System

Species, Strain, Origin, Quality, Number of Animals, Age

Ewes (female sheep) of strain Suomenlammas (Finland sheep) were used.

The animals originated from the Finnish sheep breeding herds for meat and wool production. The ewes were all breeders for several times. The animals had been acquired for use as laboratory animals.

Totally 11 animals were used in this research study. Their average age was 7 years and 7 months.

Implantation

The operation was performed under general inhalation anaesthesia, induced by an intravenous injection of Propofol (5-7 mg/kg i.v., Propofol-®Lipuro, B. Braun Melsungen AG, Melsungen, Germany) and maintained with Isoflurane in 1-1.5% (Isoba Vet, Schering-Plough A/S, Farum, Denmark) oxygen-air mixture. Before the anaesthesia the sheep were pre-medicated with Medetomidine-Ketamin (0.015 ml/kg i.m., Domitor® Vet (1 mg/ml), Orion Oyj, Espoo, Finland and Ketalar (50 mg/ml), Pfizer Oy, Helsinki, Finland) and intubated. The sheep were controlled with a heart monitor during the operation.

Fentanyl (2 µg/kg/hour, Fentanyl ratiopharm, Ratiopharm GmbH, Ulm, Germany) depot plaster was given per-operatively for 72 h pain relief. Additionally, 2 ml of Fentanyl (50 µg/ml i.m., Fentanyl-Hameln, Hameln Pharmaceuticals GmbH, Hameln, Germany) was injected twice of day intramuscularly during first 72 h after the operation.

Amoxycillin (15 mg/kg i.m., Betamox® Vet, 150 mg/ml, Norbrook Laboratories Ltd, Newry, Nord-Ireland) were injected as antibiotic prophylaxis, subcutaneously 24 h preoperatively and once per day two days postoperatively.

The implants were placed bilaterally into the circular hole-defect. Therefore, the animals were immobilized on their back and both legs were shaved and disinfected with ethanol. A longitudinal incision was made on the medial surface of the femur and the condyle was exposed by blunt dissection. Small open blood vessels were closed by diathermia. Two holes with a diameter of 6 mm and a depth of 10 mm were drilled (cordless drill, Bosch PSR12-2). The distance between the defects is at least 1.5 cm. First a 2 mm pilot hole was drilled. Subsequently, this defect was gradually widened using drill bits of increasing sizes (3.5 mm and 4.5 mm) to a final diameter of 6 mm (Magnum quality tools, HSSart 76035, HSSart 76045 and HSSart 76060). The drill holes were rinsed with saline to eliminate bone debris and were tamponated with gauzes to stop bleeding. Meanwhile, the location of the defects was marked, using small titanium K-wires at front side of the drill holes. The holes were filled with test article, or left empty.

Finally, the subcutaneous tissues were closed in layers with resorbable continuous 2-0 Vicryl sutures, and skin with 2-0 Mohosof sutures. The skin around defect site was local anesthetized by Bupivacain hydrochlorid (5 mg/ml Bicain, Orion Oyj, Espoo, Finland) and disinfected with povidone-iodine.

Follow-Up

The follow-up time was 3 weeks (n=5 sheep) or 8 weeks (n=5 sheep) after the surgery. One sheep (P3) was euthanized just after the operation because of extensive bleeding.

Euthanasia and Necropsy

After predetermined time periods the animals were transported to Laboratory Animal Centre where they were euthanized. Euthanasia were performed with Pentobarbital (60 mg/kg i.v. Mebunat® Vet, Orion Oyj, Espoo, Finland). Before this, sheep were anaesthetised by an intramuscular injection of Medetomidine-Ketamin (0.015 ml/kg i.m., Domitor® Vet (1 mg/ml), Orion Oyj, Espoo, Finland and Ketalar (50 mg/ml), Pfizer Oy, Helsinki, Finland).

Sampling

After euthanasia the femurs were excised and preserved in ice before computed tomography (CT). Then the bone blocks to be taken for histological analyzes were preserved in 10% buffered formalin. Before histological analyzes one sample from every group were imaged with micro-CT.

Data Analysis

Micro-CT

One sample from every study group and follow-up points were scanned by using micro-CT (SkyScan, x-ray microtomagraph, University of Turku). Two scanned samples were analyzed using CTAn (SkyScan) software.

Histology

After the µCT imaging the bones are fixed in phosphate-buffered formaldehyde solution (pH=7.4), dehydrated in increasing ethanol concentrations (70-100%) and embedded in methylmethacrylate (MMA) for histological processing.

After polymerization, thin sections are prepared in a transverse direction to the axis of the implant using a modified sawing microtome technique. Four-micrometer sections were cut, and one section was stained with Masson-Goldner Trichrome (MG) stain and one section with Hematoxylin Eosin (HE) stain.

Implantation site will be examined for the assessment of bone formation, resorption of carrier material and local tolerance.

Histomorphometry

Sections of each implant were examined by light microscopy. All HE-stained sections was photographed (super high quality image) by stereo microscopy (Olympus SZX9, Europe, camera: U-CMAD3, Japan, University of Oulu, Laboratory of Process Metallurgy) by 6.3× magnification. A single stained section image was transferred to the computer screen and the defect site was chosen as region of interest (ROI). Area of new bone at the defect site was calculated by image processing and analysis software (Fiji-win-32).

Statistical Methods

Because of small number of samples (n=3 in every group), statistical methods were not used.

Results

Micro-CT

One axial example slice from the middle of every sample is presented (FIG. 25-30).

Slices from active low density TCP (3 week P2.3 and 8 week P7.3) were analyzed to show how remain of carrier materials can difference from new bone formation. The main result in this was that new bone matrix including granules was 25 volume % after 3 weeks follow-up and 46 volume % after 8 weeks follow-up. Volume of particles without joining to new bone or other particles was 1.4 volume % after 3 weeks and only 0.10 volume % after 8 weeks. This method is suitable to show filling volume and resorption of carrier material in the defect.

Histological and Histomorphometric Analysis

Figure 33:
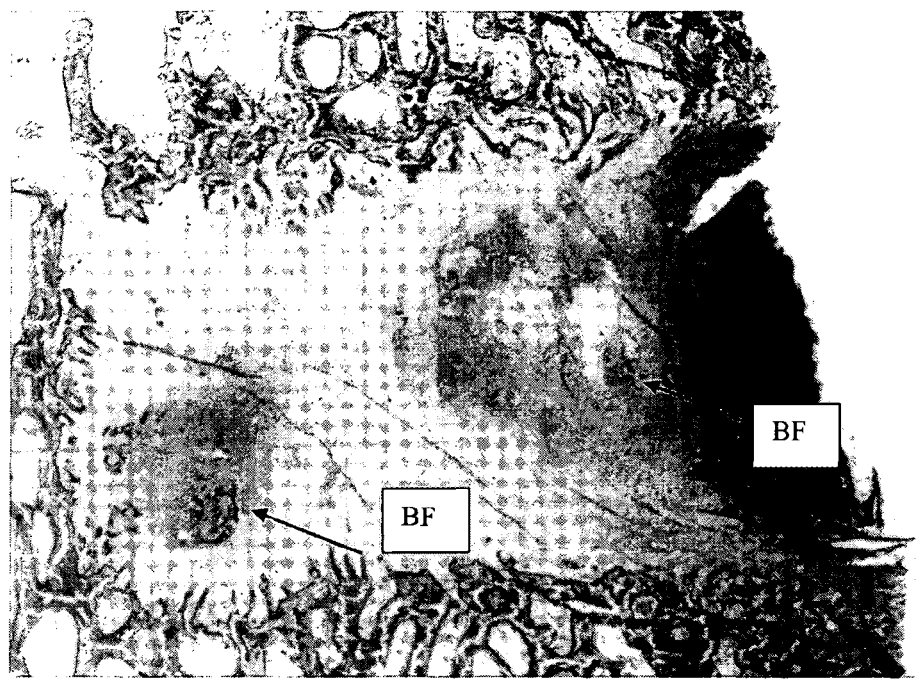
FIG. 33 shows histological slice of CS active, 3 weeks follow-up (MG stain, original magnification 6.3×, BF=new bone formation area). Little bone formation is seen.
Figure 34:
FIG. 34 shows histological slices of CS active, 8 weeks follow-up (MG stain, original magnification 6.3×, BF=new bone formation). Lot of bone formation is seen in the defect site.
Figure 35:
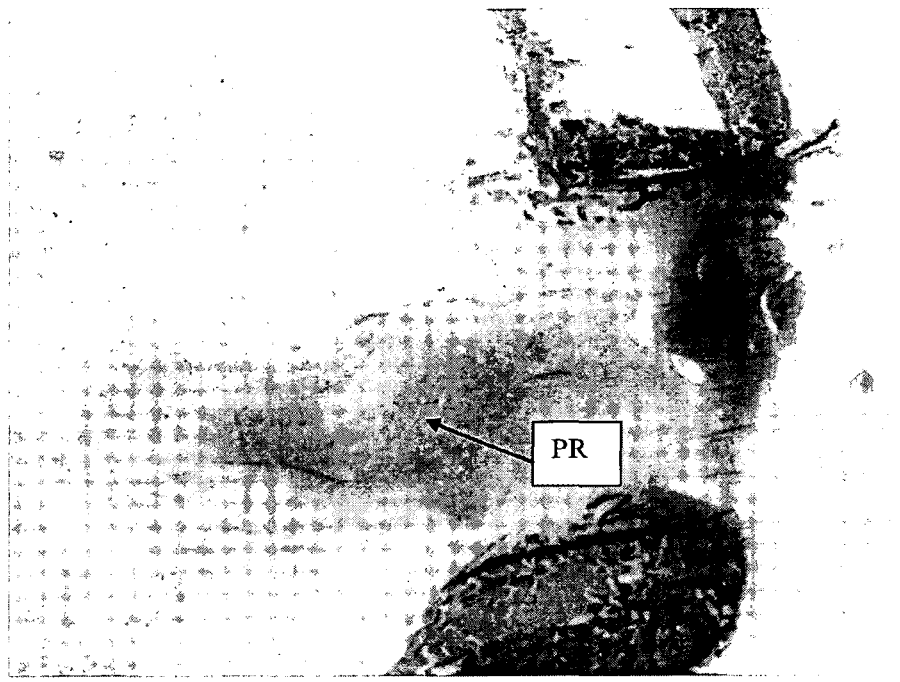
FIG. 35 shows histological slice of CS control, 3 weeks follow-up (MG-stain, original magnification 6.3×, PR=Remnants of pellets). Remnants of pellets are seen in the defect site but no signs of new bone formation.
Figure 36:
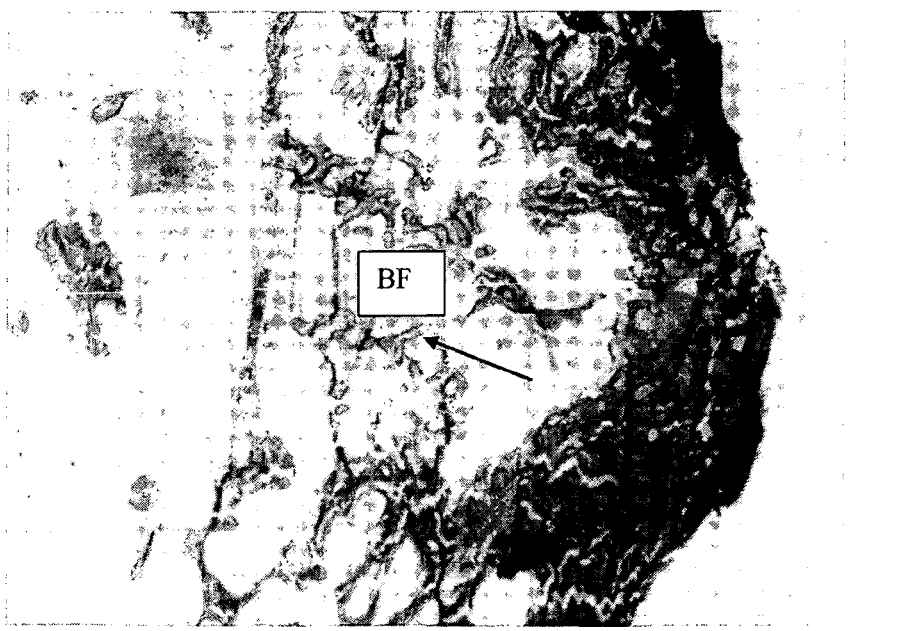
FIG. 36 shows histological slice of CS control, 8 weeks follow-up (MG-stain, original magnification 6.3×, BF=new bone formation). Some new bone formation can be seen in the defect site. The sections of the slices are not axially parallel to the defect.
Figure 37:
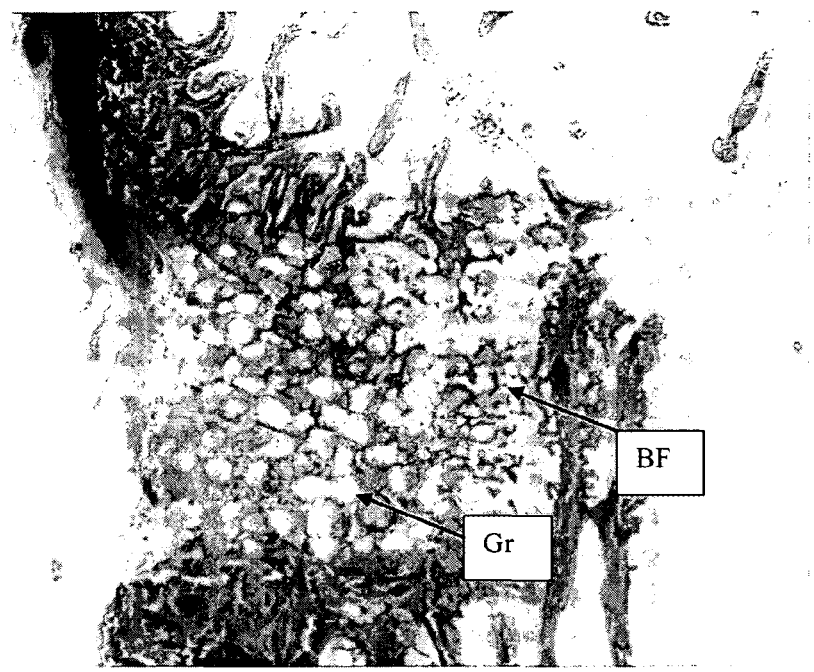
FIG. 37 shows histological slice of β-TCPld active, 3 weeks follow-up (MG-stain, original magnification 6.3×, BF=new bone formation, Gr=TCP-granule). Resorption starting of the granules are seen and new bone formation is seen around the granules
Figure 38:
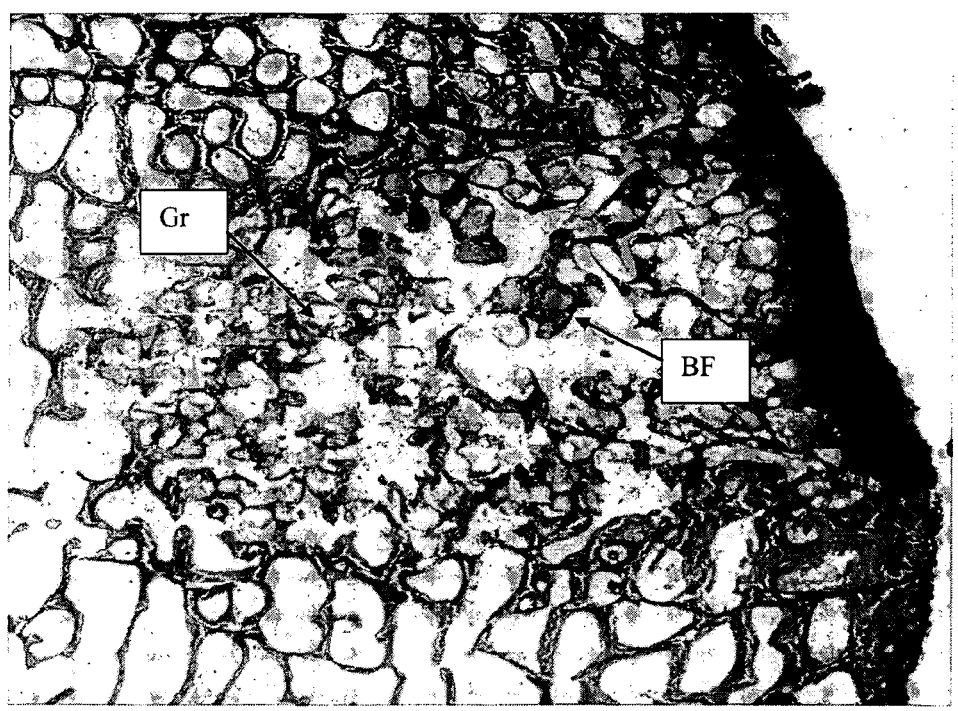
FIG. 38 shows histological slices of β-TCPld active, 8 weeks follow-up (MG stain, original magnification 6.3×, BF=new bone formation, Gr=TCP-granule). Defect is well filled with new bone and marked resorption of granules are seen.
Figure 39:
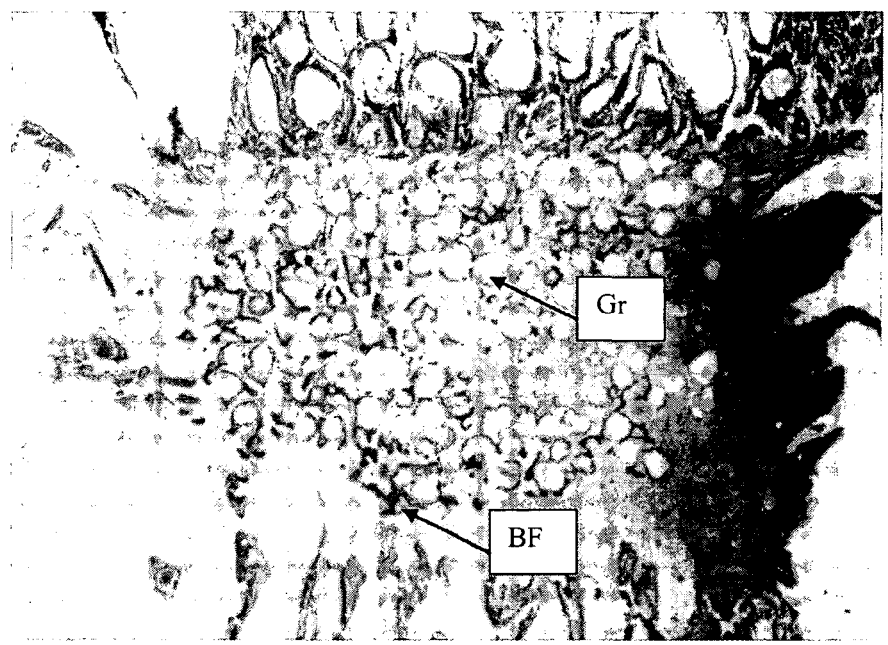
FIG. 39 shows histological slice of β-TCPld control, 3 weeks follow-up (MG stain, original magnification 6.3×, BF=new bone formation, Gr=TCP-granule). There are only minor sign of resorption of granules and minor new bone formation around the granules.
Figure 40:
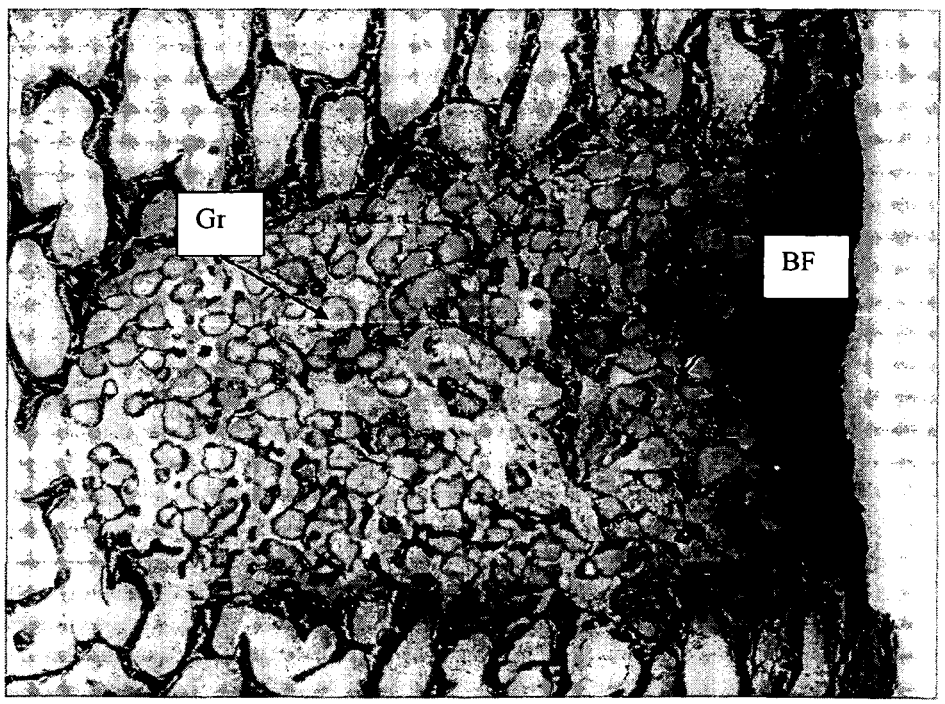
FIG. 40 shows histological slices of β-TCPld control, 8 weeks follow-up (MG stain, original magnification 6.3×, BF=new bone formation, Gr=TCP-granule). Granules are seen and new bone formation around the granules. But the amount of bone formation is much lower and resorption of granules much slower corresponding to the β-TCPld active group (FIG. 38).
Figure 41:
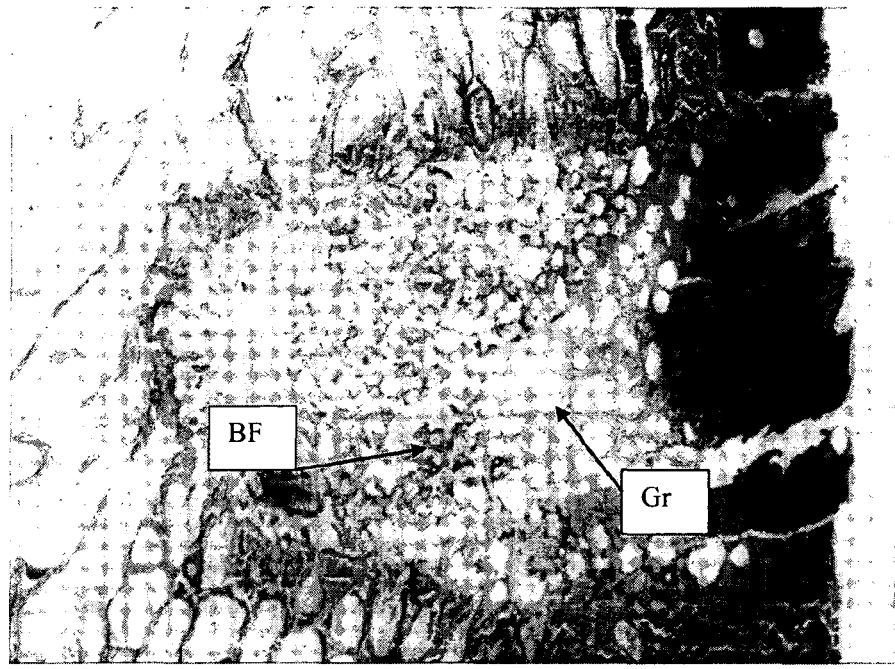
FIG. 41 shows histological slice of β-TCPhd active, 3 weeks follow-up (MG stain, original magnification 6.3×, BF=new bone formation, Gr=TCP-granule). Resorption starting of granules is seen and new bone formation around the granules.
Figure 42:
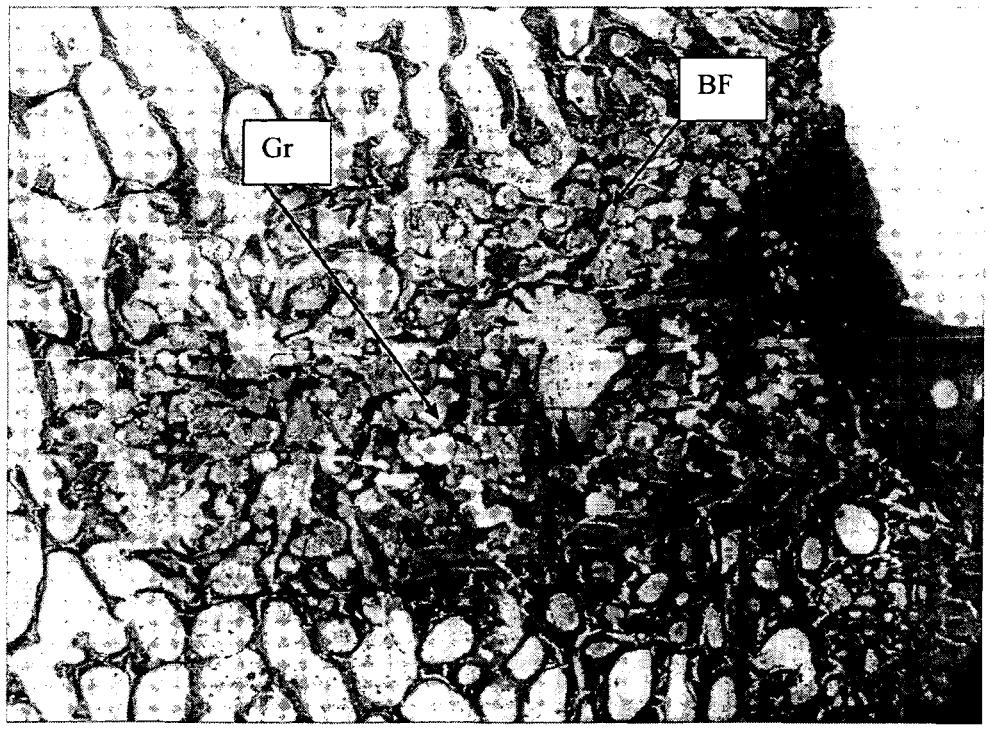
FIG. 42 shows histological slices of β-TCPhd active, 8 weeks follow-up (MG stain, original magnification 6.3×, BF=new bone formation, Gr=TCP-granule). Minor remnants of granules are seen and excellent new bone formation. Defect is completely filled with new bone and resorption of granules is very high.
Figure 43:
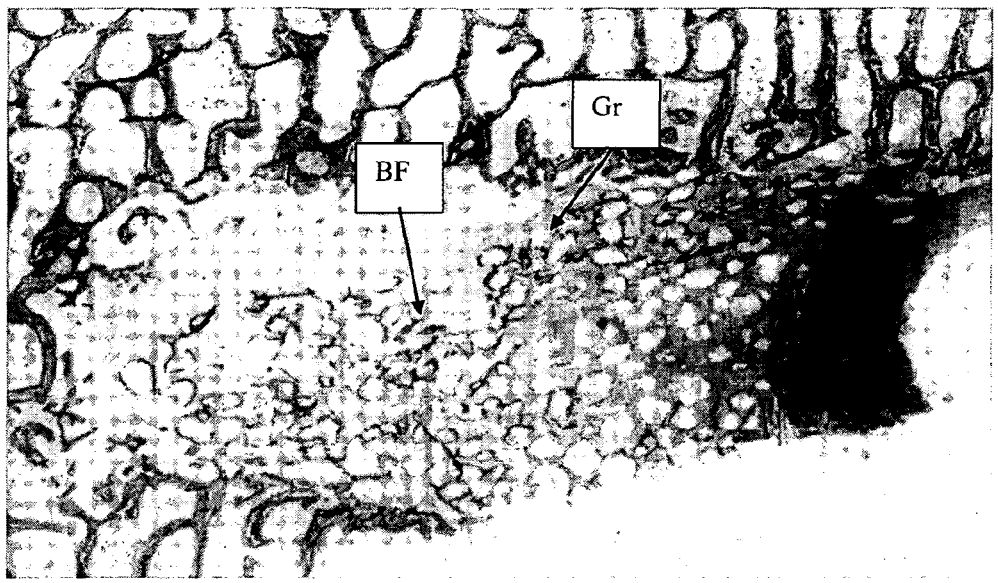
FIG. 43 shows histological slice of β-TCPhd control, 3 weeks follow-up (MG stain, original magnification 6.3×, BF=new bone formation, Gr=TCP-granule). Resorption of granules is slow and minor new bone formation around the granules is seen
Figure 44:
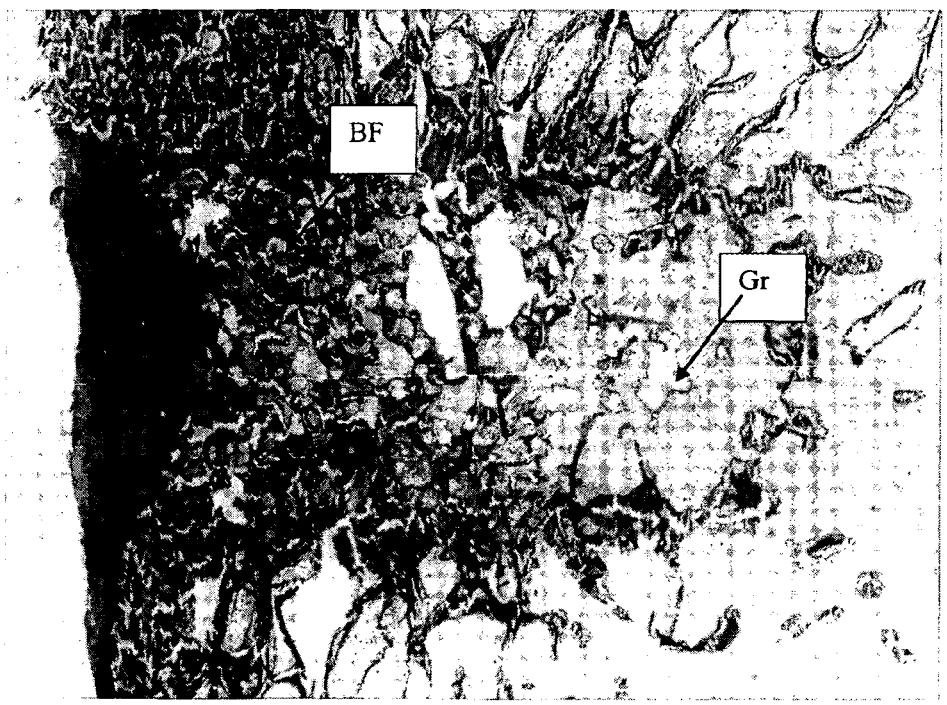
FIG. 44 shows histological slices of β-TCPhd control, 8 weeks follow-up (MG stain, original magnification 6.3×, BF=new bone formation, Gr=TCP-granule). Granules are seen and new bone formation around the granules. Bone formation is much less and resorption of granules is slower than in active group (FIG. 42).
Figure 45:
FIG. 45 shows histological slice of empty defect, 3 weeks follow-up (MG stain, original magnification 6.3×). Empty defect is empty.
Figure 46:
FIG. 46 shows histological slice of empty defect, 8 weeks follow-up (MG stain, original magnification 6.3×). Empty defect is empty (some normal bone formation seen in the edges of the defect.
Figure 47:
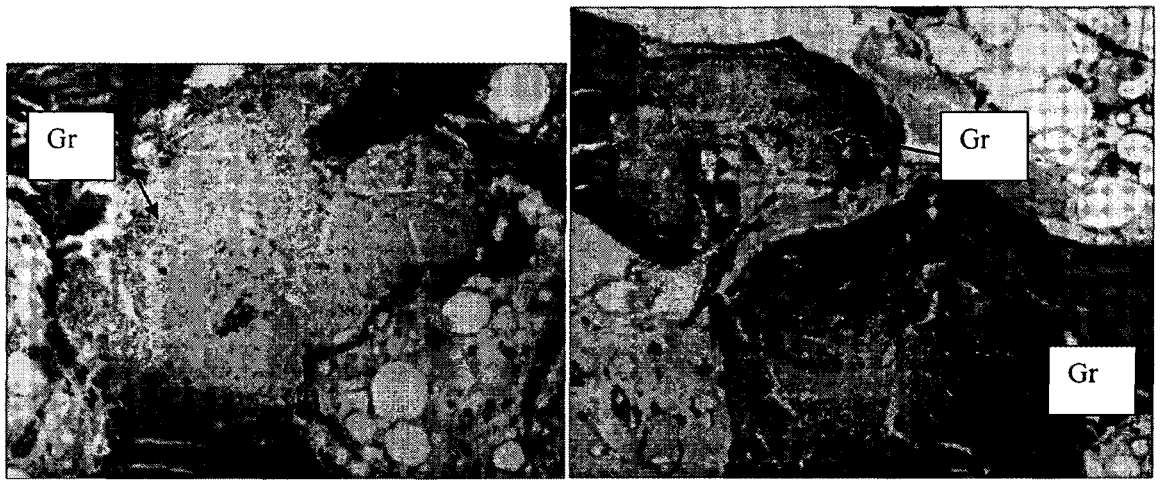
FIG. 47 shows resorption of TCPld control (on the left) and active (on the right) granules (MG stain, Original magnification 10×, Gr=TCP-granule).
Figure 48:
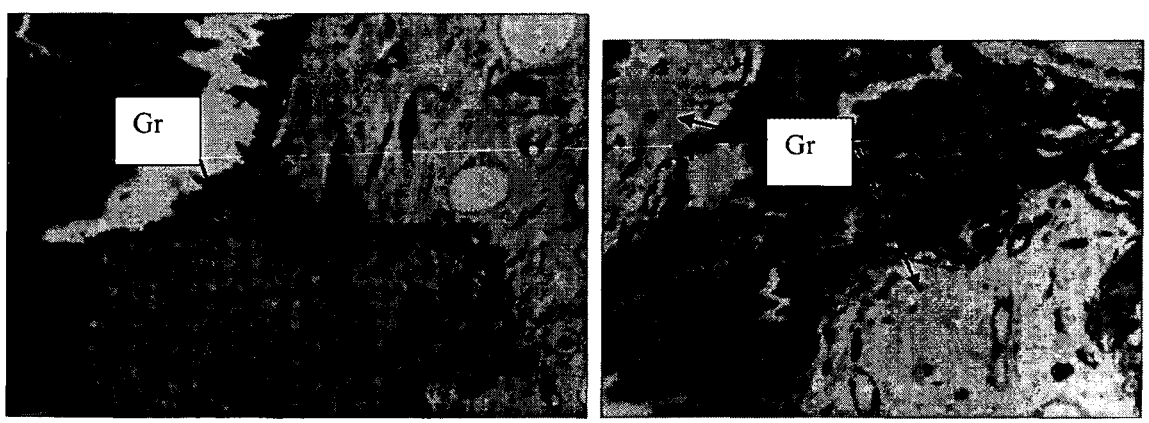
FIG. 48 shows resorption of TCPhd control (on the left) and active (on the right) granules (MG stain, Original magnification 10×, Gr=TCP-granule).

Summary of Comments on Histological Analysis:
1. BBS001 F001: Calcium sulfate (CS active) pellets,
    3 weeks follow-up (FIG. 33)
        Remnants of pellets can be found
        New bone formation in the defect side, no in the middle of the defect
    8 weeks follow-up (FIG. 34)
        Remnants of pellets (very small particles)
        Bone formation around the particles
2. BBS001 F002: CS control pellets
    3 weeks follow-up (FIG. 35)
        Lot of fibrotic matrix on the whole defect area
        Small remnants of pellets can be found
    8 weeks follow-up (FIG. 36)
        Pellets have resorbed
        Fibrotic tissue filled the defect
        Some bone formation can be found
3. BBS001 F003: β-TCPld active paste
    3 weeks follow-up (FIG. 37)
        Remnants of granules can be found but no resorption reaction
        Bone formation also in the middle of the defect, around granules
    8 weeks follow-up (FIG. 38)
        Osteoclasts resorb granules
        Good new bone formation on the defect area
        Clear bone union
4. BBS001 F004: β-TCPld control
    3 weeks follow-up (FIG. 39)
        Lot of remnants of granules
        Lot of fibrotic matrix on the cortex area
        Some granules around by new bone
    8 weeks follow-up (FIG. 40)
        Lot of remnants of granules
        Granules not as resorbed as in active case
        New bone formation around granules
5. BBS001 F005: β-TCPhd active paste
    3 weeks follow-up (FIG. 41)
        Fibrotic matrix on the surface of the defect hole
        Lot of remnants of granules but also good new bone formation
    8 weeks follow-up (FIG. 42)
        Clear resorption of granules can be seen
        New bone formation around the granules on whole defect site
        Clear bone union
6. BBS001 F006: β-TCPhd control paste
    3 weeks follow-up (FIG. 43)
        Remnants of granules
        Lot of fibrotic matrix on the cortex area
        Some granules around by new bone
    8 weeks follow-up (FIG. 44)
        Very thick fibrotic tissue layer
        No bone union
        Bone formation only around the granules
        Some remnants of the granules but only on the edge of the defect
7. Empty defect
    3 weeks follow-up (FIG. 45)
        Only fibrotic matrix
    8 weeks follow-up (FIG. 46)
        Lot of fibrotic tissue on the cortex area
        No bone formation on the middle of the defect Resorption of granules was faster in active groups than in control groups. We used two different porosity sizes of β-TCP granules. Clear difference between sizes can not be defined although faster resorption and better bone ingrowth were seen in low porosity group (group TCPhd active). Resorption difference between TCPld and TCPhd groups after 8 weeks follow-up can be seen in FIGS. 47 and 48.

Discussion

The main aim of this research study was to find a suitable, inorganic, carrier candidate for reindeer bone protein extract and test the operation and analysis method of the sheep hole-defect model. Three different candidates, including two different raw materials, were chosen to study bone formation and implant resorption in this pilot study with three weeks and eight weeks follow-ups. The used operation and observation methods worked well and are usable in the future studies. The best bone formation and defect healing was seen in the paste groups that included β-TCP and lyophilized reindeer bone extract together with polyethylene glycol and glycerol.

BBS Ltd has targeted their first product for the ankle fusion. It was supposed that hole-defect model can fine enough to model the real situation. The most typical model size was 9 mm×6 mm hole thus we chosen size of 10 mm×6 mm. This was big enough because no bone healing was seeing in empty defect after 8 weeks. Now the femur was used but if targeting of this product is thought, a metatarsal bone of sheep is also suitable operating bone model. We used K-wires to sign the defect site. This was a good and worked idea. Especially, after 8 weeks in some cases it was not clear to find the defect without using help of K-wires. Furthermore, K-wires were used with help in pQCT imaging and in preparation of histological slices (to find the middle point of the defect).

Three different formulation alternatives with two different matrices were investigated in this study. Both used inorganic materials are biocompatible and osteoconductive.

Calcium sulfate pellets with stearic acid were moulded and dried and then coated with reindeer bone extract. Pure pellets worked as control. One dose involved six pellets that were easy to set for the defect. Pellets showed clear bone formation in Bioassay (mice model). In this sheep study resorption of the pellets was so fast that only little bone formation was found in this group. However, begin of bone union can be find after 8 weeks follow-up. Pellets without extract had not effect of bone formation. Optimizing of resorption speed of pellets is needed before the final study. Perhaps, size of one pellet could be smaller that defect filled better and more protein coated area would be available. This could enhance bone ingrowth in the defect.

Two other tested formulations were in paste form. Beta tricalcium phosphate (β-TCP) granules (two porosity sizes) and lyophilized reindeer bone extract were added to paste formed from polyethylene glycol and glycerol. Then the paste was dosed into syringes. Mostly, it was easy to inject the paste dose into the defect but in some cases the paste did not unstuck from the piston of the syringe and minor part of paste come out of the defect. This can be one reason that bone ingrowth has not be seen in the bone cortex, only in the middle of defect. Paste did not show clear bone formation in Bioassay (TONA002.003) but in this sheep study resorption of granules and bone formation were found, especially after 8 weeks follow-up. β-TCP is material that is alone osteoconductive, thus we found new bone formation also in control groups. But bone formation was around the granules and no bone ingrowth was seen. Furthermore, resorption of granules was faster in active groups than in control groups. We used two different porosity sizes of β-TCP granules. Clear difference between sizes can not be defined although faster resorption and better bone ingrowth were seen in low porosity group (group TCPhd active). Optimizing of resorption speed of paste is needed before the final study. Paste (PEG and GLY) with granules must be kept in the defect longer that bone ingrowth in bone cortex part is also possible.

In inorganic material research studies widely used follow-up points are 3 to 12 weeks depending on the used material and defect model. In this study we used three weeks and eight weeks follow-ups. The first time point showed only begin of the bone formation and material resorption. The operated area (wound, muscles) had already healed in three weeks. The second time point showed clear difference between active and control groups, and no bone formation in empty defects. But full bone ingrowth was not seen in the active groups after eight weeks. Especially, TCP involved groups need a longer follow-up that granule resorption could be clearly defined. On the following study the follow-up could be between 8 to 16 weeks.

The best and most informative imaging results were got from μCT. This gives higher resolution images and thus more detailed information from new bone formation and carrier resorption than normal CT. In this study we analyzed only two example samples by μCT but method is very encouraging to use as main analysis method in the future. It is also recommendable to get some images just after implantation. Thus, you have information, how your implantation has been succeeded and how analyzing values of imaging are in so called null point.

After imaging samples were sent to histology. Two staining methods were used. Especially, Masson Goldner Trichrome staining showed new bone formation and carrier resorption because this staining is specific for bone. Area of new bone in the defect site was measured by histomorphometrically from photograph taking by stereomicroscope. But only one slice from every group was so good that measurement was acceptable. Most of slices were broken or some other problems that quantitative analyzing was impossible. Although bone formation and defect healing were able to see in histology, we have to more take account the quality of slice in the future that quantitative measuring would be possible to show difference between the groups.

Conclusion

The hole-defect of this size is a critical size defect and is therefore suitable for evaluation of bone healing effects of investigational medical devices. Used operation, anesthesia and analyzing methods are usable also in the future studies for this sheep strain. Both calcium sulfate and tricalcium phosphate are suitable carrier materials, but optimizing of formulation is needed. It seems that formulation form that fills the whole defect in the beginning of the bone healing cascade is the best alternative. Bone healing effect was really better and excellent in the defect treated with active implants compared to the control defects.

Bone Formation Performance of Reindeer Bone Protein Extract Formulations, Autograft and Demineralized Bone Matrix in Sheep Hole Defect Model 1 Introduction Autograft is the traditional method of bone repair enhancement, but harvesting of bone grafts can lead to complications, such as bleeding, pain, and infection. Autografts have also limited availability thus, as an alternative, many inorganic materials are used. Calcium phosphates such as hydroxyapatite (HAP) and tricalcium phosphates (TCP) and their variations are commonly known bone substitute materials. These materials provide an osteoconductive scaffold to new bone forming.

The bioactivity of inorganic materials can be increased by adding osteogenic stimulus to the bone graft extender. Allografts, demineralised bone matrices (DBM) and native bone extracts have been shown to increase bone healing capacity and enhance integration in many different studies. Combinations of bovine bone-derived growth factors in collagen and DBM or coralline HAP carriers have been shown to be as good as iliac crest autografts when studied as fusion rates in spinal arthrodesis in rabbits and monkeys and humans.

Reindeer bone extract is a collagen and growth factor mixture extracted from the extracellular matrix of cortical diaphyseal bone. Reindeer bone protein extracts are similar to animal-derived bone tissue extracts in composition, method of manufacture, and intended use and application. The closest comparable products are Colloss® and Colloss® E, which are demineralized bone extracts created from bovine and equine bone, and human demineralized bone matrix (DBM) products, such as Osteoset® DBM Pellets.

For the current study, we hypothesized that reindeer bone extract implants have equivalent or better bone formation capacity than bone autograft or demineralised bone matrix using the sheep hole defect model. To test the hypotheses, we compared the ability of different reindeer bone extract formulations to stimulate bone formation and repair in the hole defect model of Nuss et al. 2006. The outcomes were compared with untreated defects, and defects filled with beta tricalcium phosphate (β-TCP) ceramic, commercially available demineralised bone matrix (Grafton® DBM), and autograft.

2 Materials and Methods 2.1 Bone Protein Extract

The bone protein extract was extracted and purified from the diaphyseal bone of the reindeer as described previously (Jortikka et al. 1993). The obtained bone protein extract was freeze-dried at −20° C. degrees using excipients (surfactant (Polysorbat 20, Fluka, Sigma-Aldrich), lyoprotectant (D-(+)-Trehalose Dihydrate, Fluka, Sigma-Aldrich), bulking agent (Glycine, Riedel-de Haen, Sigma-Aldrich) and buffer (D-Mannitol, Fluka, Sigma-Aldrich)).

2.2 the Test Articles and Study Groups

The test articles and study groups are shown in table 17.

2.3 Sample Preparation

Polyethylene glycol 2000 (PEG), glycerol and stearic acid were heated until a clear mixture was formed. The mixture was cooled under continuous mixing to form an opalescent paste, after which the required amounts of the lyophilized bone extract and TCP granules were added. The formulated paste was packed in syringes and closed in aluminium foil pouches. All samples were manufactured in a laminar flow cabin to reduce the bioburden, and then terminally gamma-sterilized (15 kGy).

In the autograft group the bone material was removed from the test hole sites of the same sheep using chisel and trephane drill.

2.4 Animals

A total of 10 healthy ewes of the strain the Finnish archipelago sheep were used. Animals were three years old and their bodyweight were 52 to 59 kg.

The implantation sites were the proximal, cancellous, part of the diaphysis and distal epiphysis of humerus and femur. This provided a total of 8 various implant sites per animal. The study protocol was carried out according to the Finnish Laws of animal welfare and was approved by the institutional animal experiment and ethical committee. All animals survived through the 8 weeks follow-up.

2.5 Surgical Procedure

The operation was performed under general inhalation anaesthesia, induced by an intravenous injection of Propofol (5-7 mg/kg i.v., Propofol-®Lipuro, B. Braun Melsungen AG, Melsungen, Germany) and maintained with Isoflurane in 1-1.5% (Isoba Vet, Schering-Plough A/S, Farum, Denmark) oxygen-air mixture. Before the anaesthesia the sheep were premedicated with Medetomidine (0.015 ml/kg i.m., Domitor® Vet, Orion Oyj, Espoo, Finland) and intubated. The sheep were controlled with a heart monitor during the operation.

Fentanyl (2 µg/kg/hour, Durogesic®, Fentanyl ratiopharm, Ratiopharm GmbH, Ulm, Germany) depot plaster was given preoperatively for 72 h pain relief. Additionally, 2 ml of Fentanyl (50 µg/ml i.m., Fentanyl-Hameln, Hameln Pharmaceuticals GmbH, Hameln, Germany) was injected intramuscularly during first 72 h after the operation. Then Buprenorfin (0.3 mg/dose i.m., Temgesic®, Schering-Plough Europe, Brussels, Belgium) was injected twice a day continuously for two days or more after the operation when the depot plaster was removed.

Amoxycillin (15 mg/kg i.m., Betamox® Vet, 150 mg/ml, Norbrook Laboratories Ltd, Newry, Nord-Ireland) was injected as antibiotic prophylaxis, intramuscularly into the anterior half of the neck 24 h preoperatively and once per day for two days postoperatively.

Hole defects were induced to the femoral and humeral distal and proximal condyles of the sheep hind and front legs with a drill as described by Nuss et al. (2006). A hole with a diameter of 6 mm and a depth of 10 mm were drilled (cordless drill, Bosch PSR12-2). The drill hole was rinsed with saline to eliminate bone debris and was tamponated with gauzes for several minutes to stop bleeding. Meanwhile, the location of the defect was marked, using 1.0 mm dental, radiopaque, glass-fiber rootcanal posts (Snowpost refill, Plandent Oy, Helsinki, Finland). The posts were cut to suitable length with a diamond blade. The drilled holes were filled according to the randomization table with the test materials or left empty (untreated controls). Finally, the subcutaneous tissues were closed in layers with resorbable continuous 3-0 Polysorb sutures and skin with non-resorbable 2-0 Monosof sutures.

After predetermined time period of 8 weeks the animals were euthanized and bone samples were taken for analysis. Euthanasia were performed with Pentobarbital (60 mg/kg i.v. Mebunat® Vet, Orion Oyj, Espoo, Finland). Before this, sheep were anaesthetised by intramuscularly Medetomidine (0.015 ml/kg Domitor® Vet, Orion Oyj, Espoo, Finland and 0.04 ml/kg Ketalar®, Pfizer Oy, Helsinki, Finland).

After euthanasia the bones were excised and preserved in ice. Then the bone blocks were preserved in 4% buffered formalin first seven days and then in 70% ethanol. Some samples broken in the excised phase and they have removed from the analysis.

2.6 Micro CT Evaluation of Bone Formation

Samples were scanned by using micro computerized tomography (µCT) device (SkyScan, x-ray microtomagraph, University of Turku). Scanned samples were analyzed using CTAn (SkyScan) software. Furthermore, radiography analysis from micro-CT-images was done to show new bone formation and scaffold resorption.

2.7 Statistical Analysis

Statistical analysis was performed using SPSS for Windows. The non-parametric Kruskall-Wallis test was used to evaluate the statistical differences between the groups. The Mann-Whitney U-test was used for pairwise comparisons between the bone protein extract treatment groups, autograft group and the control groups. Values of $p<0.05$ were considered statistically significant.

3 Results

For the groups paste 1 and paste 2 (the bone protein extract and Cambioceramics TCP in PEG-GLY matrix with stearic acid) micro-CT evaluations showed good bone formation in the defect area with both bone protein extract amounts although there were cortical areas without new bone or remnants of TCP granules. Almost all TCP granules had resorbed during the follow-up. In the control group, paste 3 (Cambioceramics in PEG-GLY matrix with stearic acid, with no the bone protein extract), micro-CT evaluations showed that TCP granules had not yet resorbed and had packed as a thick mass into the bottom of the defect. However, there was new bone formation in this granule mass around the granules. For the other control group, granule (pure Cambioceramics TCP), micro-CT evaluations showed that implanted granules had filled whole defect area. The granules had not absorbed during the follow-up but there was seen some new bone formation around the granules.

For the groups paste 4 (the bone protein extract and Cerasorb® M TCP in PEG-GLY matrix with stearic acid) micro-CT evaluations showed the bone formation in the defect area although there were cortical areas without new bone or remnants of TCP granules. Almost all TCP granules had resorbed during the follow-up. For the control group, paste 6 (Cerasorb® M TCP in PEG-GLY matrix with stearic acid, with no the bone protein extract), micro-CT evaluations showed that most of TCP granules had not yet resorbed and had packed as a thick mass into the bottom of the defect. Clear new bone formation was difficult to see.

For the group paste 5 (the bone protein extract and Cerasorb® TCP in PEG-GLY matrix with stearic acid) micro-CT evaluations showed clear and very good new bone formation in the defect area. Almost all TCP granules had absorbed during the follow-up. There was still same problem as in the other groups included PEG-GLY matrix and stearic acid that implant (granules) had not filled whole defect and there was some empty areas, especially in the cortical site.

For the group autograft radiography evaluations showed clear bone formation and bone remodelling in the defect area. Empty areas in the cortical sites were not seen, except couple of defects.

For the demineralised bone matrix group grafton (Grafton Plus® DBM) and in the untreated group micro-CT evaluations showed no new bone formation in the defect sites during the follow-up.

Figure 21:
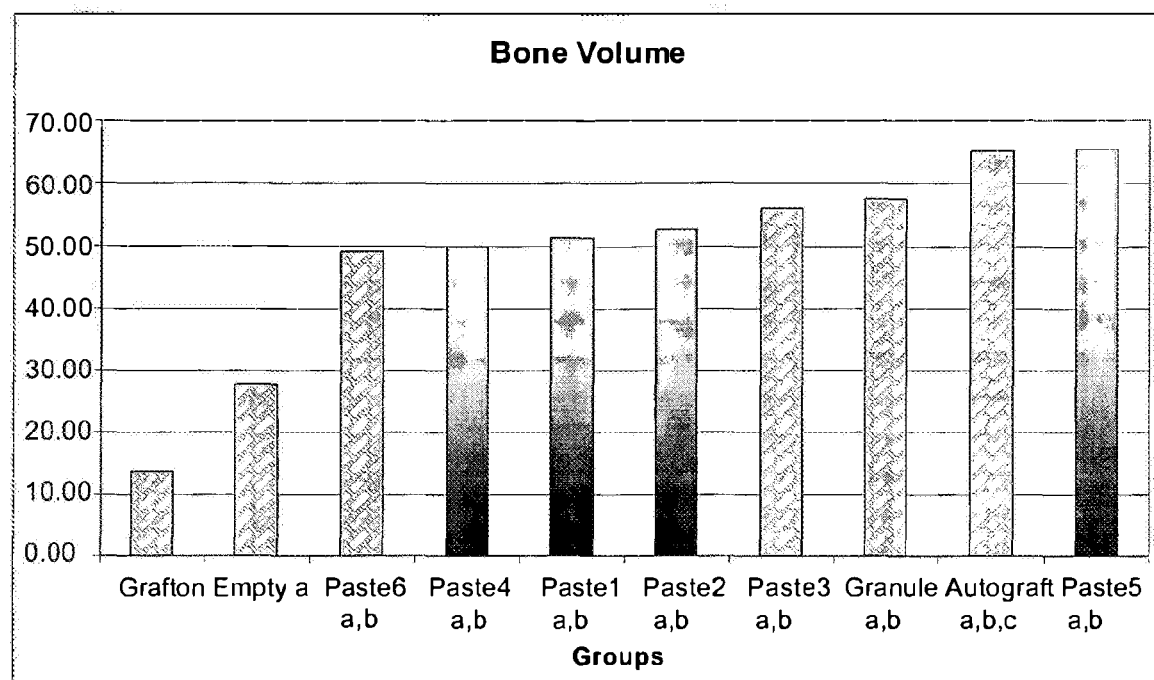
FIG. 21 shows bone volumes measured from micro-CT images. In statistic comparisons all other groups were significantly better than demineralised bone matrix (Grafton Plus® DBM) group ($^a$p<0.02). All bone protein extract implant groups, the autograft group and also other control groups except DBM group had healed significantly better than untreated defects ($^b$p<0.02). The autograft group was significantly better in bone volume than the paste 4 group ($^c$p<0.02). Control groups have been marked as prick pattern.

Bone volume value was measured from micro-CTs by image analysis (FIG. 21). The highest bone volume was seen in the paste 5 and autograft groups, whereas the lowest bone volume was in the demineralised bone matrix and empty defect groups. In statistic comparisons all other groups were significantly better than demineralised bone matrix (Grafton Plus® DBM) group (p<0.02). All bone protein extract implant groups, the autograft group and also other control groups except DBM group had healed significantly better than untreated defects (p<0.02). The autograft group was significantly better in bone volume than the paste 4 group (p<0.02) and near to significantly better than the paste 6 group (p<0.06). The paste 5 group was near to significantly better in bone volume compared to the paste 4 group (p=0.064).

4 Discussion

The aims of this study were to compare three development reindeer protein extract formulations with autograft, and commercially available bone fillers (demineralised bone matrix and tricalcium phosphate particles) for their ability to form new bone using a hole defect model of sheep cancellous bone. Furthermore, the purpose was to provide information about the potential effect of the protein concentration in the formulation on the bone healing ability and to provide preliminary information on biocompatibility of the formulations. It was found that the planned and tested medical device including the reindeer bone protein extract and $\beta$-TCP formulation in the injectable paste form is a suitable alternative for the nowadays used autograft bone treatment.

The reindeer bone protein extract has high bone formation activity, as seen in the bioactivity and previous tests; however, in a real bone healing situation, the extract cannot work without a scaffold system. Limitations of the carrier selection are set by the characteristics of the reindeer bone protein extract. The primary limitation is that the extract is not water-soluble. Thus, there are at least three different possibilities for implant preparation. The first is that the formulated bone extract suspension can be impregnated into a porous matrix. The second method is to mold the extract and carrier together to form putty or compress them into the discs, and in the third method, the carrier discs or granules are surface coated with the bone extract. Pure collagen has been tested as a carrier in previous studies. Lyophilized extract was mixed into water and then pipetted onto the collagen sponge; alternatively, the collagen sponge was soaked in water and then, with the extract, was bundled up to form an implant. The results of this method showed good bone formation in the pouch mice model and in the segmental defect model; however, it seems that collagen does not support the functionality of the bone forming proteins in the required time. Therefore, an inorganic alternative would provide a better frame for the support of the bone healing effect of the extract. Previously, we have tested combinations of TCP, HAP and coral together with the extract and collagen sponge in the mouse model. Furthermore, bioglass was found to be an acceptable carrier alternative as tested in the rat defect model.

Various calcium salt alternatives were also tested in a mouse model. This study showed that an inorganic scaffold system is a very suitable carrier for the reindeer bone protein extract. Results of the present study supported previous studies that formation of new bone depends on the ceramic content with high HAP/TCP ratio and high dose of bone proteins. Furthermore, this study confirms that presence of bioactive components reduced fibrous tissue formation and increased bone formation around inorganic scaffolds. However, the amount and availability of bone proteins should be in balance with bone healing and forming cascade. In our preliminary pilot study in sheep (data not shown) we founded that $\beta$-TCP granules may be a better scaffold material than calcium sulfate because TCP has slower resorption speed. However, without bone extract the resorption of TCP is also too slow. Furthermore, our mouse model study showed that stearic acid can add bone formation capacity of the reindeer bone protein extract with calcium scaffold.

According to this previous information we prepared implants including the formulated reindeer bone protein extract together with commercial available $\beta$-TCP granules in PEG-GLY matrix with stearic acid. Dosing form was an injectable paste which was possible when PEG-GLY matrix was used. PEG is widely used as precipitate in medicine manufacturing and for example it is used in a number of toothpastes as a dispersant because it has a low toxicity, binds water and helps keep gum uniform throughout the toothpaste. Also glycerol (GLY) is widely used in pharmaceutical formulations as improving smoothness and providing lubrication. The implantation was easy to do and no extra mixing of product was needed on the operation table. However, the analysis showed that the used amount of granules was not enough to fill the whole defect area after the matrix was dissolved away, which caused that cortical site of defect was usually empty without new bone or remnant of granules. This was compared to the pure TCP group in which the granule amount was double and the whole defect area was full of the granules also after the follow-up. Thus, effect of bone healing cannot be compared only by difference in bone formation between the study groups, and optimizing of PEG-GLY matrix together with stearic acid and granules is needed. Ideally, bone formation and scaffold degradation follow one another until the defect area has been replaced completely by new bone. As long as bone formation is not extensive enough to supply mechanical strength, the scaffold material should degrade so slowly that support characteristic does not expose. Analyzing of radiographs showed that granule resorption was the fastest in the group including the bone protein extract but there was also good new bone formation seen and bone remodelling was on going. In the group that involved only granules or granules with PEG-GLY matrix and stearic acid the resorption of granules was not observed. The bone formation was seen but usually only around the granules. In our preliminary pilot study (data not shown) this bone formation was like phosphate apatite layer around the granules and no real bone union between granules was seen. This confirms the results that bone protein extract increased bioactivity of inorganic materials. Histology and scanned electron microscopy (SEM) imaging could confirm our micro-CT result conclusion. The highest bone volume and bone formation was seen in the group that involved a smaller and spherical TCP granule form. It has been found that the form, shape and micro- and nanostructures of the scaffold affect on both bone forming and scaffold resorption properties. Possibly, the form of granule improved attaching of bone proteins, growth factors and signalling molecules to the surface of granules and the scaffold worked most optimally in this group.

Grafton Plus® DBM has been authorized by the United States Food and Drug Administration (FDA) (510k) as a bone graft substitute, bone graft extender, and bone void filler in bony voids or gaps of the skeletal system. Grafton® DBM products have been widely used and good bone healing results have been reported in various animal models, especially with rats and rabbits. It has also good clinical results as treatment of spinal problems. Thus, it was surprising that demineralized bone matrix did not work in the present study. There are some studies in the literature in which bone healing differences between different commercial available DBM products has been found. Furthermore, DBM has much lower bone forming effect compared to the recombinant product. Sheep model was used in this study. It could be that sheep as a model is not suitable for Grafton or other human DBM products compared to other DBM product as Collos which has given superior healing results in sheep and dog models.

In this study one aim was to compare ceramic implant, containing the reindeer bone protein extract, with autograft. The results showed that autograft was not better in bone forming or defect healing as the bone protein extract in TCP-scaffold. This was an encouraging result when finding a substitute method for the autograft treatment which has limitations because harvesting of bone grafts can lead to complications, such as bleeding, pain, and infection. Previous results with DBM materials support our results.

In conclusion, the β-TCP-granules in the PEG-GLY matrix with stearic acid is a workable scaffold system for the reindeer bone protein extract but proportional amount of granules in matrix must be yet optimised. The planned and tested medical device including the reindeer bone protein extract and β-TCP formulation in the injectable form is the suitable alternative for the nowadays used autograft treatment.

Formulations as Continued from the Citrate Dialysis Step:

A lyophilizate is prepared by freeze-drying the precipitate obtained from the citrate dialysis step using suitable lyoprotectants:

An excipients solution is prepared in excess containing surfactant (Polysorbat 20), lyoprotectant (Trehalose), bulking agent (Glycine) and buffer (Mannitol) in WFI-water. The solution is sterilized in an autoclave. The protein dry content from the citrate dialysis step is analyzed by weighing and an appropriate amount of the sterilized excipients solution is added. The mixture is mixed with a suitable mixer until a homogeneous suspension is formed. The homogeneous protein-excipients-suspension is dispensed into freeze-drying trays or unit dose vials and subsequently freeze-dried. The freeze-dried protein extract contain then by weight 0.35% Polysorbat, 0.97% trehalose, 4.1% glycine, 10.9% mannitol and 83.7% protein extract.

The excipients solution was tested and selected using a Design of Experiments (DoE) approach with the following factor levels:

Surfactant: Polysorbat 20 or Polysorbat 80 (0.01-1.06%)
Lyoprotectant: trehalose or sucrose (0.2-2.3%)
Bulking agent: glycine or CMC (1.0-10%)
Buffer: mannitol or histidine (3.2-23%)

At least five different formulations have been tested with the selected lyophilizate composition.

TABLE 17

The test articles and study groups

| Group | N | Bone protein extract | Scaffold |
|---|---|---|---|
| Paste 1 | 8 | 60 mg reindeer bone protein extract (BBS-Bioactive Bone Substitutes Ltd, Oulu, Finland)/3 cc syringe | Custom-made Cambioceramics (β-TCP (Cambioceramics, Cam Bioceramics, Leiden, The Netherlands), 300-500 µm spherical granules of 1.24 g/cm$^3$ bulk density combined with Polyethylene Glycol/Glycerol (PEG/GLY) (Clariant, Kemi Intressen, and Croda, Kemi Intressen) matrix modified with stearic acid (Stearic acid 50, mixture of fatty acids, consisting mainly of stearic acid and 40-60% palmitic acid, Fluka, Sigma-Aldrich) |
| Paste 2 | 8 | 30 mg reindeer bone protein extract/3 cc syringe | Cambioceramics β-TCP, 300-500 µm of 1.24 g/cm$^3$ bulk density combined with PEG-GLY matrix modified with stearic acid |
| Paste 3 | 8 | — | Cambioceramics β-TCP, 300-500 µm of 1.24 g/cm$^3$ bulk density combined with PEG-GLY matrix modified with stearic acid |
| Paste 4 | 7 | 60 mg reindeer bone protein extract/3 cc syringe | Curasan β-TCP Cerasorb M (Cerasorb ® M Ortho, Curasan AG, Frankfurt, Germany), 500-1000 µm morsels of 0.61 g/cm$^3$ density combined with PEG-GLY matrix modified with stearic acid |
| Paste 5 | 8 | 60 mg reindeer bone protein extract/3 cc syringe | Curasan β-TCP Cerasorb (Cerasorb ®, Curasan AG, Frankfurt, Germany), 500-1000 µm spherical granules of 1.21-1.24 g/cm$^3$ bulk density combined with PEG-GLY matrix modified with stearic acid |
| Paste 6 | 8 | — | Curasan β-TCP Cerasorb ® M, 500-1000 µm morsels of 0.61-0.64 g/cm$^3$ bulk density combined with PEG-GLY matrix modified with stearic acid |
| Granule | 7 | — | Cambioceramics β-TCP, 300-500 µm of 1.24 g/cm$^3$ bulk density. The amount of granules was double compared the granule amount in the paste groups. |
| Autograft | 8 | — | — |
| Grafton | 7 | DBM (Grafton Plus ® Demineralized Bone Matrix 1 cc (DBM) Paste, Osteotech Inc., Eatontown, New Jersey, USA) | — |
| Empty defect | 8 | — | — |

Formulation 1 comprises the above mentioned lyophilizate freeze-dried in unit dose vials. The lyophilizate is reconstituted with saline solution after which it can be injected through a needle.

Formulation 2 comprises the above mentioned lyophilizate freeze-dried in unit dose vials. The lyophilizate is reconstituted with saline solution after which it can be impregnated into various scaffolds. Examples of suitable scaffolds are porous TCP or TCP/HAP discs or porous polymer composites.

Formulation 3 comprises the above mentioned lyophilizate freeze-dried in unit dose vials. The lyophilizate is mixed with calcium salt (calcium sulfate, calcium phosphate) to form a moldable paste/putty. The paste/putty can be shaped by hand or molded into suitable discs or pellets.

Material for 60 mg dose:
1. Vial [1]—60 mg lyophilizate
2. Vial [2]—1 g saline solution
3. Vial [3]—calcium sulfate hemihydrate
4. Vial [4]—mixing bowl
5. Disc mold
6. Spatula Instruction for Use:
1. Open the 60 mg lyophilized formulation vial [1] and add 1 g saline solution [2]. Mix until a homogeneous suspension is formed
2. Dispense the 2 g CS hemihydrate vial [1] into the mixing bowl [4] and add the suspension from vial [2]
3. Mix for 60 seconds using the spatula [6]
4. A paste can be formed within 5 min, and it hardens within 5-10 minutes
5. Fill the disc mold [5] with the paste and let harden
6 The scaffolds are ready for implanting when removed from the mold after 60 min Formulation 4 comprises the above mentioned lyophilizate freeze-dried in trays (lyoguards). The lyophilizate is mixed with calcium sulfate and stearic acid and compressed to suitable pellets.

Manufacturing of Calcium Sulfate-Stearic Acid Pellets

The CS/stearic acid pellets are manufactured in the clean room.

First an excess calcium sulfate hemihydrate is mixed with WFI-water and extruded so that a string of calcium sulfate dihydrate (gypsum) is formed. After 60 min when hardened, the string(s) is cut into pellets, and then grained down into small granules the following day.

An excess amount of stearic acid is sieved through a 1 mm sieve in order to remove the larger particles.

The content of one lyophilized vial is mixed with 1.5 g calcium sulfate and 0.5 g stearic acid in a small bowl.

Pellets of 5 mm diameter are formed by weighing 100 mg of the powder blend into the tablet press, and then pressed for 10-15 seconds. Pellets are filled into a glass vial and labeled.

Formulation 5 comprises an injectable paste containing the above mentioned lyophilizate, and delivered in a suitable syringe system. The paste is composed of polyethylene glycol (PEG 2000), glycerol and stearic acid, together with spherical tricalcium phosphate (TCP) granules.

A paste is prepared by weighing 37% PEG 2000, 59% Glycerin and 3.5% stearic acid in a paste mixer. The mixture is heated above the melting point of PEG and stearic acid (60-70° C.). The mixture is allowed to slowly cool down during continuous mixing until a paste has been formed at room temperature. Appropriate amount of the above mentioned lyophilizate and TCP-granules are added and mixed until homogeneous. The paste is filled into syringes and packed in aluminium foil. The final product contain 1.27% protein extract, 0.01% Tween, 0.01% Trehalose, 0.06% Glycine, 0.16% Mannitol, 28.9% TCP, 41.2% Glycerol, 26.0% PEG 2000 and 2.43% Stearic acid.

Formulation 6 comprises surface coated pellets or granules. The animal tissue extract is mixed with film forming agents and then spray coated on the pellets.

Preparation of Gypsum Pellets
Material (Per Mold):
10 g calcium sulfate hemihydrate (Beta): Sigma-Aldrich
0.5 g (5%) stearic acid: Merck, Parteck
5 ml WFI-water: Fresenius Kabi, (One-Med)
Preparation (6 Molds):

Calcium sulfate (61 g) and stearic acid (3.0 g) are mixed as follows: Raw material is pressed through a 1 mm sieve in turns in small amounts to mix them as layerwise. After this they are mixed with a spoon to a homogenous mixture.

Calcium sulfate-stearic acid (10.5 g) is added to WFI water (5 ml) and mixed until an uniform mixture is obtained (about 30 seconds). The mixture is mold to a silicone mould and let to harden under a plastic membrane. The mixture is mouldable for about 5 minutes and the moulded pellets may be removed from the mould after about 60 minutes.

The dust and larger moulding residues formed during the moulding process are removed by sieving. The final hardening occurs during 24 hours (under a protective sheet).

Dry pellets are packed in Minigrip bags patchwise (2×67 g) and stored in cold room on drying material.

Coating of Gypsum Pellets

The materials used in the coating are listed in Tables 18-20.

TABLE 18

| Composition: | |
| --- | --- |
| Material | Per dose (2 g) |
| Protein extract | 60 mg |
| Tween 20 | 0.44 mg |
| CMC | 13.2 mg |
| PEG 400 | 2.20 mg |
| Gypsum pellet | 1921 mg |

TABLE 19

| Coating solution (dry content of the sprayed suspension: 3%) | |
| --- | --- |
| Material | Amount |
| CMC | 1.63 g |
| PEG 400 | 0.27 g |
| TWEEN 20 | 0.5 g |
| WFI-water | 100 g |
| TWEEN-20/water | 10 g |
| WFI-water | 290 g |

TABLE 20

| Coating solution and the amount of pellets per batch: | | |
| --- | --- | --- |
| Material | Amount | Provider/quality |
| Gypsum pellet | 67 g | BBS Oy |
| Protein extract | 7 g | BBS OY, YHD 200809 |
| Coating solution | 146 g | BBS OY |

7 g of protein extract is weighed to mixing container and 146 g of excipient solution is added. The mixture is mixed until it is visually homogenous. The suspension is kept homogenous with magnetic stirrer whole time during the coating.

Fluidized bed granulator is loaded with 67 g of calcium sulfate pellets (3×3 mm). The pellets are fluidized first for 30 seconds to remove the extra gypsum dust. The coating is started by starting the coating solution feeding pump. During the coating the feed of the coating solution, the position of the injector head, the floating of the pellets and sticking thereof to the chamber walls are monitored The sticking of the pellets to the chamber walls is prevented by pulsing the feed in order to let the pellets dry (e.g. in 15 second cycles).

The coating is stopped when the whole coating solution has been sprayed and the extra moisture has evaporated from the surface of the pellets i.e. the moisture and the temperature of the outgoing air has become stable. Too long fluidizing is not recommended because the pellets will start grounding and the protein may be worn away from the surface.

What is claimed is:

1. A method of making a reindeer bone protein guanidine hydrochloride extract comprising
    a) demineralizing a reindeer bone in HCl while mixing until the pH remains constant between 2.8 and 3.0 for at least two hours;
    b) washing the demineralized reindeer bone of (a) in water, wherein the pH of water in the last washing step is between 2.4 and 2.6; and
    c) extracting the washed demineralized reindeer one of (b) with guanidine hydrochloride at a pH of 3.9 to 4.5, wherein said reindeer bone protein guanidine hydrochloride extract comprises Matrix Gla protein, a species of SPP-24 (secreted phosphoprotein), which migrates on SDS-PAGE at approximately 15 kDa, BMP-2, BMP-7 and TGF-beta 1.

2. The method of claim 1, further comprising filtering the extract of (c) with a microfilter with a cut-off size in the range of 0.1-10 μm to obtain a flow-through fraction of bone protein extract.

3. The method of claim 2, further comprising filtering the flow-through fraction of bone protein extract with a cassette ultrafilter having a cut-off size in the range of 5-10 kDa to obtain a retentate fraction of bone protein extract.

4. The method of claim 3, further comprising mixing the retentate fraction of bone protein extract with a polyethylene glycol/glycerol (PEG-GLY) matrix, and combining this mixture with calcium salt granules to generate a bone preparation.

5. The method of claim 3, further comprising dialyzing the retentate fraction of bone protein extract with water to obtain a wet extract.

6. The method of claim 5, further comprising re-dissolving the wet extract into guanidine hydrochloride and subsequently dialyzing the re-dissolved guanidine hydrochloride extract with citrate buffer to obtain a precipitate.

7. The method of claim 6, further comprising mixing the precipitate with a polyethylene glycol/glycerol (PEG-GLY) matrix, and combining this mixture with calcium salt granules to generate a bone preparation.

8. The method of claim 1, wherein said reindeer bone protein guanidine hydrochloride extract further comprises a species of biglycan, which migrates at approximately 15 kDa on SDS-PAGE.

9. The method of claim 1, wherein said reindeer bone protein guanidine hydrochloride extract further comprises a species of chondroadherin, which migrates at approximately 15 kDa on SDS-PAGE.

10. The method of claim 8, wherein said reindeer bone protein guanidine hydrochloride extract further comprises a species of chondroadherin, which migrates at approximately 15 kDa on SDS-PAGE.

* * * * *

UNITED STATES PATENT AND TRADEMARK OFFICE
CERTIFICATE OF CORRECTION

Page 1 of 1

PATENT NO.         : 11,219,665 B2
APPLICATION NO.    : 16/867434
DATED              : January 11, 2022
INVENTOR(S)        : Hanna Tolli It is certified that error appears in the above-identified patent and that said Letters Patent is hereby corrected as shown below:

In the Drawings

Sheet 3 of 34 (Fig. 5A), Line 1 (Y axis), delete "0,35 0,3 0,25, 0,2, 0,15 0,1 0,05 0" and insert -- 0.35 0.3 0.25 0.2 0.15 0.1 0.05 0 --.

Sheet 3 of 34 (Fig. 5B), Line 1 (Y axis), delete "0,4 0,35 0,3 0,25 0,2 0,15 0,1 0,05 0" and insert -- 0.4 0.35 0.3 0.25 0.2 0.15 0.1 0.05 0 --.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*